US010008672B2

(12) United States Patent
Stoessel et al.

(10) Patent No.: US 10,008,672 B2
(45) Date of Patent: Jun. 26, 2018

(54) COMPOUNDS FOR ELECTRONIC DEVICES

(71) Applicant: Merck Patent GmbH, Darmstadt (DE)

(72) Inventors: Philipp Stoessel, Frankfurt Am Main (DE); Frank Voges, Bad Duerkheim (DE); Arne Buesing, Frankfurt Am Main (DE); Christof Pflumm, Darmstadt (DE); Teresa Mujica-Fernaud, Darmstadt (DE); Christian Wirges, Darmstadt (DE)

(73) Assignee: Merck Patent Gmbh, Darmstadt (DE)

( * ) Notice: Subject to any disclaimer, the term of this patent is extended or adjusted under 35 U.S.C. 154(b) by 877 days.

(21) Appl. No.: 14/364,120

(22) PCT Filed: Nov. 15, 2012

(86) PCT No.: PCT/EP2012/004744
§ 371 (c)(1),
(2) Date: Jun. 10, 2014

(87) PCT Pub. No.: WO2013/087142
PCT Pub. Date: Jun. 20, 2013

(65) Prior Publication Data
US 2014/0312287 A1    Oct. 23, 2014

(30) Foreign Application Priority Data
Dec. 12, 2011  (EP) ..................... 11009779

(51) Int. Cl.
*H01L 51/54* (2006.01)
*C09K 11/06* (2006.01)
*H01L 51/00* (2006.01)
*C07C 211/54* (2006.01)
*H01L 51/50* (2006.01)

(52) U.S. Cl.
CPC ........ *H01L 51/0059* (2013.01); *C07C 211/54* (2013.01); *H01L 51/0085* (2013.01); *H01L 51/0087* (2013.01); *C07C 2603/18* (2017.05); *H01L 51/0067* (2013.01); *H01L 51/5056* (2013.01); *Y02E 10/549* (2013.01)

(58) Field of Classification Search
CPC ... C07C 211/43; C07C 211/54; C07C 211/55; C07C 2103/18; Y02E 10/549; C09K 11/06; C09K 2211/00; C09K 2211/10; C09K 2211/1003; C09K 2211/1007; C09K 2211/1014; H01L 51/0032; H01L 51/005; H01L 51/0051; H01L 51/0059; H01L 51/006; H01L 51/0061; H01L 51/0067; H01L 51/0085; H01L 51/0087; H01L 51/50; H01L 51/5012; H01L 51/5016; H01L 51/5056
USPC ....... 428/690, 691, 917, 411.4, 336; 427/58, 427/66; 313/500–512; 257/40, 88–104, 257/E51.001–E51.052; 252/301.16–301.35, 519.21, 500; 564/307

See application file for complete search history.

(56) References Cited

U.S. PATENT DOCUMENTS

| 4,992,350 | A | 2/1991 | Sasaki et al. |
| 5,262,261 | A | 11/1993 | Kikuchi et al. |
| 8,182,933 | B2 | 5/2012 | Osaka et al. |
| 2002/0193551 | A1 | 12/2002 | Pei |
| 2007/0215889 | A1 | 9/2007 | Kawakami et al. |
| 2009/0066227 | A1 | 3/2009 | Okinaka et al. |
| 2009/0072718 | A1 | 3/2009 | Nomura et al. |
| 2009/0102368 | A1 | 4/2009 | Shitagaki et al. |
| 2010/0019657 | A1 | 1/2010 | Eum et al. |
| 2010/0099890 | A1 | 4/2010 | Ogita et al. |
| 2010/0108997 | A1 | 5/2010 | Kim et al. |
| 2010/0237339 | A1 | 9/2010 | Nomura et al. |
| 2011/0198581 | A1 | 8/2011 | Yabunouchi |
| 2013/0207046 | A1 | 8/2013 | Pflumm et al. |
| 2016/0190447 | A1 | 6/2016 | Pflumm et al. |

FOREIGN PATENT DOCUMENTS

| EP | 0376311 A2 | 7/1990 |
| EP | 1683804 A2 | 7/2006 |
| JP | H-02178667 A | 7/1990 |
| JP | 07-053955 A | 2/1995 |
| JP | H0748324 A | 2/1995 |
| JP | 08/006267 A | 1/1996 |
| JP | 09325508 A | 12/1997 |
| JP | H1095972 A | 4/1998 |
| JP | 2000/219659 A | 8/2000 |
| JP | 2003-201472 | 7/2003 |

(Continued)

OTHER PUBLICATIONS

Machine translation of JP2009-010364. Date of publication: Jan. 15, 2009.*
Zhao et al., "Highly Solid-State Emissive para-Terphenyls Laterally Substituted with a Diphenylamino Group", Chemical Communications, 2011, vol. 47, pp. 5518-5520.
Wang et al., "N,N-Diarylanilinosquaraines and their Application to Organic Photovoltaics", Chemistry of Materials, 2011, vol. 23, pp. 4789-4798.
Zhao et al., "Highly Solid-State Emissive para-terphenyls Laterally Substituted with a Diphenylamino Group", Chem. Commun., 2011, vol. 47, pp. 5518-5520.

(Continued)

*Primary Examiner* — Andrew K Bohaty
(74) *Attorney, Agent, or Firm* — Kim Winston LLP

(57) ABSTRACT

The invention relates to arylamino compounds and to the use thereof in electronic devices, for example organic electroluminescent devices. The invention furthermore relates to electronic devices comprising one or more of the said compounds, for example as hole-transport materials in a corresponding functional layer of the device. The invention furthermore relates to a process for the preparation of the said compounds, and to a formulation comprising one or more of the said compounds.

10 Claims, No Drawings

(56) References Cited

FOREIGN PATENT DOCUMENTS

| | | |
|---|---|---|
| JP | 2003201472 A | 7/2003 |
| JP | 2004534872 A | 11/2004 |
| JP | 2005/116247 A | 4/2005 |
| JP | 3824385 | 9/2006 |
| JP | 2007/091719 A | 4/2007 |
| JP | 2007/284431 A | 11/2007 |
| JP | 2007/318063 A | 12/2007 |
| JP | 4110173 B2 | 7/2008 |
| JP | 2008239613 A | 10/2008 |
| JP | 2009/010364 A | 1/2009 |
| JP | 2009-147276 | 7/2009 |
| JP | 2009147276 A | 7/2009 |
| JP | 2009/215281 A | 9/2009 |
| JP | 2010/132638 A | 6/2010 |
| JP | 2010/222268 A | 10/2010 |
| JP | 2011-084717 | 4/2011 |
| JP | 201184717 A | 4/2011 |
| JP | 5917521 B2 | 5/2016 |
| KR | 10-2011-0022605 | 3/2011 |
| WO | WO-02/051958 A1 | 7/2002 |
| WO | WO-2006/123667 A1 | 11/2006 |
| WO | WO-2010/044130 A1 | 4/2010 |

OTHER PUBLICATIONS

Hellwinkel et al., "Ring Closure of 2'-Heterosubstituted Biphenyl-2-diazonium Salts to (Spiro)cyclic Tetraarylammonium Salts and Tribenz [b.d.f] azepines", Chem. Ber. 1972, vol. 105, pp. 880-906.
Korean Office Action for Korean Application No. 10-2014-7019148, dated Jan. 20, 2017 with translation, 12 pages.

* cited by examiner

COMPOUNDS FOR ELECTRONIC DEVICES

RELATED APPLICATIONS

This application is a national stage application filed pursuant to 35 U.S.C. § 371 of PCT/EP2012/004744, filed Nov. 15, 2012, which claims the benefit of European Patent Application No. 11009779.7, filed Dec. 12, 2011, which is incorporated herein by reference in its entirety.

The invention relates to arylamino compounds and to the use thereof in electronic devices, for example organic electroluminescent devices. The invention furthermore relates to electronic devices comprising one or more of the said compounds, for example as hole-transport materials in a corresponding functional layer of the device. The invention furthermore relates to a process for the preparation of the said compounds, and to a formulation comprising one or more of the said compounds.

The development of functional compounds for use in electronic devices is of considerable interest. The aim here is, in particular, the development of compounds with which improved properties of the electronic devices in one or more relevant points can be achieved, such as, for example, power efficiency, lifetime or colour coordinates of the emitted light.

In accordance with the present invention, the term electronic device is taken to mean, inter alia, organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and organic electroluminescent devices (OLEDs).

Of particular interest is the provision of compounds for use in the last-mentioned electronic devices called OLEDs. The general structure and functional principle of OLEDs is known to the person skilled in the art and is described, inter alia, in U.S. Pat. Nos. 4,539,507, 5,151,629, EP 0676461 and WO 1998/27136.

Further improvements are still necessary with respect to the performance data of OLEDs, in particular in view of broad commercial use, for example in display devices or as light sources. Of particular importance in this connection are the lifetime, the efficiency and the operating voltage of the OLEDs and the colour values achieved. In particular in the case of blue-emitting OLEDs, there is potential for improvement with respect to the lifetime of the devices. In addition, it is desirable for the compounds for use as functional materials in electronic devices to have high thermal stability and a high glass-transition temperature and to be sublimable without decomposition.

In this connection, there is, in particular, a need for alternative hole-transport materials. In the case of hole-transport materials in accordance with the prior art, the voltage generally increases with the layer thickness of the hole-transport layer. In practice, a greater layer thickness of the hole-transport layer would frequently be desirable, but this often has the consequence of a higher operating voltage and worse performance data. In this connection, there is a need for novel hole-transport materials which have high charge-carrier mobility, enabling thicker hole-transport layers to be achieved with only a slight increase in the operating voltage.

Furthermore, there is a need for hole-transport materials which can be prepared simply and inexpensively. Still furthermore, there is a need for hole-transport materials which can be prepared in highly pure form.

The prior art (JP 1995/053955 A) discloses the use of triarylamino compounds, such as, for example, tris(para-biphenyl)amine or tris(para-triphenyl)amine, in OLEDs.

Furthermore, the prior art (WO 2006/123667 A1 and JP 2010/222268 A) discloses the use of triarylamino compounds which have para- and meta-links of the individual aromatic rings, in OLEDs.

Still furthermore, JP 2007/91719 A discloses the use of triarylamino compounds which contain a 1,3,5-triphenyl-substituted phenyl group as aryl group, in OLEDs.

However, there continues to be a need for compounds which are suitable as functional materials in OLEDs, in particular as hole-transport materials.

It has now been found that compounds of the formula (I) shown below can be used extremely well as functional materials in OLEDs.

The invention thus relates to a compound of the formula (I)

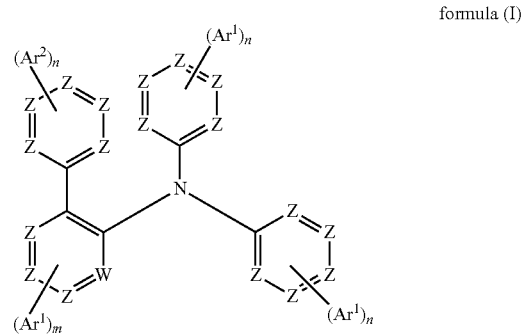

formula (I)

where the following applies to the symbols and indices occurring:

Z is on each occurrence, identically or differently, $CR^1$ or N, where Z is equal to C if a group $Ar^1$ or $Ar^2$ is bonded;

W is equal to CH or N;

$Ar^1$ is on each occurrence, identically or differently, an aromatic or heteroaromatic ring system having 6 to 30 aromatic ring atoms, which may be substituted by one or more radicals $R^1$;

$Ar^2$ is on each occurrence, identically or differently, an aromatic or heteroaromatic ring system having 6 to 24 aromatic ring atoms, which may be substituted by one or more radicals $R^1$;

$R^1$ is on each occurrence, identically or differently, H, D, F, Cl, Br, I, $C(=O)R^2$, CN, $Si(R^2)_3$, $NO_2$, $P(=O)(R^2)_2$, $S(=O)R^2$, $S(=O)_2R^2$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals $R^2$ and where one or more $CH_2$ groups in the above-mentioned groups may be replaced by $-R^2C=CR^2-$, $-C\equiv C-$, $Si(R^2)_2$, $C=O$, $C=S$, $C=NR^2$, $-C(=O)O-$, $-C(=O)NR^2-$, $NR^2$, $P(=O)(R^2)$, $-O-$, $-S-$, SO or $SO_2$ and where one or more H atoms in the above-mentioned groups may be replaced by D, F, Cl, Br, I, CN or $NO_2$, or an aromatic or heteroaromatic ring system having 5 to 30 aromatic ring atoms, which may in each case be substituted by one or more radicals $R^2$, where two or more radicals $R^1$ may be linked to one another and may form a ring;

$R^2$ is on each occurrence, identically or differently, H, D, F, Cl, Br, I, C(=O)R$^3$, CN, Si(R$^3$)$_3$, NO$_2$, P(=O)(R$^3$)$_2$, S(=O)R$^3$, S(=O)$_2$R$^3$, a straight-chain alkyl, alkoxy or thioalkyl group having 1 to 20 C atoms or a branched or cyclic alkyl, alkoxy or thioalkyl group having 3 to 20 C atoms or an alkenyl or alkynyl group having 2 to 20 C atoms, where the above-mentioned groups may each be substituted by one or more radicals R$^3$ and where one or more CH$_2$ groups in the above-mentioned groups may be replaced by —R$^3$C=CR$^3$—, —C≡C—, Si(R$^3$)$_2$, C=O, C=S, C=NR$^3$, —C(=O)O—, —C(=O)NR$^3$—, NR$^3$, P(=O)(R$^3$), —O—, —S—, SO or SO$_2$ and where one or more H atoms in the above-mentioned groups may be replaced by D, F, Cl, Br, I, CN or NO$_2$, or an aromatic or heteroaromatic ring system having 5 to 30 aromatic ring atoms, which may in each case be substituted by one or more radicals R$^3$, where two or more radicals R$^2$ may be linked to one another and may form a ring;

$R^3$ is on each occurrence, identically or differently, H, D, F or an aliphatic, aromatic or heteroaromatic organic radical having 1 to 20 C atoms, in which, in addition, one or more H atoms may be replaced by D or F; two or more substituents R$^3$ here may be linked to one another and may form a ring;

n is on each occurrence, identically or differently, 0, 1, 2, 3, 4 or 5;

m is on each occurrence, identically or differently, 0, 1, 2 or 3;

where the three groups which are bonded to the central nitrogen atom, regarded as a whole, are not all identical, and where the following compounds are excluded from the claim scope:

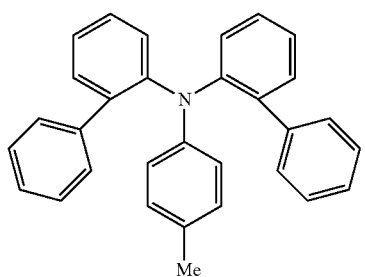

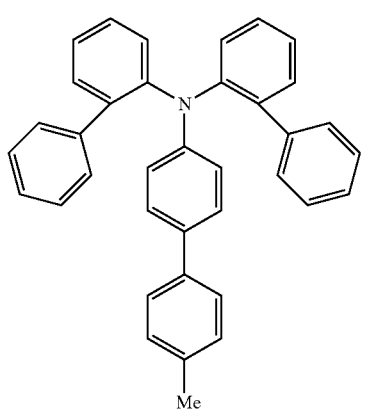

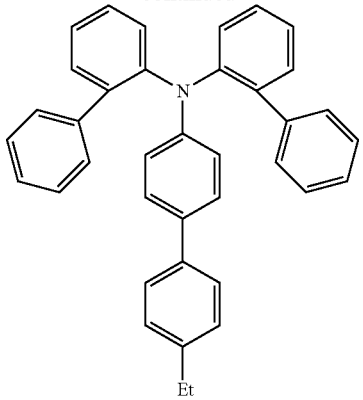

The compounds according to the invention and the organic electroluminescent devices according to the invention are distinguished by the following surprising advantages over the prior art:

The compounds according to the invention are very highly suitable for use in a hole-transport layer or a hole-injection layer of an organic electroluminescent device, in particular owing to their high hole mobility.

The compounds are readily accessible synthetically and can be prepared inexpensively.

On use in OLEDs, the compounds effect a long lifetime of the devices, preferably in combination with high efficiency.

Furthermore, the compounds are distinguished by a low tendency towards crystallisation, in particular compared with symmetrical compounds.

General term definitions, which apply for the purposes of the present application, are given below.

The formulation that the three groups bonded to the central nitrogen atom, regarded as a whole, are not all identical is taken to mean that the three complete chemical groups which are bonded to the central nitrogen atom are not all identical. Substituents are also taken into account here. It is not taken into account whether the part of the group bonded directly to the nitrogen atom, for example the first phenyl group of a terphenyl group, is identical or different compared with a corresponding part of the other groups.

Preferably, two of the three complete chemical groups which are bonded to the central nitrogen atom are identical. According to an alternative preferred embodiment, all three groups are different.

The compound of the formula (I) preferably contains no three-fold axis of symmetry through the nitrogen atom.

A substitution by —(Ar$^1$)$_n$ is taken to mean that n identical or different groups Ar$^1$ are bonded to the corresponding six-membered ring, in each case in different positions of the six-membered ring. A corresponding definition applies to a substitution by —(Ar$^2$)$_m$.

An aryl group in the sense of this invention contains 6 to 60 aromatic ring atoms; a heteroaryl group in the sense of this invention contains 5 to 60 aromatic ring atoms, at least one of which is a heteroatom. The heteroatoms are preferably selected from N, O and S. This represents the basic definition. If other preferences are indicated in the description of the present invention, for example with respect to the number of aromatic ring atoms or the heteroatoms present, these apply.

An aryl group or heteroaryl group here is taken to mean either a simple aromatic ring, i.e. benzene, or a simple heteroaromatic ring, for example pyridine, pyrimidine or thiophene, or a condensed (annellated) aromatic or heteroaromatic polycycle, for example naphthalene, phenanthrene, quinoline or carbazole. A condensed (annellated) aromatic or heteroaromatic polycycle in the sense of the present application consists of two or more simple aromatic or heteroaromatic rings condensed with one another.

An aryl or heteroaryl group, which may in each case be substituted by the above-mentioned radicals and which may be linked to the aromatic or heteroaromatic ring system via any desired positions, is taken to mean, in particular, groups derived from benzene, naphthalene, anthracene, phenanthrene, pyrene, dihydropyrene, chrysene, perylene, fluoranthene, benzanthracene, benzophenanthrene, tetracene, pentacene, benzopyrene, furan, benzofuran, isobenzofuran, dibenzofuran, thiophene, benzothiophene, isobenzothiophene, dibenzothiophene, pyrrole, indole, isoindole, carbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, pyrazine, phenazine, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole.

An aromatic ring system in the sense of this invention contains 6 to 60 C atoms in the ring system. A heteroaromatic ring system in the sense of this invention contains 5 to 60 aromatic ring atoms, at least one of which is a heteroatom. The heteroatoms are preferably selected from N, O and/or S. An aromatic or heteroaromatic ring system in the sense of this invention is intended to be taken to mean a system which does not necessarily contain only aryl or heteroaryl groups, but instead in which, in addition, a plurality of aryl or heteroaryl groups may be connected by a non-aromatic unit (preferably less than 10% of the atoms other than H), such as, for example, an $sp^3$-hybridised C, Si, N or O atom, an $sp^2$-hybridised C or N atom or an sp-hybridised C atom. Thus, for example, systems such as 9,9'-spirobifluorene, 9,9'-diarylfluorene, triarylamine, diaryl ether, stilbene, etc., are also intended to be taken to be aromatic ring systems in the sense of this invention, as are systems in which two or more aryl groups are connected, for example, by a linear or cyclic alkyl, alkenyl or alkynyl group or by a silyl group. Furthermore, systems in which two or more aryl or heteroaryl groups are linked to one another via single bonds are also taken to be aromatic or heteroaromatic ring systems in the sense of this invention, such as, for example, systems such as biphenyl, terphenyl or diphenyltriazine.

An aromatic or heteroaromatic ring system having 5-60 aromatic ring atoms, which may in each case also be substituted by radicals as defined above and which may be linked to the aromatic or heteroaromatic group via any desired positions, is taken to mean, in particular, groups derived from benzene, naphthalene, anthracene, benzanthracene, phenanthrene, benzophenanthrene, pyrene, chrysene, perylene, fluoranthene, naphthacene, pentacene, benzopyrene, biphenyl, biphenylene, terphenyl, terphenylene, quaterphenyl, fluorene, spirobifluorene, dihydrophenanthrene, dihydropyrene, tetrahydropyrene, cis- or trans-indenofluorene, truxene, isotruxene, spirotruxene, spiroisotruxene, furan, benzofuran, isobenzofuran, dibenzofuran, thiophene, benzothiophene, isobenzothiophene, dibenzothiophene, pyrrole, indole, isoindole, carbazole, indolocarbazole, indenocarbazole, pyridine, quinoline, isoquinoline, acridine, phenanthridine, benzo-5,6-quinoline, benzo-6,7-quinoline, benzo-7,8-quinoline, phenothiazine, phenoxazine, pyrazole, indazole, imidazole, benzimidazole, naphthimidazole, phenanthrimidazole, pyridimidazole, pyrazinimidazole, quinoxalinimidazole, oxazole, benzoxazole, naphthoxazole, anthroxazole, phenanthroxazole, isoxazole, 1,2-thiazole, 1,3-thiazole, benzothiazole, pyridazine, benzopyridazine, pyrimidine, benzopyrimidine, quinoxaline, 1,5-diazaanthracene, 2,7-diazapyrene, 2,3-diazapyrene, 1,6-diazapyrene, 1,8-diazapyrene, 4,5-diazapyrene, 4,5,9,10-tetraazaperylene, pyrazine, phenazine, phenoxazine, phenothiazine, fluorubin, naphthyridine, azacarbazole, benzocarboline, phenanthroline, 1,2,3-triazole, 1,2,4-triazole, benzotriazole, 1,2,3-oxadiazole, 1,2,4-oxadiazole, 1,2,5-oxadiazole, 1,3,4-oxadiazole, 1,2,3-thiadiazole, 1,2,4-thiadiazole, 1,2,5-thiadiazole, 1,3,4-thiadiazole, 1,3,5-triazine, 1,2,4-triazine, 1,2,3-triazine, tetrazole, 1,2,4,5-tetrazine, 1,2,3,4-tetrazine, 1,2,3,5-tetrazine, purine, pteridine, indolizine and benzothiadiazole, or combinations of these groups.

For the purposes of the present invention, a straight-chain alkyl group having 1 to 40 C atoms or a branched or cyclic alkyl group having 3 to 40 C atoms or an alkenyl or alkynyl group having 2 to 40 C atoms, in which, in addition, individual H atoms or $CH_2$ groups may be substituted by the groups mentioned above under the definition of the radicals, is preferably taken to mean the radicals methyl, ethyl, n-propyl, i-propyl, n-butyl, i-butyl, s-butyl, t-butyl, 2-methylbutyl, n-pentyl, s-pentyl, cyclopentyl, neopentyl, n-hexyl, cyclohexyl, neohexyl, n-heptyl, cycloheptyl, n-octyl, cyclooctyl, 2-ethylhexyl, trifluoromethyl, pentafluoroethyl, 2,2,2-trifluoroethyl, ethenyl, propenyl, butenyl, pentenyl, cyclopentenyl, hexenyl, cyclohexenyl, heptenyl, cycloheptenyl, octenyl, cyclooctenyl, ethynyl, propynyl, butynyl, pentynyl, hexynyl or octynyl. An alkoxy or thioalkyl group having 1 to 40 C atoms is preferably taken to mean methoxy, trifluoromethoxy, ethoxy, n-propoxy, i-propoxy, n-butoxy, i-butoxy, s-butoxy, t-butoxy, n-pentoxy, s-pentoxy, 2-methylbutoxy, n-hexoxy, cyclohexyloxy, n-heptoxy, cycloheptyloxy, n-octyloxy, cyclooctyloxy, 2-ethylhexyloxy, pentafluoroethoxy, 2,2,2-trifluoroethoxy, methylthio, ethylthio, n-propylthio, i-propylthio, n-butylthio, i-butylthio, s-butylthio, t-butylthio, n-pentylthio, s-pentylthio, n-hexylthio, cyclohexylthio, n-heptylthio, cycloheptylthio, n-octylthio, cyclooctylthio, 2-ethylhexylthio, trifluoromethylthio, pentafluoroethylthio, 2,2,2-trifluoroethylthio, ethenylthio, propenylthio, butenylthio, pentenylthio, cyclopentenylthio, hexenylthio, cyclohexenylthio, heptenylthio, cycloheptenylthio, octenylthio, cyclooctenylthio, ethynylthio, propynylthio, butynylthio, pentynylthio, hexynylthio, heptynylthio or octynylthio.

The formulation that two or more radicals may form a ring with one another is, for the purposes of the present application, intended to be taken to mean, inter alia, that the two radicals are linked to one another by a chemical bond. This is illustrated by the following scheme:

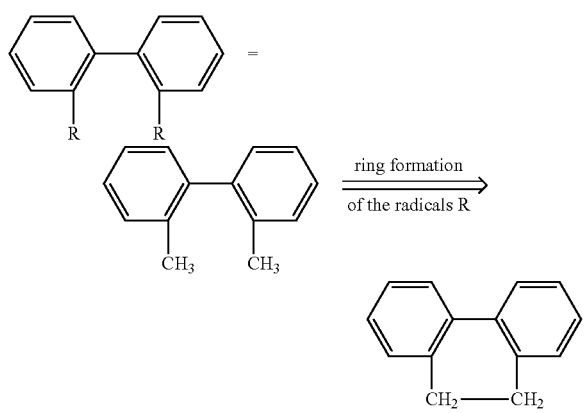

Furthermore, however, the above-mentioned formulation is also intended to be taken to mean that, in the case where one of the two radicals represents hydrogen, the second radical is bonded at the position to which the hydrogen atom was bonded, with formation of a ring. This is intended to be illustrated by the following scheme:

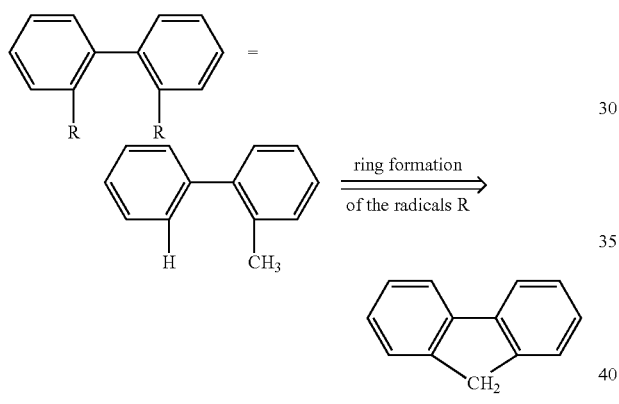

For the compounds according to the invention, the embodiments described below are preferred. They may occur independently of one another, but preferably occur in combination.

The compounds according to the invention preferably contains no arylamino group apart from the triarylamino group explicitly depicted in formula (I).

The compound according to the invention furthermore preferably contains no carbazole, indole, pyrrole or fluorenyl group.

Carbazole derivatives in the sense of the present invention are also taken to mean carbazole derivatives with condensed-on groups, such as, for example, indenocarbazoles or indolocarbazoles, as well as carbazole derivatives in which one or more carbon atoms in the aromatic six-membered rings have been replaced by nitrogen. An analogous situation applies to the pyrrole, indole and fluorenyl groups mentioned above.

The compound according to the invention particularly preferably contains no heteroaryl group and no heteroaromatic ring system.

The group W is preferably equal to CH.

The group Z is preferably equal to $CR^1$, where it is equal to C if a group $Ar^1$ or $Ar^2$ is bonded to it.

Preferably, not more than two adjacent groups Z are equal to N. Furthermore preferably, 0, 1, 2 or 3 groups Z in a ring are equal to N, particularly preferably 0, 1, or 2, very particularly preferably 0 or 1.

$Ar^1$ is furthermore preferably on each occurrence, identically or differently, an aromatic or heteroaromatic ring system having 6 to 18 aromatic ring atoms, preferably having 6 to 12 aromatic ring atoms, where $Ar^1$ may be substituted by one or more radicals $R^1$. Particular preference is given to an aromatic ring system having the above-mentioned number of aromatic ring atoms. Even greater preference is given to phenyl or biphenyl which is substituted by one or more radicals $R^1$.

$Ar^1$ is particularly preferably a group of the formula $(Ar^1-1)$

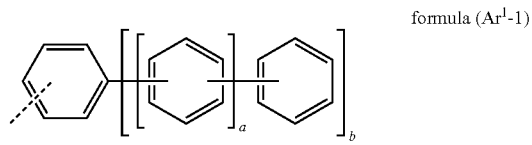

formula $(Ar^1-1)$ where a group $R^1$ may be bonded at each of the free positions, and where a and b may each, identically or differently, be 0 or 1, and where the group is bonded to the parent structure of the formula (I) via the dashed bond, or a group of the formula $(Ar^1-2)$

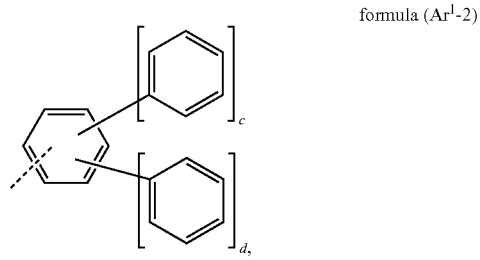

formula $(Ar^1-2)$ where a group $R^1$ may be bonded at each of the free positions, and where c and d may each, identically or differently, be 0 or 1, and where the group is bonded to the parent structure of the formula (I) via the dashed bond.

Very particularly preferred embodiments of the group $Ar^1$ conform to the following formulae $(Ar^1-a)$ to $(Ar^1-d)$

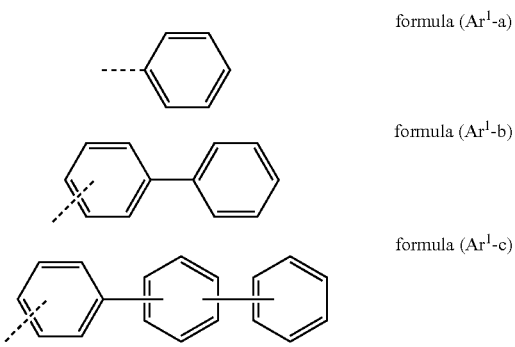

formula $(Ar^1-a)$ formula $(Ar^1-b)$ formula $(Ar^1-c)$

-continued formula (Ar¹-d)

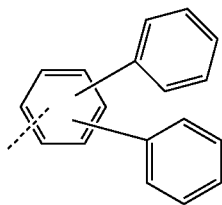

where a radical R¹ may be bonded at each of the free positions and the group is bonded to the parent structure of the formula (I) via the dashed bond.

Furthermore preferably, at least one of the groups Ar¹ in the compound of the formula (I) is bonded to the six-membered ring in the meta-position to the bond to the central nitrogen atom.

Furthermore preferably, no group Ar¹ is bonded on the six-membered ring in the ortho-position to the bond to the central nitrogen atom.

Ar² is furthermore preferably on each occurrence, identically or differently, an aromatic or heteroaromatic ring system having 6 to 12 aromatic ring atoms, preferably having 6 aromatic ring atoms, where Ar² may be substituted by one or more radicals R¹. Particular preference is given to an aromatic ring system having the above-mentioned number of aromatic ring atoms. Even greater preference is given to phenyl which is substituted by one or more radicals R¹.

Ar² is particularly preferably a group of the formula (A-3)

formula (A-3)

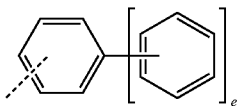

where a group R¹ may be bonded at each of the free positions, and where e may in each case, identically or differently, be 0 or 1, and where the group is bonded to the parent structure of the formula (I) via the dashed bond.

Very particularly preferred embodiments of the group Ar² conform to the following formulae (Ar²-a) to (Ar²-b)

formula (Ar²-a)

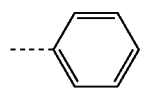

formula (Ar²-b)

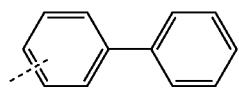

where a radical R¹ may be bonded at each of the free positions and the group is bonded to the parent structure of the formula (I) via the dashed bond.

Furthermore preferably, R¹ is on each occurrence, identically or differently, H, D, F, CN, $Si(R^2)_3$, a straight-chain alkyl or alkoxy group having 1 to 10 C atoms or a branched or cyclic alkyl or alkoxy group having 3 to 10 C atoms, where the above-mentioned groups may each be substituted by one or more radicals R² and where one or more $CH_2$ groups in the above-mentioned groups may be replaced by —C≡C—, —$R^2C=CR^2$—, $Si(R^2)_2$, C=O, C=$NR^2$, —$NR^2$—, —O—, —S—, —C(=O)O— or —C(=O)$NR^2$—, or an aromatic or heteroaromatic ring system having 5 to 20 aromatic ring atoms, which may in each case be substituted by one or more radicals R², where two or more radicals R¹ may in each case be linked to one another and may form a ring.

Radicals R¹ which are bonded to different aromatic or heteroaromatic rings are preferably not linked to one another with ring formation.

Furthermore preferably, R² is on each occurrence, identically or differently, H, D, F, CN, $Si(R^3)_3$, a straight-chain alkyl or alkoxy group having 1 to 10 C atoms or a branched or cyclic alkyl or alkoxy group having 3 to 10 C atoms, where the above-mentioned groups may each be substituted by one or more radicals R³ and where one or more $CH_2$ groups in the above-mentioned groups may be replaced by —C≡C—, —$R^3C=CR^3$—, $Si(R^3)_2$, C=O, C=$NR^3$, —$NR^3$—, —O—, —S—, —C(=O)O— or —C(=O)$NR^3$—, or an aromatic or heteroaromatic ring system having 5 to 20 aromatic ring atoms, which may in each case be substituted by one or more radicals R³, where two or more radicals R² may be linked to one another and may form a ring.

n is preferably on each occurrence, identically or differently, 0, 1, 2 or 3, particularly preferably equal to 1 or 2.

It is furthermore preferred for the sum of the indices n to be at least 1. It is particularly preferably at least 2. It is very particularly preferably at least 3.

m is preferably equal to 0 or 1, particularly preferably equal to 0.

Preferred embodiments of the compound according to the invention conform to one of the formulae (I-1) to (I-12)

formula (I-1)

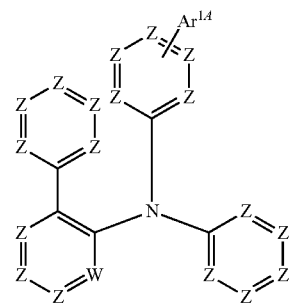

formula (I-2)

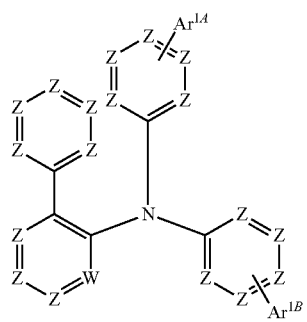

formula (I-3)
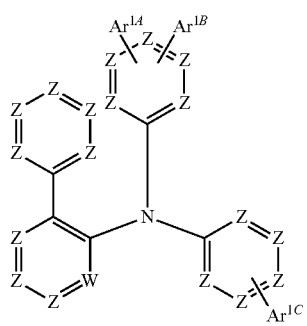
formula (I-4)
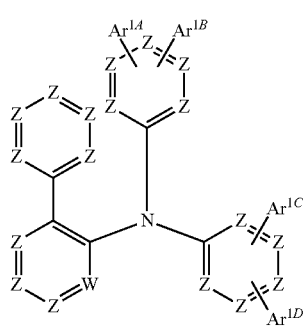
formula (I-5)
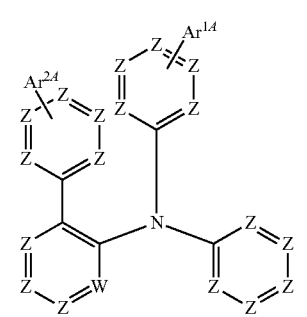
formula (I-6)
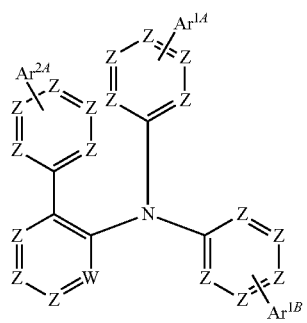
formula (I-7)
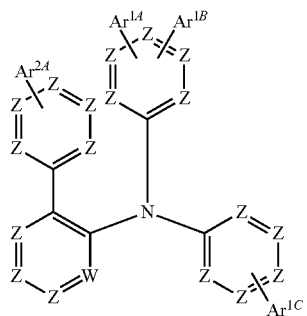
formula (I-8)
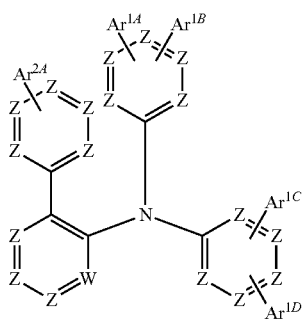
formula (I-9)
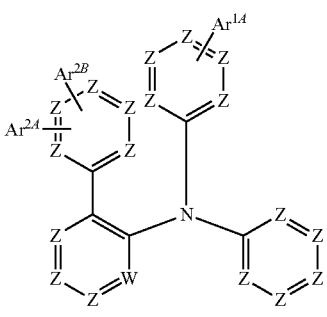
formula (I-10)
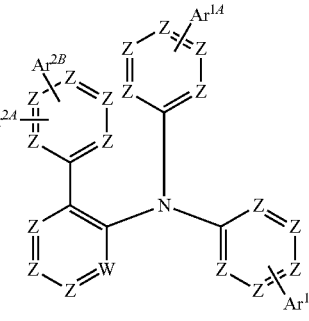
formula (I-11)
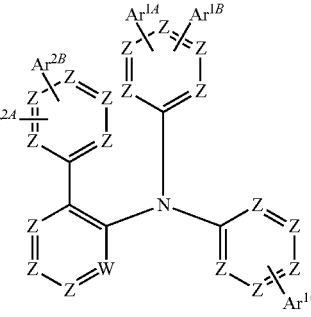
formula (I-12)
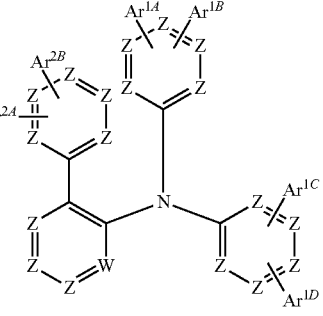

where the symbols occurring are as defined above and $Ar^{1A}$, $Ar^{1B}$, $Ar^{1C}$ and $Ar^{1D}$ is defined like $Ar^1$ and $Ar^{2A}$ and $Ar^{2B}$ are defined like $Ar^2$.

$Ar^{1A}$, $Ar^{1B}$, $Ar^{1C}$ and $Ar^{1D}$ may be identical or different. $Ar^{2A}$ and $Ar^{2B}$ may be identical or different.

Z in the formulae (I-1) to (I-12) is preferably equal to $CR^1$ or equal to C if a group $Ar^1$ or $Ar^2$ is bonded.

Furthermore, W in the formulae (I-1) to (I-12) is preferably equal to CH.

Furthermore, the preferred embodiments indicated above preferably apply to the groups $Ar^1$, $Ar^2$ and $R^1$.

Preference is furthermore given to compounds of the following formulae derived from formula (I-1), (I-2), (I-5) and (I-6):

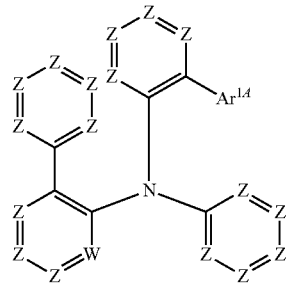

formula (I-1-A)

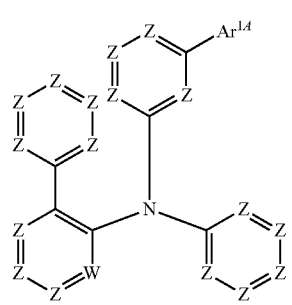

formula (I-1-B)

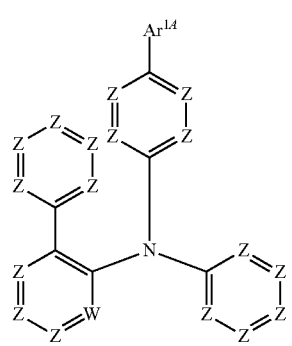

formula (I-1-C)

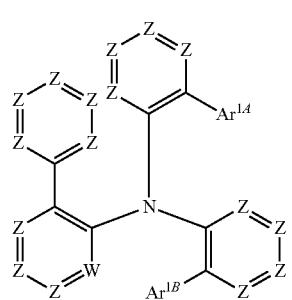

formula (I-2-A)

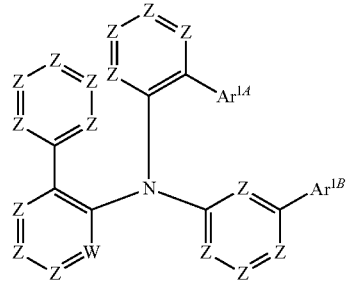

formula (I-2-B)

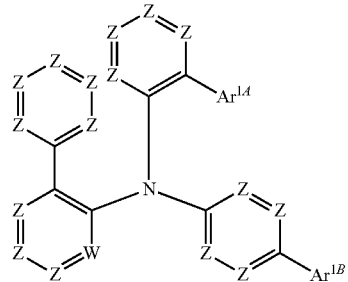

formula (I-2-C)

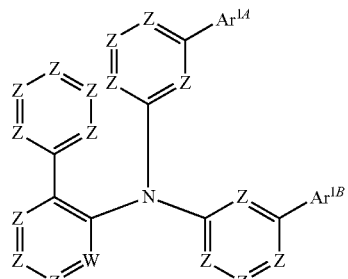

formula (I-2-D)

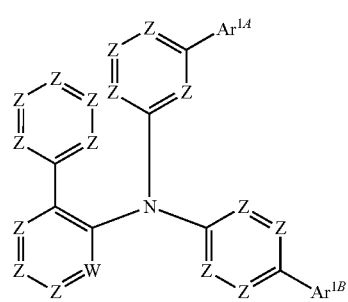

formula (I-2-E)

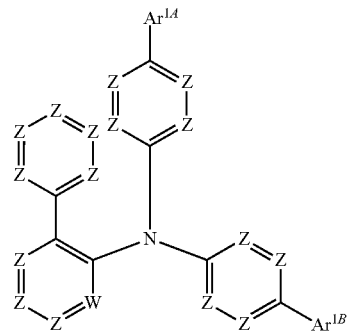

formula (I-2-F)

formula (I-5-A)
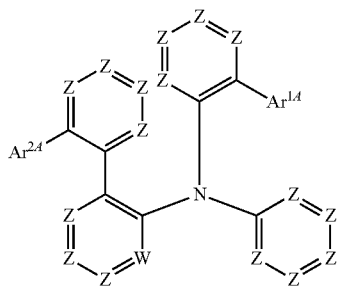
formula (I-5-B)
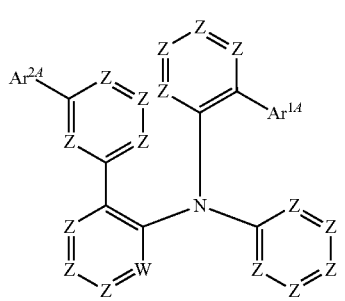
formula (I-5-C)
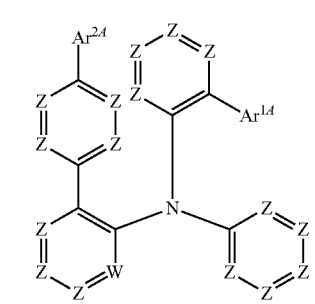
formula (I-5-D)
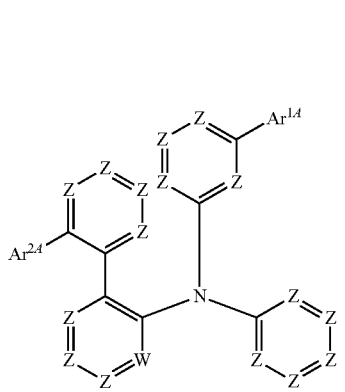
formula (I-5-E)
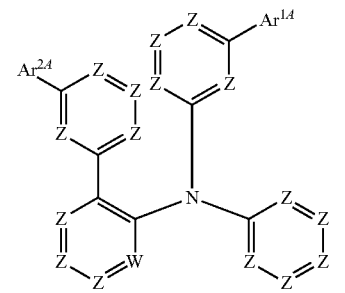
formula (I-5-F)
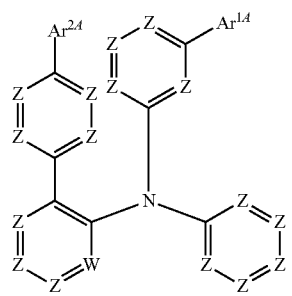
formula (I-5-G)
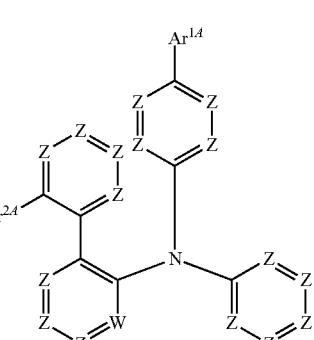
formula (I-5-H)
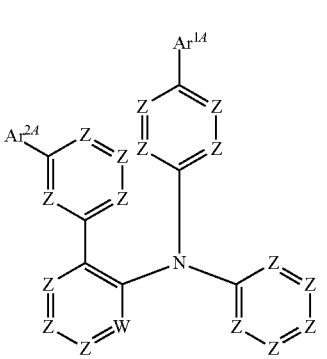
formula (I-5-I)
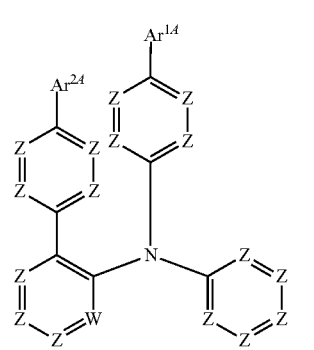
formula (I-6-A)
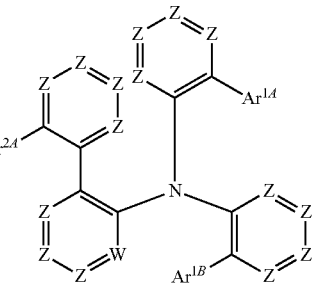

formula (I-6-B)
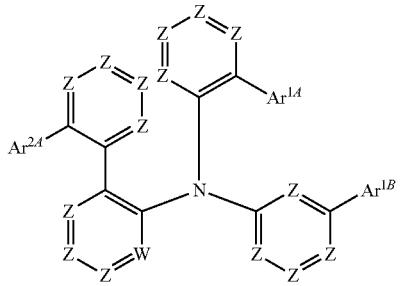
formula (I-6-C)
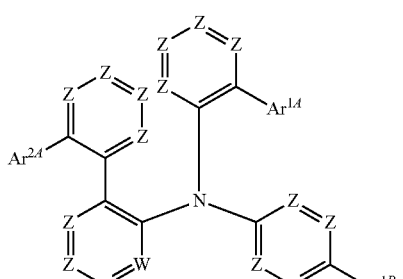
formula (I-6-D)
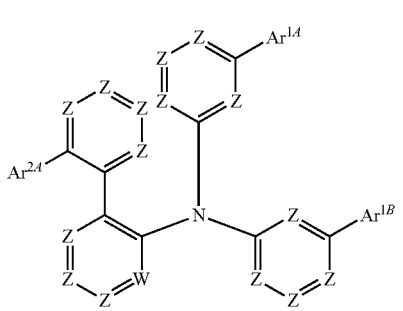
formula (I-6-E)
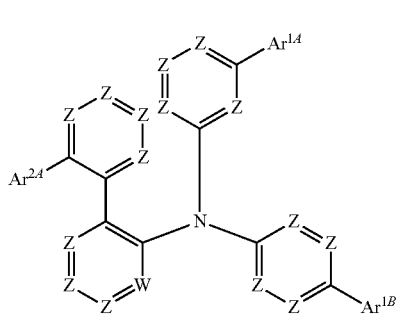
formula (I-6-F)
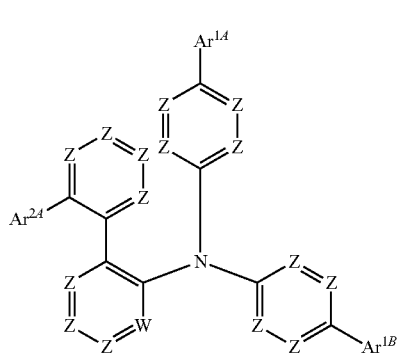
formula (I-6-G)
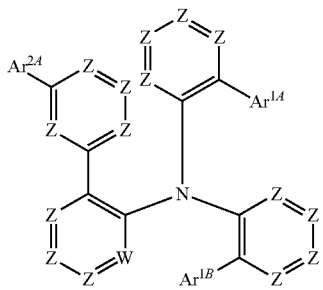
formula (I-6-H)
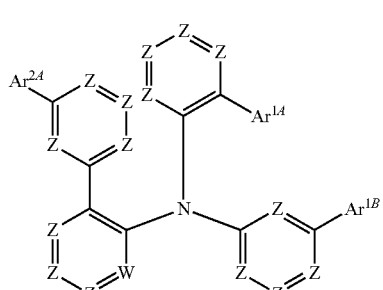
formula (I-6-I)
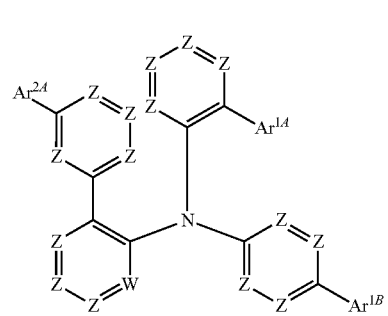
formula (I-6-J)
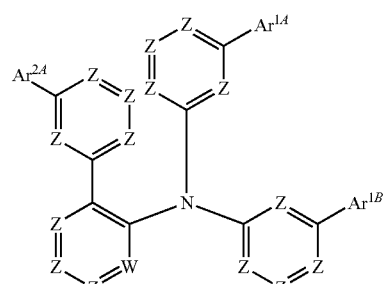
formula (I-6-K)
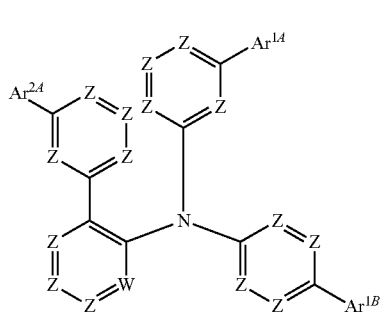

formula (I-6-L)

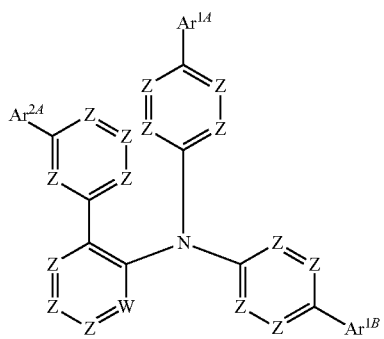

formula (I-6-M)

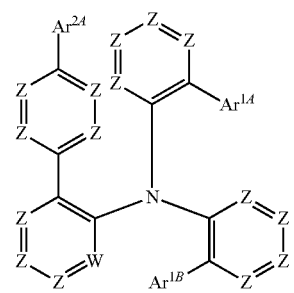

formula (I-6-N)

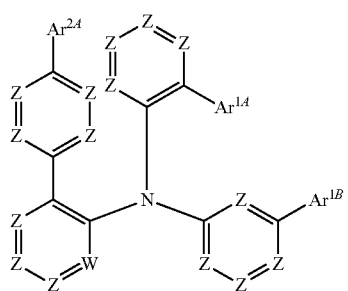

formula (I-6-O)

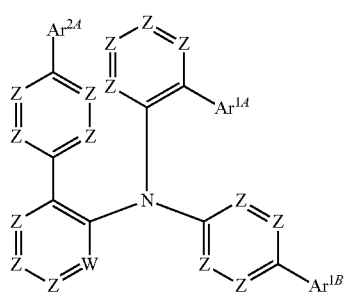

formula (I-6-P)

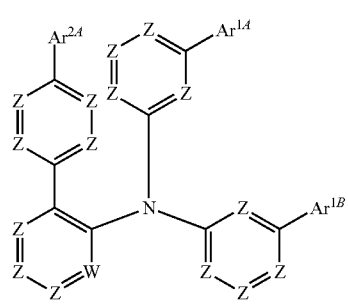

formula (I-6-Q)

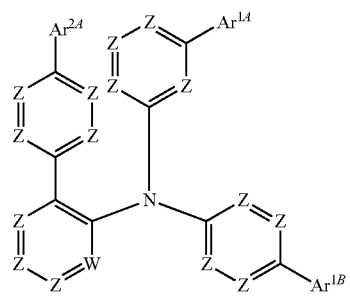

formula (I-6-R)

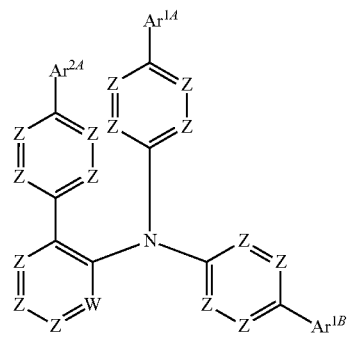

where the symbols occurring are as defined above and $Ar^{1A}$ and $Ar^{1B}$ are defined like $Ar^1$ and $Ar^{2A}$ is defined like $Ar^2$.

$Ar^{1A}$ and $Ar^{1B}$ may be identical or different.

$Ar^{1A}$ and $Ar^{1B}$ are preferably groups of the formulae ($Ar^1$-a) to ($Ar^1$-d). $Ar^{2A}$ is preferably a group of the formula ($Ar^2$-a) or ($Ar^2$-b).

Z in above formulae is preferably equal to $CR^1$ or equal to C if a group $Ar^1$ or $Ar^2$ is bonded.

Furthermore, W in the above formulae is preferably equal to CH.

Furthermore, the preferred embodiments indicated above preferably apply to the groups $Ar^1$, $Ar^2$ and $R^1$.

Very particular preference is given to the structures shown in the following table, where Z is equal to $CR^1$ or C and W is equal to CH.

|  | Parent structure | $Ar^{1A}$ | $Ar^{1B}$ | $Ar^{1C}$ | $Ar^{1D}$ | $Ar^{2A}$ | $Ar^{2B}$ |
|---|---|---|---|---|---|---|---|
| (I-1-1) | (I-1) | ($Ar^1$-a) | — | — | — | — | — |
| (I-1-2) | (I-1) | ($Ar^1$-b) | — | — | — | — | — |
| (I-1-3) | (I-1) | ($Ar^1$-c) | — | — | — | — | — |
| (I-1-4) | (I-1) | ($Ar^1$-d) | — | — | — | — | — |
| (I-2-1) | (I-2) | ($Ar^1$-a) | ($Ar^1$-a) | — | — | — | — |
| (I-2-2) | (I-2) | ($Ar^1$-a) | ($Ar^1$-b) | — | — | — | — |
| (I-2-3) | (I-2) | ($Ar^1$-a) | ($Ar^1$-c) | — | — | — | — |
| (I-2-4) | (I-2) | ($Ar^1$-a) | ($Ar^1$-d) | — | — | — | — |
| (I-2-5) | (I-2) | ($Ar^1$-b) | ($Ar^1$-b) | — | — | — | — |
| (I-2-6) | (I-2) | ($Ar^1$-b) | ($Ar^1$-c) | — | — | — | — |
| (I-2-7) | (I-2) | ($Ar^1$-b) | ($Ar^1$-d) | — | — | — | — |
| (I-2-8) | (I-2) | ($Ar^1$-c) | ($Ar^1$-c) | — | — | — | — |
| (I-2-9) | (I-2) | ($Ar^1$-c) | ($Ar^1$-d) | — | — | — | — |
| (I-2-10) | (I-2) | ($Ar^1$-d) | ($Ar^1$-d) | — | — | — | — |
| (I-3-1) | (I-3) | ($Ar^1$-a) | ($Ar^1$-a) | ($Ar^1$-a) | — | — | — |
| (I-3-2) | (I-3) | ($Ar^1$-a) | ($Ar^1$-b) | ($Ar^1$-a) | — | — | — |
| (I-3-3) | (I-3) | ($Ar^1$-a) | ($Ar^1$-c) | ($Ar^1$-a) | — | — | — |
| (I-3-4) | (I-3) | ($Ar^1$-a) | ($Ar^1$-d) | ($Ar^1$-a) | — | — | — |
| (I-3-5) | (I-3) | ($Ar^1$-b) | ($Ar^1$-b) | ($Ar^1$-a) | — | — | — |
| (I-3-6) | (I-3) | ($Ar^1$-b) | ($Ar^1$-c) | ($Ar^1$-a) | — | — | — |
| (I-3-7) | (I-3) | ($Ar^1$-b) | ($Ar^1$-d) | ($Ar^1$-a) | — | — | — |
| (I-3-8) | (I-3) | ($Ar^1$-c) | ($Ar^1$-c) | ($Ar^1$-a) | — | — | — |

| | Parent structure | Ar$^{1A}$ | Ar$^{1B}$ | Ar$^{1C}$ | Ar$^{1D}$ | Ar$^{2A}$ | Ar$^{2B}$ |
|---|---|---|---|---|---|---|---|
| (I-3-9) | (I-3) | (Ar$^1$-c) | (Ar$^1$-d) | (Ar$^1$-a) | — | — | — |
| (I-3-10) | (I-3) | (Ar$^1$-d) | (Ar$^1$-d) | (Ar$^1$-a) | — | — | — |
| (I-3-11) | (I-3) | (Ar$^1$-a) | (Ar$^1$-a) | (Ar$^1$-b) | — | — | — |
| (I-3-12) | (I-3) | (Ar$^1$-a) | (Ar$^1$-b) | (Ar$^1$-b) | — | — | — |
| (I-3-13) | (I-3) | (Ar$^1$-a) | (Ar$^1$-c) | (Ar$^1$-b) | — | — | — |
| (I-3-14) | (I-3) | (Ar$^1$-a) | (Ar$^1$-d) | (Ar$^1$-b) | — | — | — |
| (I-3-15) | (I-3) | (Ar$^1$-b) | (Ar$^1$-b) | (Ar$^1$-b) | — | — | — |
| (I-3-16) | (I-3) | (Ar$^1$-b) | (Ar$^1$-c) | (Ar$^1$-b) | — | — | — |
| (I-3-17) | (I-3) | (Ar$^1$-b) | (Ar$^1$-d) | (Ar$^1$-b) | — | — | — |
| (I-3-18) | (I-3) | (Ar$^1$-c) | (Ar$^1$-c) | (Ar$^1$-b) | — | — | — |
| (I-3-19) | (I-3) | (Ar$^1$-c) | (Ar$^1$-d) | (Ar$^1$-b) | — | — | — |
| (I-3-20) | (I-3) | (Ar$^1$-d) | (Ar$^1$-d) | (Ar$^1$-b) | — | — | — |
| (I-3-21) | (I-3) | (Ar$^1$-a) | (Ar$^1$-a) | (Ar$^1$-c) | — | — | — |
| (I-3-22) | (I-3) | (Ar$^1$-a) | (Ar$^1$-b) | (Ar$^1$-c) | — | — | — |
| (I-3-23) | (I-3) | (Ar$^1$-a) | (Ar$^1$-c) | (Ar$^1$-c) | — | — | — |
| (I-3-24) | (I-3) | (Ar$^1$-a) | (Ar$^1$-d) | (Ar$^1$-c) | — | — | — |
| (I-3-25) | (I-3) | (Ar$^1$-b) | (Ar$^1$-b) | (Ar$^1$-c) | — | — | — |
| (I-3-26) | (I-3) | (Ar$^1$-b) | (Ar$^1$-c) | (Ar$^1$-c) | — | — | — |
| (I-3-27) | (I-3) | (Ar$^1$-b) | (Ar$^1$-d) | (Ar$^1$-c) | — | — | — |
| (I-3-28) | (I-3) | (Ar$^1$-c) | (Ar$^1$-c) | (Ar$^1$-c) | — | — | — |
| (I-3-29) | (I-3) | (Ar$^1$-c) | (Ar$^1$-d) | (Ar$^1$-c) | — | — | — |
| (I-3-30) | (I-3) | (Ar$^1$-d) | (Ar$^1$-d) | (Ar$^1$-c) | — | — | — |
| (I-3-31) | (I-3) | (Ar$^1$-a) | (Ar$^1$-a) | (Ar$^1$-d) | — | — | — |
| (I-3-32) | (I-3) | (Ar$^1$-a) | (Ar$^1$-b) | (Ar$^1$-d) | — | — | — |
| (I-3-33) | (I-3) | (Ar$^1$-a) | (Ar$^1$-c) | (Ar$^1$-d) | — | — | — |
| (I-3-34) | (I-3) | (Ar$^1$-a) | (Ar$^1$-d) | (Ar$^1$-d) | — | — | — |
| (I-3-35) | (I-3) | (Ar$^1$-b) | (Ar$^1$-b) | (Ar$^1$-d) | — | — | — |
| (I-3-36) | (I-3) | (Ar$^1$-b) | (Ar$^1$-c) | (Ar$^1$-d) | — | — | — |
| (I-3-37) | (I-3) | (Ar$^1$-b) | (Ar$^1$-d) | (Ar$^1$-d) | — | — | — |
| (I-3-38) | (I-3) | (Ar$^1$-c) | (Ar$^1$-c) | (Ar$^1$-d) | — | — | — |
| (I-3-39) | (I-3) | (Ar$^1$-c) | (Ar$^1$-d) | (Ar$^1$-d) | — | — | — |
| (I-3-40) | (I-3) | (Ar$^1$-d) | (Ar$^1$-d) | (Ar$^1$-d) | — | — | — |
| (I-5-1) | (I-5) | (Ar$^1$-a) | — | — | — | (Ar$^2$-a) | — |
| (I-5-2) | (I-5) | (Ar$^1$-a) | — | — | — | (Ar$^2$-b) | — |
| (I-5-3) | (I-5) | (Ar$^1$-b) | — | — | — | (Ar$^2$-a) | — |
| (I-5-4) | (I-5) | (Ar$^1$-b) | — | — | — | (Ar$^2$-b) | — |
| (I-5-5) | (I-5) | (Ar$^1$-c) | — | — | — | (Ar$^2$-a) | — |
| (I-5-6) | (I-5) | (Ar$^1$-c) | — | — | — | (Ar$^2$-b) | — |
| (I-5-7) | (I-5) | (Ar$^1$-d) | — | — | — | (Ar$^2$-a) | — |
| (I-5-8) | (I-5) | (Ar$^1$-d) | — | — | — | (Ar$^2$-b) | — |
| (I-6-1) | (I-6) | (Ar$^1$-a) | (Ar$^1$-a) | — | — | (Ar$^2$-a) | — |
| (I-6-2) | (I-6) | (Ar$^1$-a) | (Ar$^1$-b) | — | — | (Ar$^2$-a) | — |
| (I-6-3) | (I-6) | (Ar$^1$-a) | (Ar$^1$-c) | — | — | (Ar$^2$-a) | — |
| (I-6-4) | (I-6) | (Ar$^1$-a) | (Ar$^1$-d) | — | — | (Ar$^2$-a) | — |
| (I-6-5) | (I-6) | (Ar$^1$-b) | (Ar$^1$-b) | — | — | (Ar$^2$-a) | — |
| (I-6-6) | (I-6) | (Ar$^1$-b) | (Ar$^1$-c) | — | — | (Ar$^2$-a) | — |
| (I-6-7) | (I-6) | (Ar$^1$-b) | (Ar$^1$-d) | — | — | (Ar$^2$-a) | — |
| (I-6-8) | (I-6) | (Ar$^1$-c) | (Ar$^1$-c) | — | — | (Ar$^2$-a) | — |
| (I-6-9) | (I-6) | (Ar$^1$-c) | (Ar$^1$-d) | — | — | (Ar$^2$-a) | — |
| (I-6-10) | (I-6) | (Ar$^1$-d) | (Ar$^1$-d) | — | — | (Ar$^2$-a) | — |
| (I-6-11) | (I-6) | (Ar$^1$-a) | (Ar$^1$-a) | — | — | (Ar$^2$-b) | — |
| (I-6-12) | (I-6) | (Ar$^1$-a) | (Ar$^1$-b) | — | — | (Ar$^2$-b) | — |
| (I-6-13) | (I-6) | (Ar$^1$-a) | (Ar$^1$-c) | — | — | (Ar$^2$-b) | — |
| (I-6-14) | (I-6) | (Ar$^1$-a) | (Ar$^1$-d) | — | — | (Ar$^2$-b) | — |
| (I-6-15) | (I-6) | (Ar$^1$-b) | (Ar$^1$-b) | — | — | (Ar$^2$-b) | — |
| (I-6-16) | (I-6) | (Ar$^1$-b) | (Ar$^1$-c) | — | — | (Ar$^2$-b) | — |
| (I-6-17) | (I-6) | (Ar$^1$-b) | (Ar$^1$-d) | — | — | (Ar$^2$-b) | — |
| (I-6-18) | (I-6) | (Ar$^1$-c) | (Ar$^1$-c) | — | — | (Ar$^2$-b) | — |
| (I-6-19) | (I-6) | (Ar$^1$-c) | (Ar$^1$-d) | — | — | (Ar$^2$-b) | — |
| (I-6-20) | (I-6) | (Ar$^1$-d) | (Ar$^1$-d) | — | — | (Ar$^2$-b) | — |
| (I-7-1) | (I-7) | (Ar$^1$-a) | (Ar$^1$-a) | (Ar$^1$-a) | — | (Ar$^2$-a) | — |
| (I-7-2) | (I-7) | (Ar$^1$-a) | (Ar$^1$-b) | (Ar$^1$-a) | — | (Ar$^2$-a) | — |
| (I-7-3) | (I-7) | (Ar$^1$-a) | (Ar$^1$-c) | (Ar$^1$-a) | — | (Ar$^2$-a) | — |
| (I-7-4) | (I-7) | (Ar$^1$-a) | (Ar$^1$-d) | (Ar$^1$-a) | — | (Ar$^2$-a) | — |
| (I-7-5) | (I-7) | (Ar$^1$-b) | (Ar$^1$-b) | (Ar$^1$-a) | — | (Ar$^2$-a) | — |
| (I-7-6) | (I-7) | (Ar$^1$-b) | (Ar$^1$-c) | (Ar$^1$-a) | — | (Ar$^2$-a) | — |
| (I-7-7) | (I-7) | (Ar$^1$-b) | (Ar$^1$-d) | (Ar$^1$-a) | — | (Ar$^2$-a) | — |
| (I-7-8) | (I-7) | (Ar$^1$-c) | (Ar$^1$-c) | (Ar$^1$-a) | — | (Ar$^2$-a) | — |
| (I-7-9) | (I-7) | (Ar$^1$-c) | (Ar$^1$-d) | (Ar$^1$-a) | — | (Ar$^2$-a) | — |
| (I-7-10) | (I-7) | (Ar$^1$-d) | (Ar$^1$-d) | (Ar$^1$-a) | — | (Ar$^2$-a) | — |
| (I-7-11) | (I-7) | (Ar$^1$-a) | (Ar$^1$-a) | (Ar$^1$-b) | — | (Ar$^2$-a) | — |
| (I-7-12) | (I-7) | (Ar$^1$-a) | (Ar$^1$-b) | (Ar$^1$-b) | — | (Ar$^2$-a) | — |
| (I-7-13) | (I-7) | (Ar$^1$-a) | (Ar$^1$-c) | (Ar$^1$-b) | — | (Ar$^2$-a) | — |
| (I-7-14) | (I-7) | (Ar$^1$-a) | (Ar$^1$-d) | (Ar$^1$-b) | — | (Ar$^2$-a) | — |
| (I-7-15) | (I-7) | (Ar$^1$-b) | (Ar$^1$-b) | (Ar$^1$-b) | — | (Ar$^2$-a) | — |
| (I-7-16) | (I-7) | (Ar$^1$-b) | (Ar$^1$-c) | (Ar$^1$-b) | — | (Ar$^2$-a) | — |
| (I-7-17) | (I-7) | (Ar$^1$-b) | (Ar$^1$-d) | (Ar$^1$-b) | — | (Ar$^2$-a) | — |
| (I-7-18) | (I-7) | (Ar$^1$-c) | (Ar$^1$-c) | (Ar$^1$-b) | — | (Ar$^2$-a) | — |
| (I-7-19) | (I-7) | (Ar$^1$-c) | (Ar$^1$-d) | (Ar$^1$-b) | — | (Ar$^2$-a) | — |
| (I-7-20) | (I-7) | (Ar$^1$-d) | (Ar$^1$-d) | (Ar$^1$-b) | — | (Ar$^2$-a) | — |
| (I-7-21) | (I-7) | (Ar$^1$-a) | (Ar$^1$-a) | (Ar$^1$-c) | — | (Ar$^2$-a) | — |
| (I-7-22) | (I-7) | (Ar$^1$-a) | (Ar$^1$-b) | (Ar$^1$-c) | — | (Ar$^2$-a) | — |
| (I-7-23) | (I-7) | (Ar$^1$-a) | (Ar$^1$-c) | (Ar$^1$-c) | — | (Ar$^2$-a) | — |
| (I-7-24) | (I-7) | (Ar$^1$-a) | (Ar$^1$-d) | (Ar$^1$-c) | — | (Ar$^2$-a) | — |
| (I-7-25) | (I-7) | (Ar$^1$-b) | (Ar$^1$-b) | (Ar$^1$-c) | — | (Ar$^2$-a) | — |
| (I-7-26) | (I-7) | (Ar$^1$-b) | (Ar$^1$-c) | (Ar$^1$-c) | — | (Ar$^2$-a) | — |
| (I-7-27) | (I-7) | (Ar$^1$-b) | (Ar$^1$-d) | (Ar$^1$-c) | — | (Ar$^2$-a) | — |
| (I-7-28) | (I-7) | (Ar$^1$-c) | (Ar$^1$-c) | (Ar$^1$-c) | — | (Ar$^2$-a) | — |
| (I-7-29) | (I-7) | (Ar$^1$-c) | (Ar$^1$-d) | (Ar$^1$-c) | — | (Ar$^2$-a) | — |
| (I-7-30) | (I-7) | (Ar$^1$-d) | (Ar$^1$-d) | (Ar$^1$-c) | — | (Ar$^2$-a) | — |
| (I-7-31) | (I-7) | (Ar$^1$-a) | (Ar$^1$-a) | (Ar$^1$-d) | — | (Ar$^2$-a) | — |
| (I-7-32) | (I-7) | (Ar$^1$-a) | (Ar$^1$-b) | (Ar$^1$-d) | — | (Ar$^2$-a) | — |
| (I-7-33) | (I-7) | (Ar$^1$-a) | (Ar$^1$-c) | (Ar$^1$-d) | — | (Ar$^2$-a) | — |
| (I-7-34) | (I-7) | (Ar$^1$-a) | (Ar$^1$-d) | (Ar$^1$-d) | — | (Ar$^2$-a) | — |
| (I-7-35) | (I-7) | (Ar$^1$-b) | (Ar$^1$-b) | (Ar$^1$-d) | — | (Ar$^2$-a) | — |
| (I-7-36) | (I-7) | (Ar$^1$-b) | (Ar$^1$-c) | (Ar$^1$-d) | — | (Ar$^2$-a) | — |
| (I-7-37) | (I-7) | (Ar$^1$-b) | (Ar$^1$-d) | (Ar$^1$-d) | — | (Ar$^2$-a) | — |
| (I-7-38) | (I-7) | (Ar$^1$-c) | (Ar$^1$-c) | (Ar$^1$-d) | — | (Ar$^2$-a) | — |
| (I-7-39) | (I-7) | (Ar$^1$-c) | (Ar$^1$-d) | (Ar$^1$-d) | — | (Ar$^2$-a) | — |
| (I-7-40) | (I-7) | (Ar$^1$-d) | (Ar$^1$-d) | (Ar$^1$-d) | — | (Ar$^2$-a) | — |
| (I-7-41) | (I-7) | (Ar$^1$-a) | (Ar$^1$-a) | (Ar$^1$-a) | — | (Ar$^2$-b) | — |
| (I-7-42) | (I-7) | (Ar$^1$-a) | (Ar$^1$-b) | (Ar$^1$-a) | — | (Ar$^2$-b) | — |
| (I-7-43) | (I-7) | (Ar$^1$-a) | (Ar$^1$-c) | (Ar$^1$-a) | — | (Ar$^2$-b) | — |
| (I-7-44) | (I-7) | (Ar$^1$-a) | (Ar$^1$-d) | (Ar$^1$-a) | — | (Ar$^2$-b) | — |
| (I-7-45) | (I-7) | (Ar$^1$-b) | (Ar$^1$-b) | (Ar$^1$-a) | — | (Ar$^2$-b) | — |
| (I-7-46) | (I-7) | (Ar$^1$-b) | (Ar$^1$-c) | (Ar$^1$-a) | — | (Ar$^2$-b) | — |
| (I-7-47) | (I-7) | (Ar$^1$-b) | (Ar$^1$-d) | (Ar$^1$-a) | — | (Ar$^2$-b) | — |
| (I-7-48) | (I-7) | (Ar$^1$-c) | (Ar$^1$-c) | (Ar$^1$-a) | — | (Ar$^2$-b) | — |
| (I-7-49) | (I-7) | (Ar$^1$-c) | (Ar$^1$-d) | (Ar$^1$-a) | — | (Ar$^2$-b) | — |
| (I-7-50) | (I-7) | (Ar$^1$-d) | (Ar$^1$-d) | (Ar$^1$-a) | — | (Ar$^2$-b) | — |
| (I-7-51) | (I-7) | (Ar$^1$-a) | (Ar$^1$-a) | (Ar$^1$-b) | — | (Ar$^2$-b) | — |
| (I-7-52) | (I-7) | (Ar$^1$-a) | (Ar$^1$-b) | (Ar$^1$-b) | — | (Ar$^2$-b) | — |
| (I-7-53) | (I-7) | (Ar$^1$-a) | (Ar$^1$-c) | (Ar$^1$-b) | — | (Ar$^2$-b) | — |
| (I-7-54) | (I-7) | (Ar$^1$-a) | (Ar$^1$-d) | (Ar$^1$-b) | — | (Ar$^2$-b) | — |
| (I-7-55) | (I-7) | (Ar$^1$-b) | (Ar$^1$-b) | (Ar$^1$-b) | — | (Ar$^2$-b) | — |
| (I-7-56) | (I-7) | (Ar$^1$-b) | (Ar$^1$-c) | (Ar$^1$-b) | — | (Ar$^2$-b) | — |
| (I-7-57) | (I-7) | (Ar$^1$-b) | (Ar$^1$-d) | (Ar$^1$-b) | — | (Ar$^2$-b) | — |
| (I-7-58) | (I-7) | (Ar$^1$-c) | (Ar$^1$-c) | (Ar$^1$-b) | — | (Ar$^2$-b) | — |
| (I-7-59) | (I-7) | (Ar$^1$-c) | (Ar$^1$-d) | (Ar$^1$-b) | — | (Ar$^2$-b) | — |
| (I-7-60) | (I-7) | (Ar$^1$-d) | (Ar$^1$-d) | (Ar$^1$-b) | — | (Ar$^2$-b) | — |
| (I-7-61) | (I-7) | (Ar$^1$-a) | (Ar$^1$-a) | (Ar$^1$-c) | — | (Ar$^2$-b) | — |
| (I-7-62) | (I-7) | (Ar$^1$-a) | (Ar$^1$-b) | (Ar$^1$-c) | — | (Ar$^2$-b) | — |
| (I-7-63) | (I-7) | (Ar$^1$-a) | (Ar$^1$-c) | (Ar$^1$-c) | — | (Ar$^2$-b) | — |
| (I-7-64) | (I-7) | (Ar$^1$-a) | (Ar$^1$-d) | (Ar$^1$-c) | — | (Ar$^2$-b) | — |
| (I-7-65) | (I-7) | (Ar$^1$-b) | (Ar$^1$-b) | (Ar$^1$-c) | — | (Ar$^2$-b) | — |
| (I-7-66) | (I-7) | (Ar$^1$-b) | (Ar$^1$-c) | (Ar$^1$-c) | — | (Ar$^2$-b) | — |
| (I-7-67) | (I-7) | (Ar$^1$-b) | (Ar$^1$-d) | (Ar$^1$-c) | — | (Ar$^2$-b) | — |
| (I-7-68) | (I-7) | (Ar$^1$-c) | (Ar$^1$-c) | (Ar$^1$-c) | — | (Ar$^2$-b) | — |
| (I-7-69) | (I-7) | (Ar$^1$-c) | (Ar$^1$-d) | (Ar$^1$-c) | — | (Ar$^2$-b) | — |
| (I-7-70) | (I-7) | (Ar$^1$-d) | (Ar$^1$-d) | (Ar$^1$-c) | — | (Ar$^2$-b) | — |
| (I-7-71) | (I-7) | (Ar$^1$-a) | (Ar$^1$-a) | (Ar$^1$-d) | — | (Ar$^2$-b) | — |
| (I-7-72) | (I-7) | (Ar$^1$-a) | (Ar$^1$-b) | (Ar$^1$-d) | — | (Ar$^2$-b) | — |
| (I-7-73) | (I-7) | (Ar$^1$-a) | (Ar$^1$-c) | (Ar$^1$-d) | — | (Ar$^2$-b) | — |
| (I-7-74) | (I-7) | (Ar$^1$-a) | (Ar$^1$-d) | (Ar$^1$-d) | — | (Ar$^2$-b) | — |
| (I-7-75) | (I-7) | (Ar$^1$-b) | (Ar$^1$-b) | (Ar$^1$-d) | — | (Ar$^2$-b) | — |
| (I-7-76) | (I-7) | (Ar$^1$-b) | (Ar$^1$-c) | (Ar$^1$-d) | — | (Ar$^2$-b) | — |
| (I-7-77) | (I-7) | (Ar$^1$-b) | (Ar$^1$-d) | (Ar$^1$-d) | — | (Ar$^2$-b) | — |
| (I-7-78) | (I-7) | (Ar$^1$-c) | (Ar$^1$-c) | (Ar$^1$-d) | — | (Ar$^2$-b) | — |
| (I-7-79) | (I-7) | (Ar$^1$-c) | (Ar$^1$-d) | (Ar$^1$-d) | — | (Ar$^2$-b) | — |
| (I-7-80) | (I-7) | (Ar$^1$-d) | (Ar$^1$-d) | (Ar$^1$-d) | — | (Ar$^2$-b) | — |

The structures listed in the table may be substituted by any desired substituents, as defined above. They are preferably unsubstituted.

Examples of compounds according to the invention are depicted in the following table.

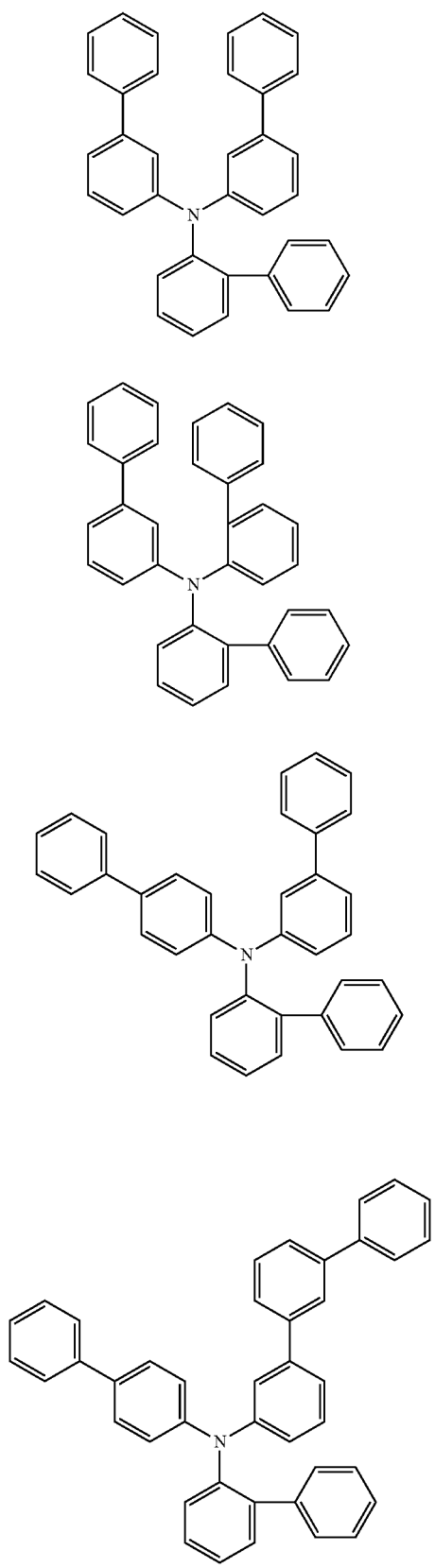
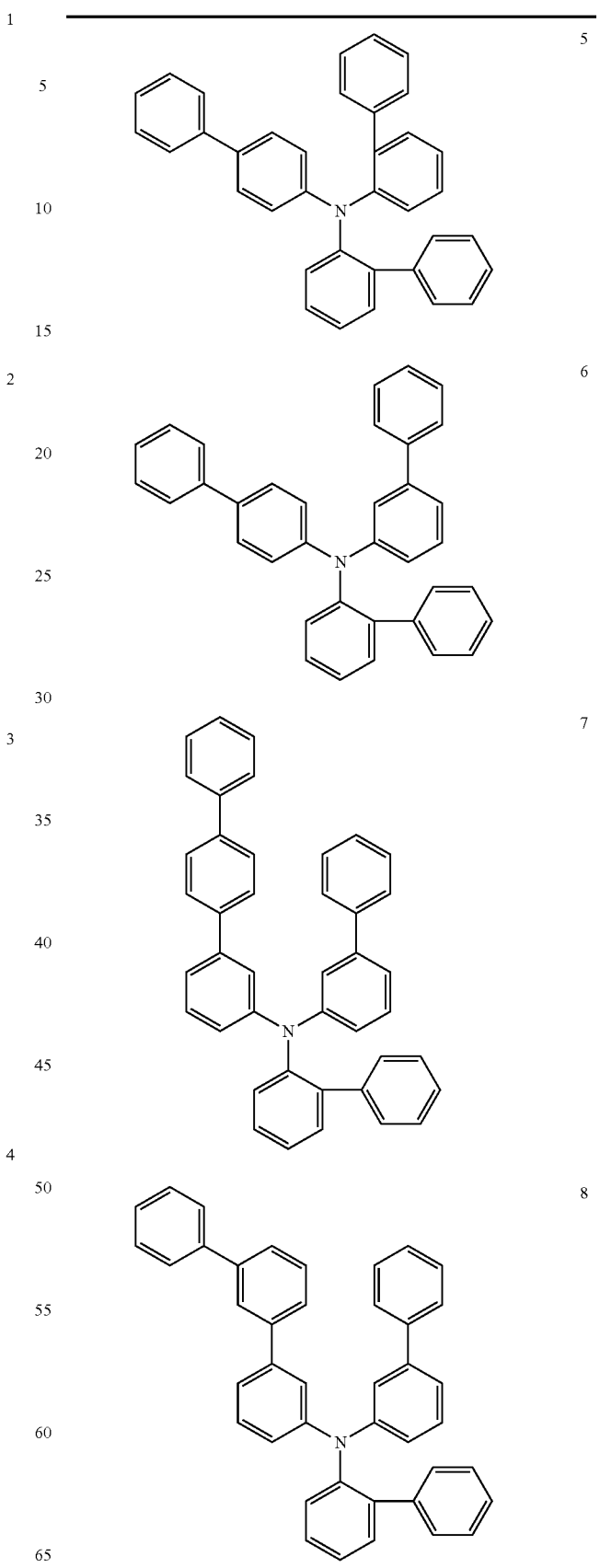

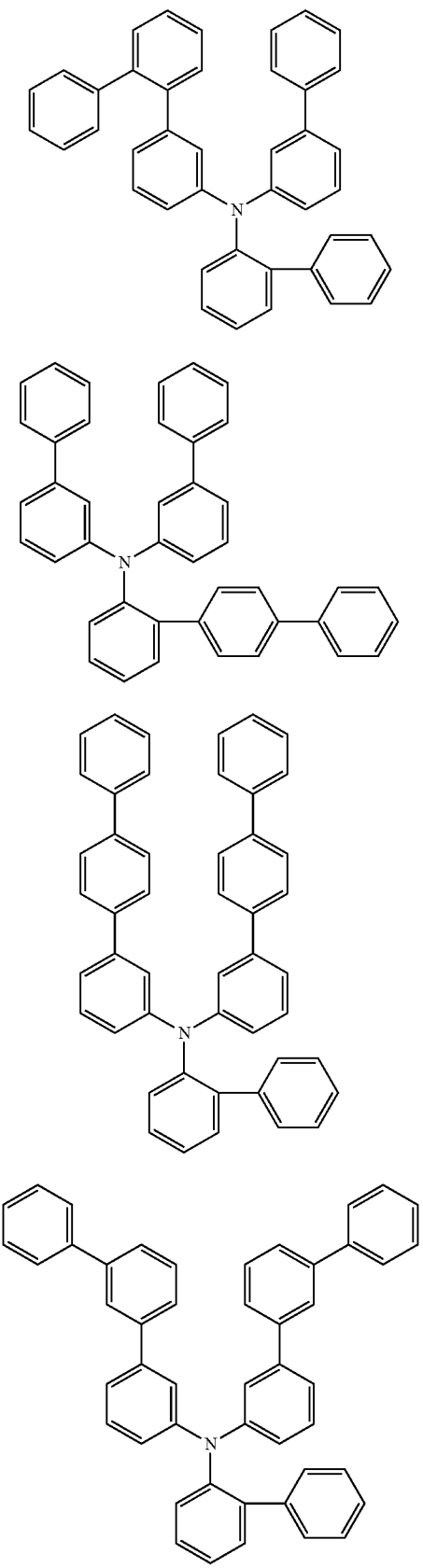
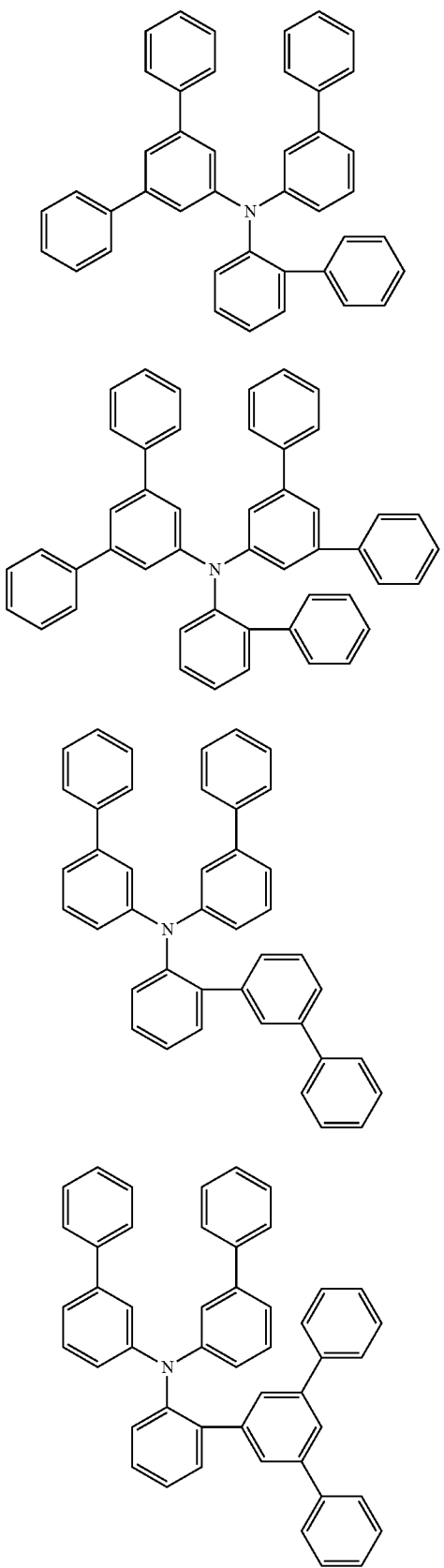

-continued
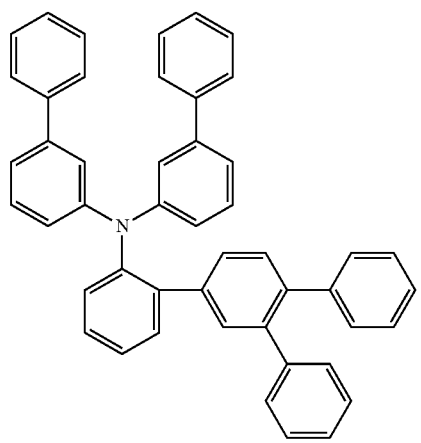 [SMILES: c1ccc(-c2cccc(N(c3cccc(-c4ccccc4)c3)c3ccccc3-c3ccc(-c4ccccc4)c(-c4ccccc4)c3)c2)cc1]
17
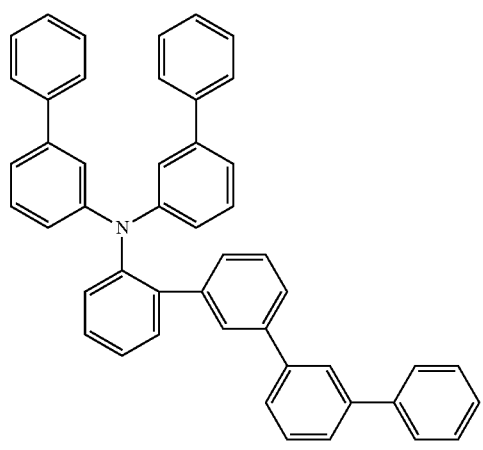 [SMILES: c1ccc(-c2cccc(-c3cccc(-c4ccccc4N(c4cccc(-c5ccccc5)c4)c4cccc(-c5ccccc5)c4)c3)c2)cc1]
18
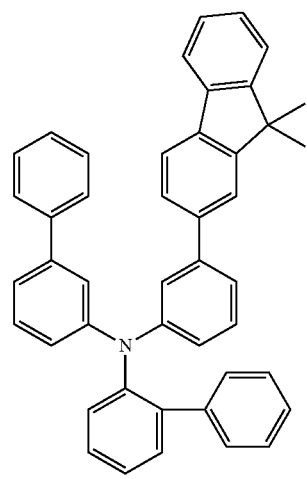 [SMILES: CC1(C)c2ccccc2-c2ccc(-c3cccc(N(c4cccc(-c5ccccc5)c4)c4ccccc4-c4ccccc4)c3)cc21]
19
-continued
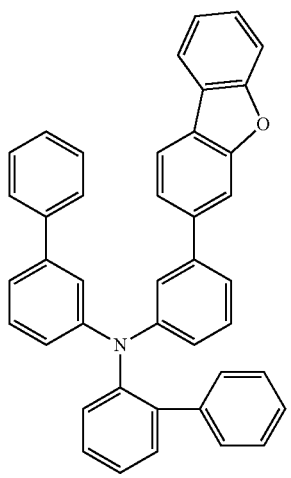 [SMILES: c1ccc(-c2cccc(N(c3cccc(-c4ccc5c(c4)oc4ccccc45)c3)c3ccccc3-c3ccccc3)c2)cc1]
20
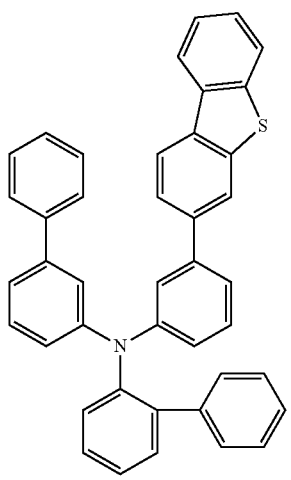 [SMILES: c1ccc(-c2cccc(N(c3cccc(-c4ccc5c(c4)sc4ccccc45)c3)c3ccccc3-c3ccccc3)c2)cc1]
21
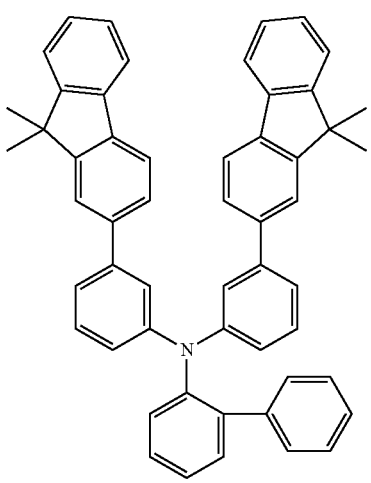
22

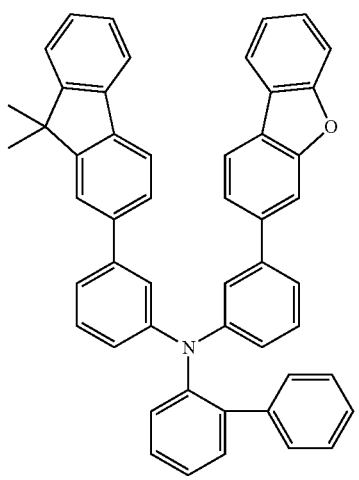 [SMILES: CC1(C)c2ccccc2-c2ccc(-c3cccc(N(c4cccc(-c5ccc6c(c5)oc5ccccc56)c4)c4ccccc4-c4ccccc4)c3)cc21]
23
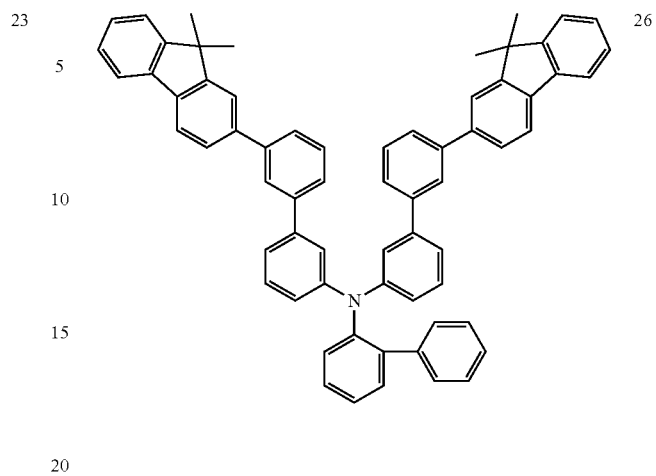
26
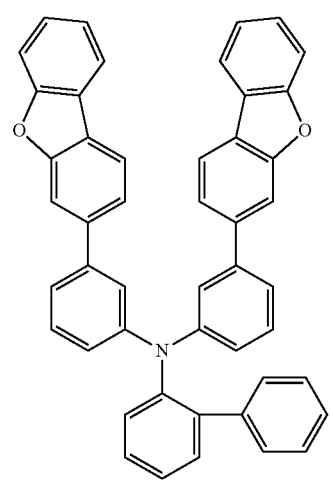 [SMILES: c1ccc(-c2ccccc2N(c2cccc(-c3ccc4c(c3)oc3ccccc34)c2)c2cccc(-c3ccc4c(c3)oc3ccccc34)c2)cc1]
24
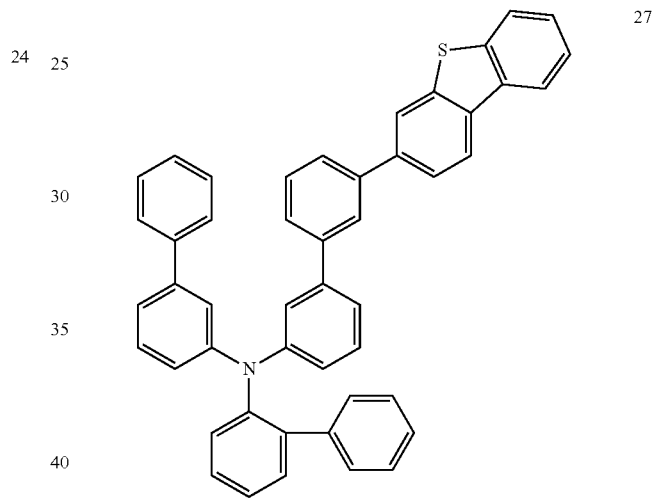
27
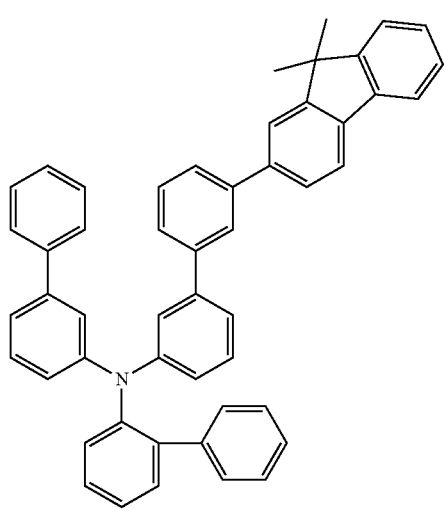 [SMILES: CC1(C)c2ccccc2-c2ccc(-c3cccc(-c4cccc(N(c5cccc(-c6ccccc6)c5)c5ccccc5-c5ccccc5)c4)c3)cc21]
25
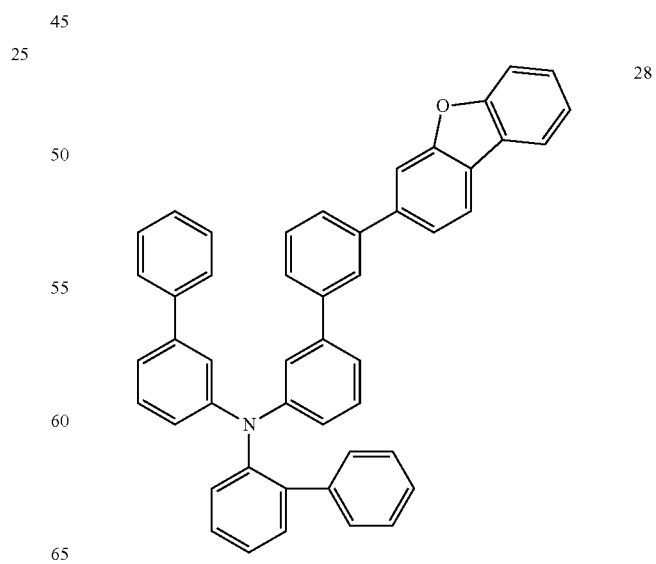
28

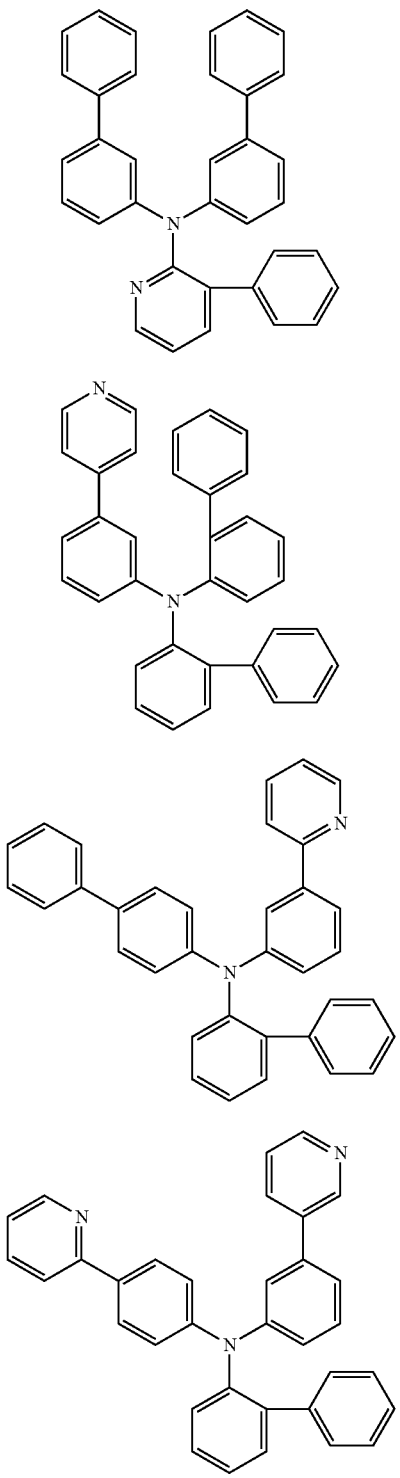

The compounds according to the invention can be synthesised by the process of organic preparative chemistry that is generally known to the person skilled in the art. Examples of reactions preferably employed are halogenations and transition-metal-catalysed coupling reactions, preferably Suzuki couplings and Buchwald couplings.

Two preferred routes for the preparation of the compounds according to the invention are depicted below.

Firstly, it is possible to prepare the compounds according to the invention starting from a primary aromatic amine, which is linked to two aryl groups in a coupling reaction (Scheme 1).

Scheme 1

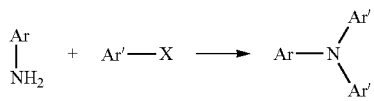

Ar here stands for an aromatic or heteroaromatic ring system, Ar' stands for an aromatic or heteroaromatic ring system and X stands for any desired leaving group, preferably a halide, such as Cl, Br or I, an alkyl- or arylsulfonate or diazonium.

The coupling reaction here is preferably a transition-metal-catalysed coupling reaction, for example a Hartwig-Buchwald coupling. An Ullmann reaction can also be used.

Alternatively, it is possible to prepare the compounds according to the invention starting from a secondary aromatic amine which carries two aryl groups and which is linked to an aryl group in a coupling reaction (Scheme 2).

Scheme 2

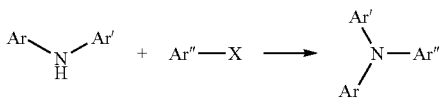

The symbols occurring are defined here as in Scheme 1, where Ar" represents an aromatic or heteroaromatic ring system. A coupling reaction as indicated for Scheme 1 is preferably used.

The reaction steps shown may be followed by further synthesis steps, for example for the introduction of substituents or for the modification of the basic structure.

The person skilled in the art will be able to select the process which is suitable for the respective present case from the two processes described above on the basis of his general expert knowledge, inter alia also depending on the commercial or synthetic availability of the starting compounds.

The present invention thus furthermore relates to a process for the preparation of a compound of the formula (I), characterised in that an aryl compound containing an amino group and an aryl compound containing a leaving group are linked to one another in a transition-metal-catalysed coupling reaction.

The leaving group here is preferably selected from Cl, Br, I, methylsulfonate, trifluoromethylsulfonate, phenylsulfonate, tolylsulfonate and diazonium.

The compounds according to the invention described above, in particular compounds which are substituted by reactive leaving groups, such as bromine, iodine, chlorine, boronic acid or boronic acid ester, can be used as monomers for the preparation of corresponding oligomers, dendrimers or polymers. Suitable reactive leaving groups are, for example, bromine, iodine, chlorine, boronic acids, boronic acid esters, amines, alkenyl or alkynyl groups containing a terminal C—C double or triple bond respectively, oxiranes, oxetanes, groups which undergo a cycloaddition, for example a 1,3-dipolar cycloaddition, such, as, for example, dienes or azides, carboxylic acid derivatives, alcohols and silanes.

The invention therefore furthermore relates to oligomers, polymers or dendrimers comprising one or more compounds of the formula (I), where the bond(s) to the polymer, oligomer or dendrimer may be localised at any desired positions in formula (I) which are substituted by $R^1$. Depending on the linking of the compound of the formula (I), the compound is part of a side chain of the oligomer or polymer or part of the main chain. An oligomer in the sense of this invention is taken to mean a compound which is built up from at least three monomer units. A polymer in the sense of the invention is taken to mean a compound which is built up from at least ten monomer units. The polymers, oligomers or dendrimers according to the invention may be conjugated, partially conjugated or non-conjugated. The oligomers or polymers according to the invention may be linear, branched or dendritic. In the structures linked in a linear manner, the units of the formula (I) may be linked directly to one another or linked to one another via a divalent group, for example via a substituted or unsubstituted alkylene group, via a heteroatom or via a divalent aromatic or heteroaromatic group. In branched and dendritic structures, three or more units of the formula (I) may, for example, be linked via a trivalent or polyvalent group, for example via a trivalent or polyvalent aromatic or heteroaromatic group, to give a branched or dendritic oligomer or polymer.

The same preferences as described above for compounds of the formula (I) apply to the recurring units of the formula (I) in oligomers, dendrimers and polymers.

For the preparation of the oligomers or polymers, the monomers according to the invention are homopolymerised or copolymerised with further monomers. Suitable and preferred comonomers are selected from fluorenes (for example in accordance with EP 842208 or WO 2000/22026), spirobifluorenes (for example in accordance with EP 707020, EP 894107 or WO 2006/061181), para-phenylenes (for example in accordance with WO 1992/18552), carbazoles (for example in accordance with WO 2004/070772 or WO 2004/113468), thiophenes (for example in accordance with EP 1028136), dihydrophenanthrenes (for example in accordance with WO 2005/014689 or WO 2007/006383), cis- and trans-indenofluorenes (for example in accordance with WO 2004/041901 or WO 2004/113412), ketones (for example in accordance with WO 2005/040302), phenanthrenes (for example in accordance with WO 2005/104264 or WO 2007/017066) or also a plurality of these units. The polymers, oligomers and dendrimers usually also contain further units, for example emitting (fluorescent or phosphorescent) units, such as, for example, vinyltriarylamines (for example in accordance with WO 2007/068325) or phosphorescent metal complexes (for example in accordance with WO 2006/003000), and/or charge-transport units, in particular those based on triarylamines.

The polymers, oligomers and dendrimers according to the invention have advantageous properties, in particular long lifetimes, high efficiencies and good colour coordinates.

The polymers and oligomers according to the invention are generally prepared by polymerisation of one or more types of monomer, at least one monomer of which results in recurring units of the formula (I) in the polymer. Suitable polymerisation reactions are known to the person skilled in the art and are described in the literature. Particularly suitable and preferred polymerisation reactions which result in C—C or C—N links are the following:

(A) SUZUKI polymerisation;
(B) YAMAMOTO polymerisation;
(C) STILLE polymerisation; and
(D) HARTWIG-BUCHWALD polymerisation.

The way in which the polymerisation can be carried out by these methods and the way in which the polymers can then be separated off from the reaction medium and purified is known to the person skilled in the art and is described in detail in the literature, for example in WO 2003/048225, WO 2004/037887 and WO 2004/037887.

The present invention thus also relates to a process for the preparation of the polymers, oligomers and dendrimers according to the invention, which is characterised in that they are prepared by SUZUKI polymerisation, YAMAMOTO polymerisation, STILLE polymerisation or HARTWIG-BUCHWALD polymerisation. The dendrimers according to the invention can be prepared by processes known to the person skilled in the art or analogously thereto. Suitable processes are described in the literature, such as, for example, in Frechet, Jean M. J.; Hawker, Craig J., "Hyperbranched polyphenylene and hyperbranched polyesters: new soluble, three-dimensional, reactive polymers", Reactive & Functional Polymers (1995), 26(1-3), 127-36; Janssen, H. M.; Meijer, E. W., "The synthesis and characterization of dendritic molecules", Materials Science and Technology (1999), 20 (Synthesis of Polymers), 403-458; Tomalia, Donald A., "Dendrimer molecules", Scientific American (1995), 272(5), 62-6; WO 2002/067343 A1 and WO 2005/026144 A1.

For the processing of the compounds according to the invention from the liquid phase, for example by spin coating or by printing processes, formulations of the compounds according to the invention are necessary. These formulations can be, for example, solutions, dispersions or miniemulsions. It may be preferred to use mixtures of two or more solvents for this purpose. Suitable and preferred solvents are, for example, toluene, anisole, o-, m- or p-xylene, methyl benzoate, dimethylanisole, mesitylene, tetralin, veratrol, THF, methyl-THF, THP, chlorobenzene, dioxane or mixtures of these solvents. It is preferred for the formulation comprising the mixture according to the invention to comprise one or more polymers, oligomers or dendrimers. The polymers, oligomers or dendrimers are preferably present in the formulation in a concentration of 1-80% by weight, particularly preferably 5-65% by weight and very particularly preferably 10-50% by weight. They serve, in particular, for setting the properties of the formulation, for example the viscosity. Preference is given to the use of polyarylamines, polystyrenes, polyacrylates and polyesters, in particular the use of the polymers disclosed in WO 2011/076325.

The invention therefore furthermore relates to a formulation, in particular a solution, dispersion or miniemulsion, comprising at least one compound of the formula (I) or at least one polymer, oligomer or dendrimer containing at least one unit of the formula (I), and at least one solvent, preferably an organic solvent. The way in which solutions of this type can be prepared is known to the person skilled in the art and is described, for example, in WO 2002/072714, WO 2003/019694 and the literature cited therein.

The compounds of the formula (I) according to the invention are suitable for use in electronic devices, in particular organic electroluminescent devices (OLEDs). Depending on the substitution, the compounds are employed in various functions and layers.

The invention therefore furthermore relates to the use of the compounds of the formula (I) in electronic devices and to electronic devices themselves which comprise one or more compounds of the formula (I). The electronic devices here are preferably selected from the group consisting of organic integrated circuits (OICs), organic field-effect transistors (OFETs), organic thin-film transistors (OTFTs), organic light-emitting transistors (OLETs), organic solar cells (OSCs), organic optical detectors, organic photoreceptors, organic field-quench devices (OFQDs), organic light-emitting electrochemical cells (OLECs), organic laser diodes (O-lasers) and particularly preferably organic electroluminescent devices (OLEDs).

The invention relates, as stated above, to electronic devices comprising at least one compound of the formula (I). The electronic devices here are preferably selected from the devices mentioned above. Particular preference is given to organic electroluminescent devices comprising anode, cathode and at least one emitting layer, characterised in that the device comprises at least one organic layer, which can be an emitting layer, a hole-transport layer or another layer, which comprises at least one compound of the formula (I).

Apart from cathode, anode and the emitting layer, the organic electroluminescent device may also comprise further layers. These are selected, for example, from in each case one or more hole-injection layers, hole-transport layers, hole-blocking layers, electron-transport layers, electron-injection layers, electron-blocking layers, exciton-blocking layers, inter-layers, charge-generation layers (IDMC 2003, Taiwan; Session 21 OLED (5), T. Matsumoto, T. Nakada, J. Endo, K. Mori, N. Kawamura, A. Yokoi, J. Kido, *Multiphoton Organic EL Device Having Charge Generation Layer*) and/or organic or inorganic p/n junctions. However, it should be pointed out that each of these layers does not necessarily have to be present and the choice of layers is always dependent on the compounds used and in particular also on whether the electroluminescent device is fluorescent or phosphorescent.

The organic electroluminescent device according to the invention may comprise a plurality of emitting layers. In this case, these emission layers particularly preferably have in total a plurality of emission maxima between 380 nm and 750 nm, resulting overall in white emission, i.e. various emitting compounds which are able to fluoresce or phosphoresce and which emit blue or yellow or orange or red light are used in the emitting layers. Particular preference is given to three-layer systems, i.e. systems having three emitting layers, where the three layers exhibit blue, green and orange or red emission (for the basic structure see, for example, WO 2005/011013). The compounds according to the invention may be present in a hole-transport layer, an emitting layer and/or in another layer in such devices. It should be noted that, for the generation of white light, an emitter compound used individually which emits in a broad wavelength range may also be suitable instead of a plurality of emitter compounds emitting in colour.

It is preferred in accordance with the invention for the compound of the formula (I) to be employed in an electronic device comprising one or more phosphorescent dopants. The compound here can be used in various layers, preferably in a hole-transport layer, a hole-injection layer or in an emitting layer. However, the compound of the formula (I) can also be employed in accordance with the invention in an electronic device comprising one or more fluorescent dopants.

The term phosphorescent dopants typically encompasses compounds in which the light emission takes place through a spin-forbidden transition, for example a transition from an excited triplet state or a state having a relatively high spin quantum number, for example a quintet state.

Suitable phosphorescent dopants (=triplet emitters) are, in particular, compounds which emit light, preferably in the visible region, on suitable excitation and in addition contain at least one atom having an atomic number greater than 20, preferably greater than 38 and less than 84, particularly preferably greater than 56 and less than 80. The phosphorescent emitters used are preferably compounds which contain copper, molybdenum, tungsten, rhenium, ruthenium, osmium, rhodium, iridium, palladium, platinum, silver, gold or europium, in particular compounds which contain iridium, platinum or copper.

All luminescent iridium, platinum or copper complexes are regarded as phosphorescent compounds in the sense of the present invention.

Examples of the emitters described above are revealed by the applications WO 00/70655, WO 01/41512, WO 02/02714, WO 02/15645, EP 1191613, EP 1191612, EP 1191614, WO 05/033244, WO 05/019373 and US 2005/0258742. In general, all phosphorescent complexes as are used in accordance with the prior art for phosphorescent OLEDs and as are known to the person skilled in the art in the area of organic electroluminescent devices are suitable. The person skilled in the art will also be able, without inventive step, to employ further phosphorescent complexes in combination with the compounds of the formula (I) in organic electroluminescent devices.

Explicit examples of suitable phosphorescent emitter compounds are furthermore revealed by the following table.

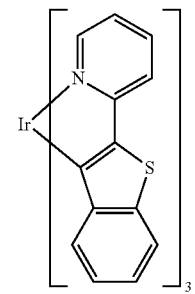

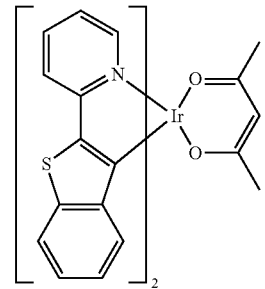

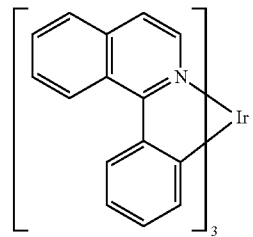

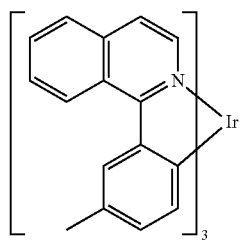
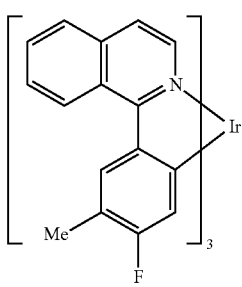
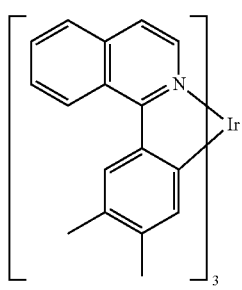
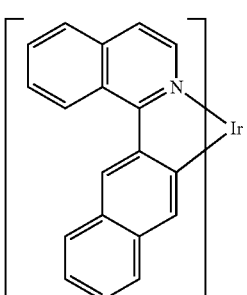
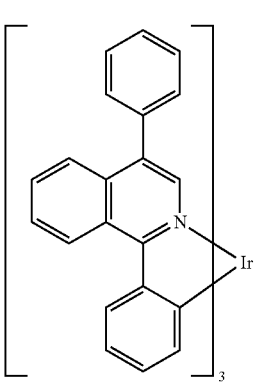
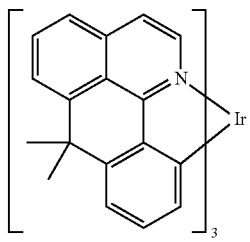
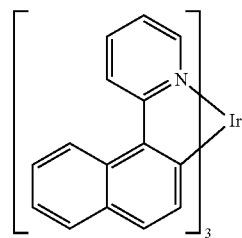
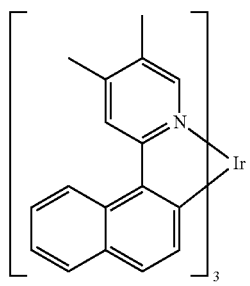
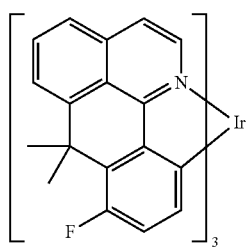
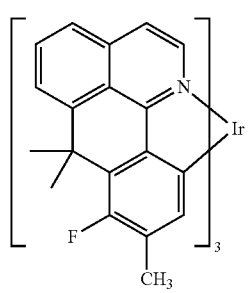
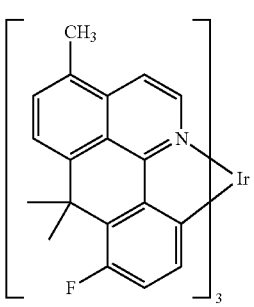

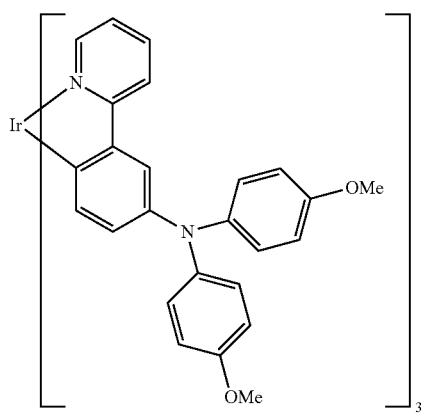
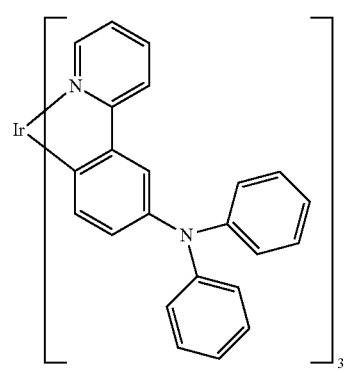
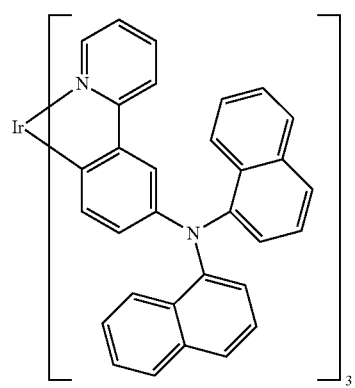
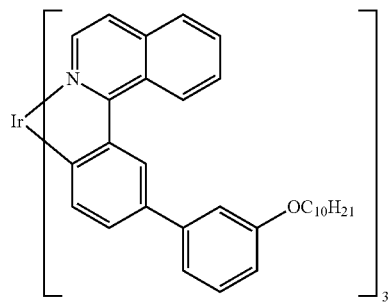
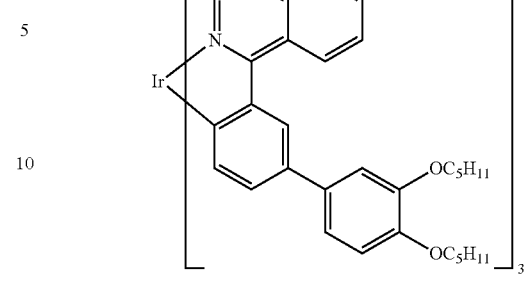
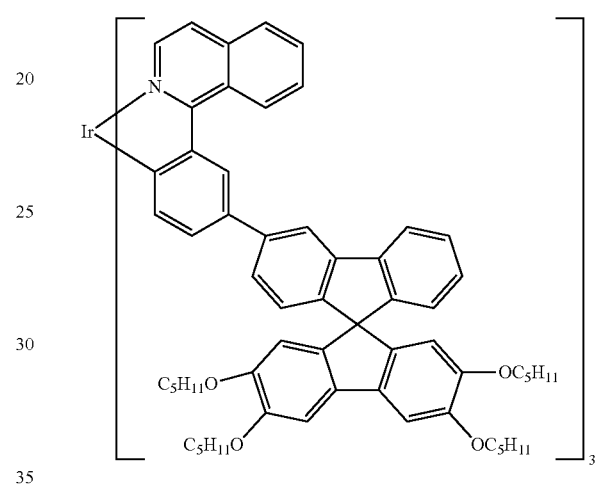
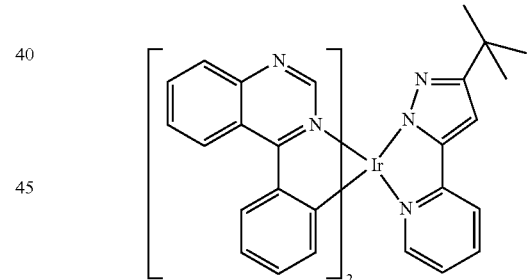
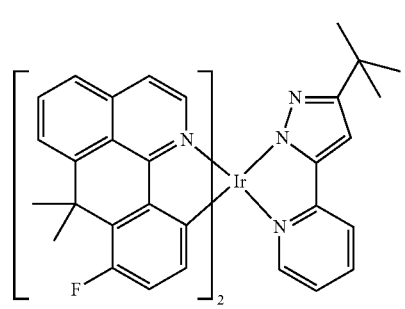

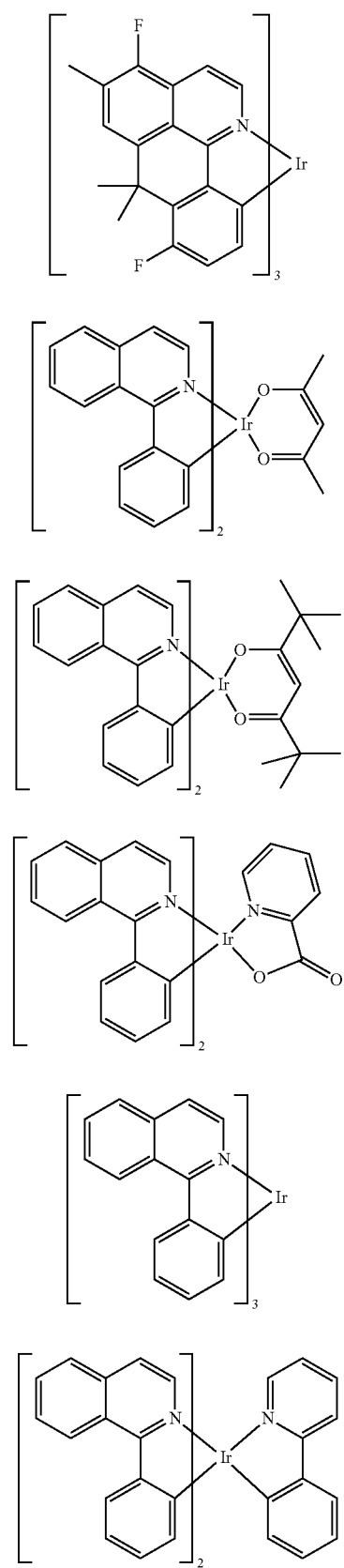
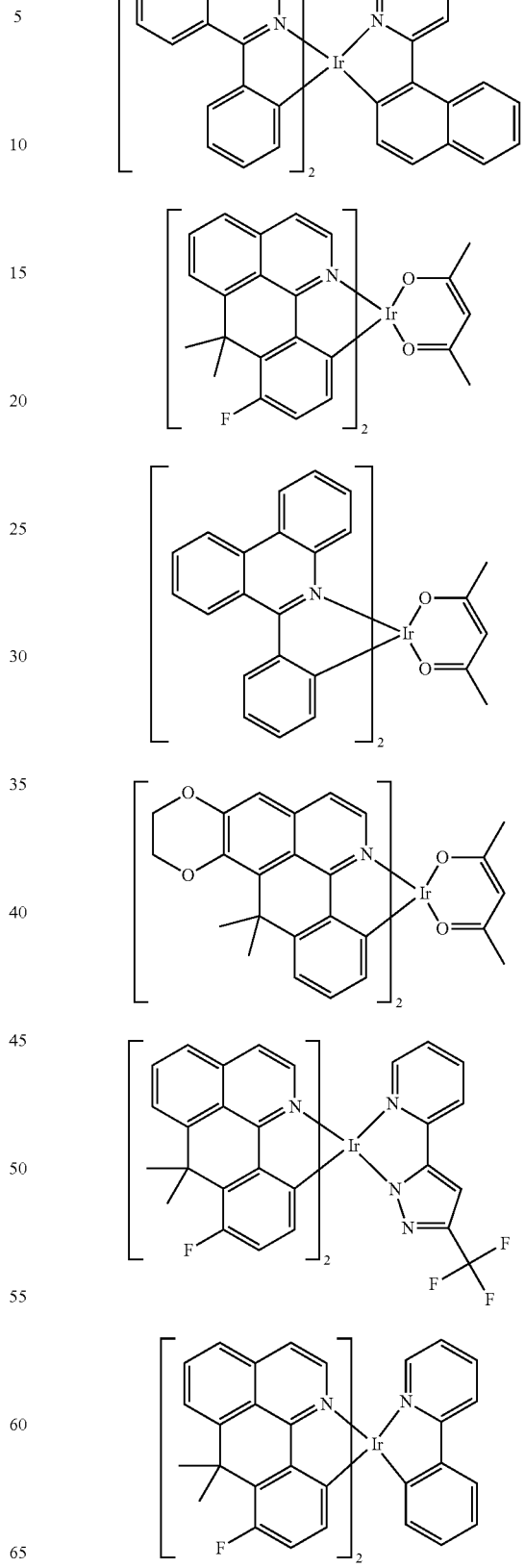

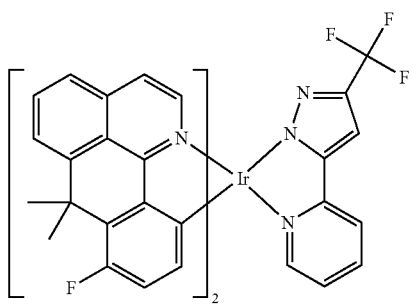
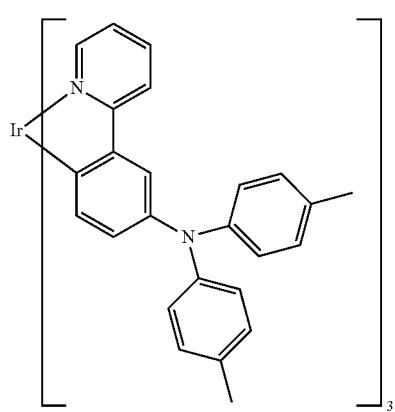
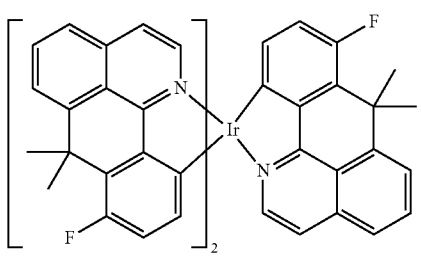
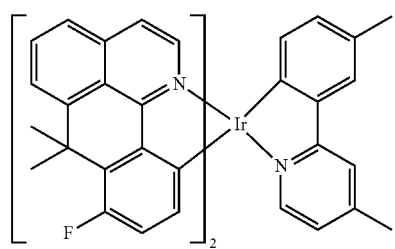
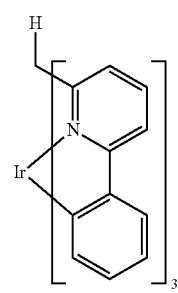
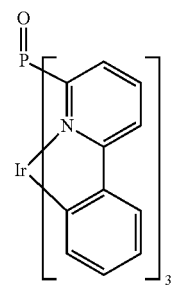
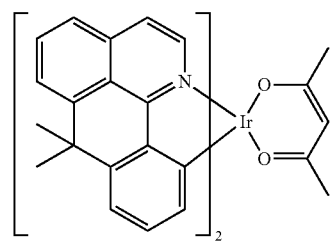
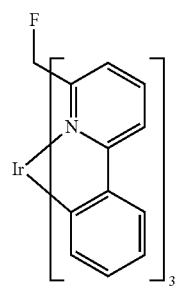
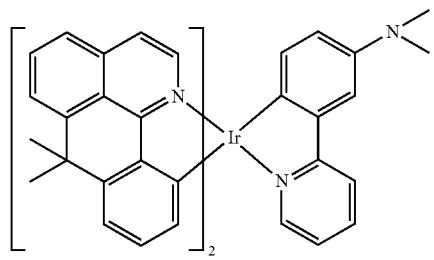
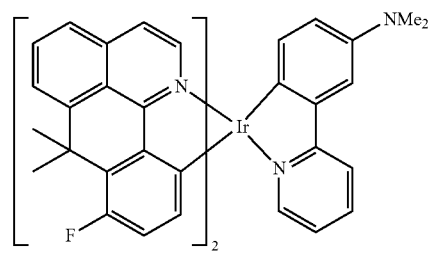
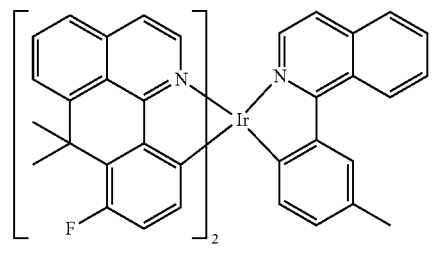

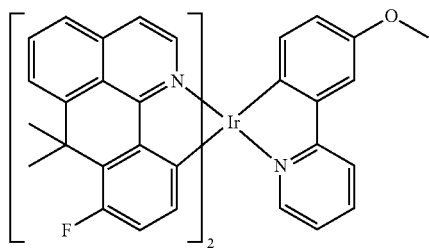
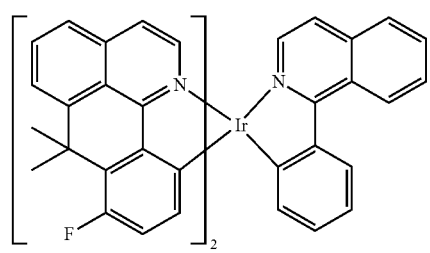
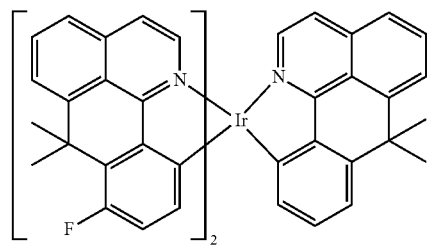
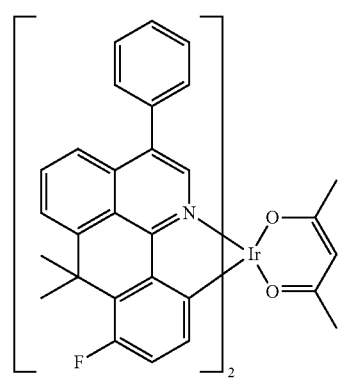
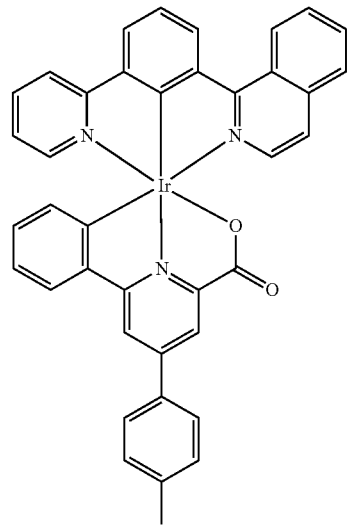
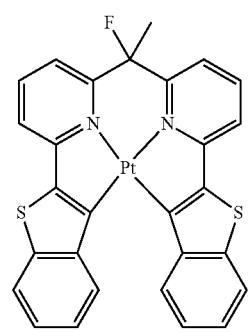
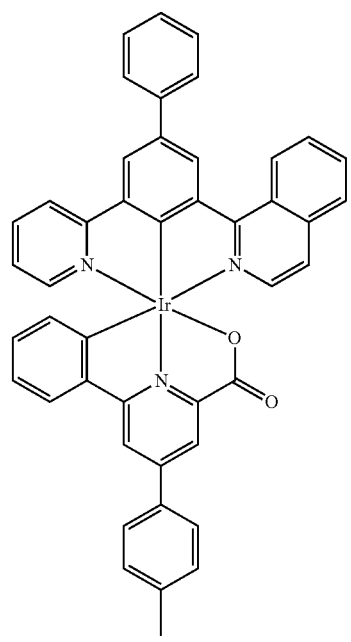

47
-continued
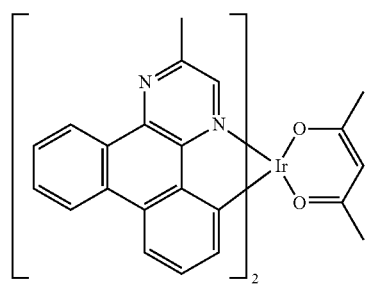
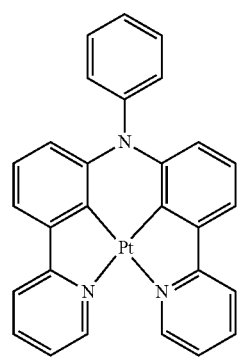
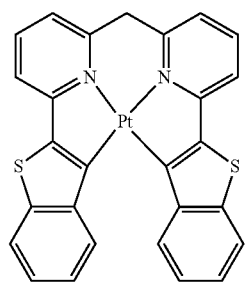
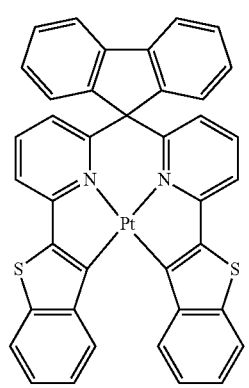
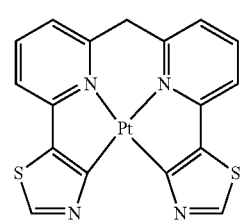
48
-continued
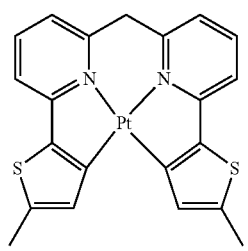
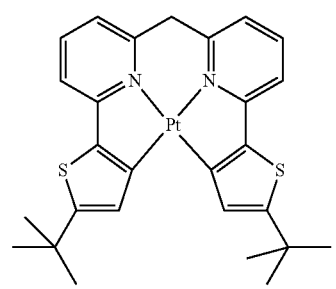
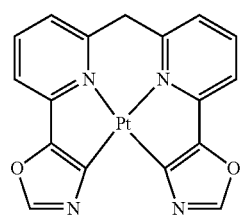
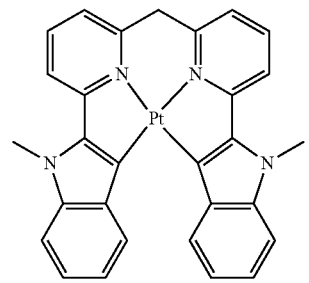
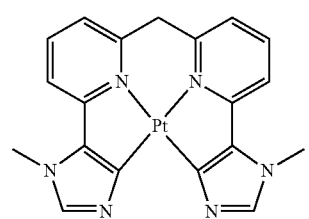

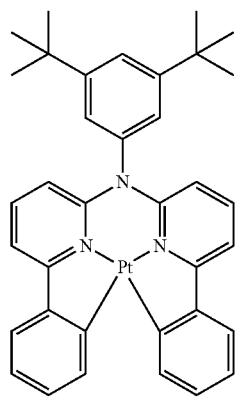
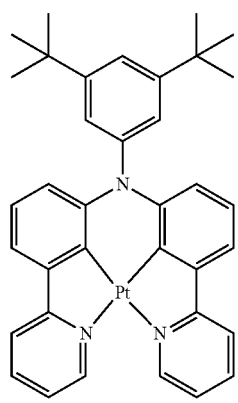
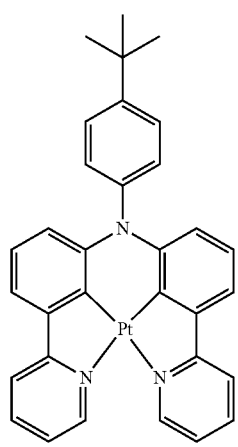
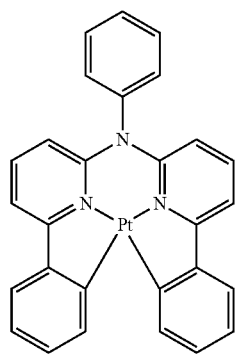
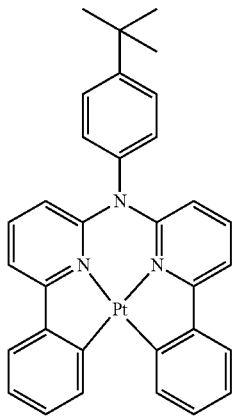
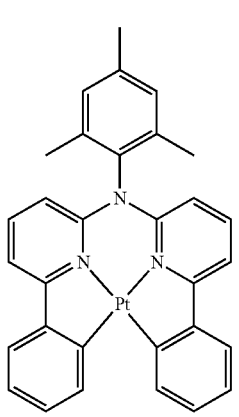
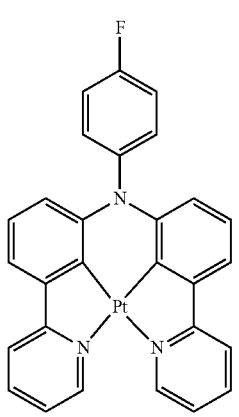
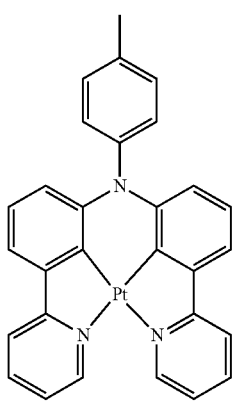

51
-continued
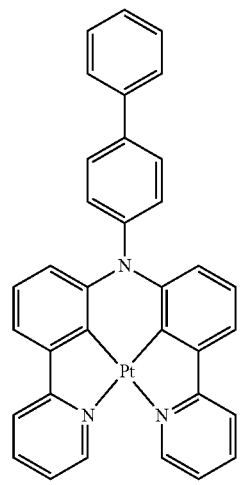
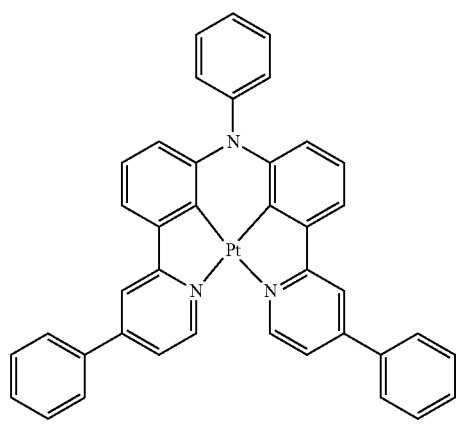
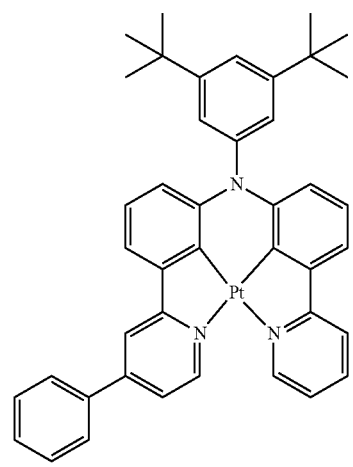
52
-continued
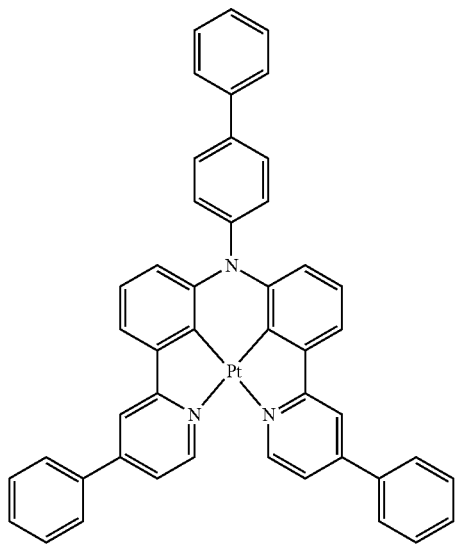
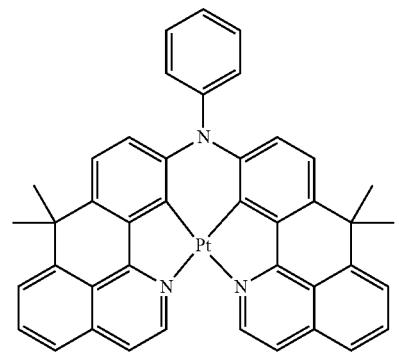
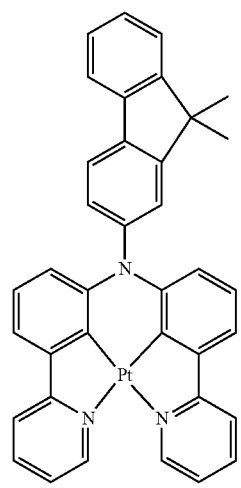

53
-continued
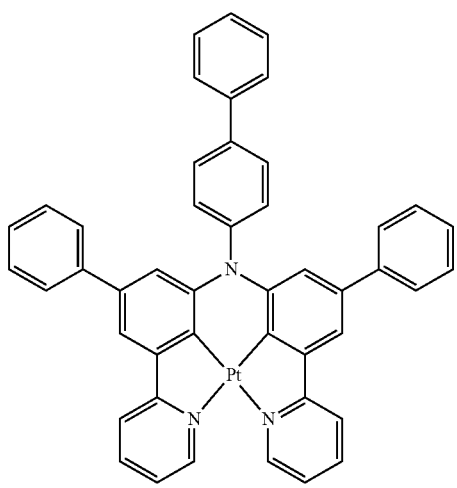
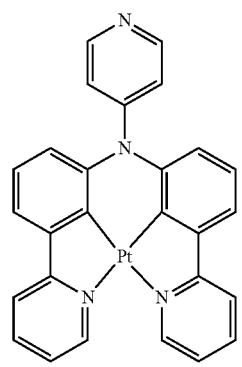
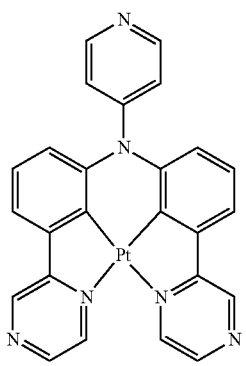
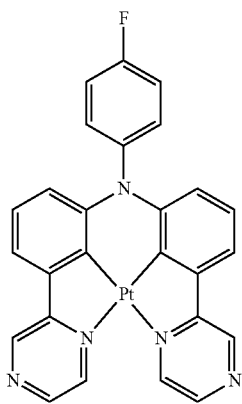
54
-continued
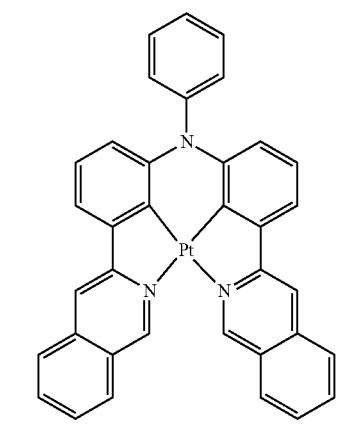
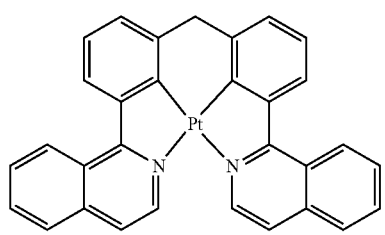
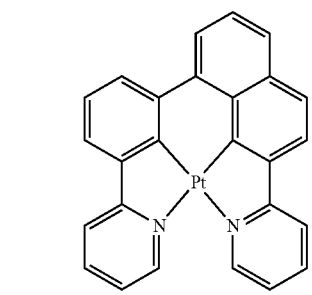
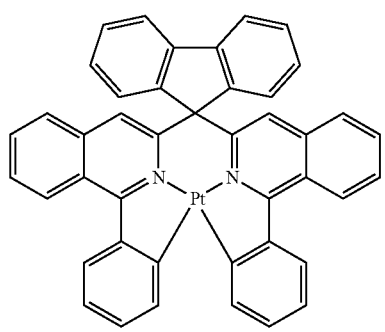
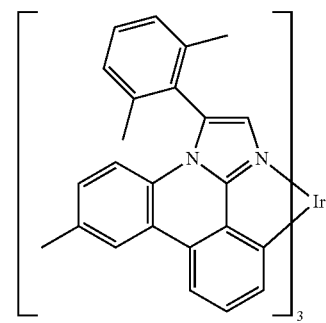

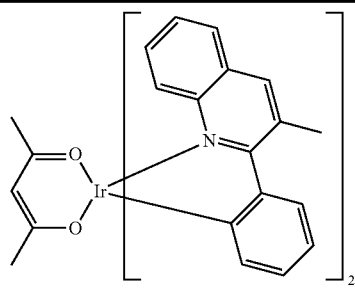
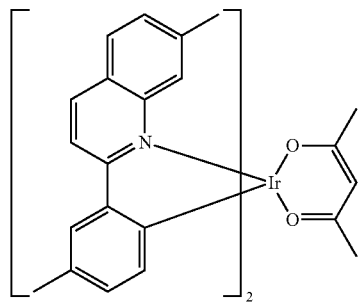
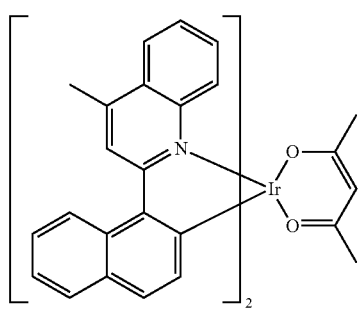
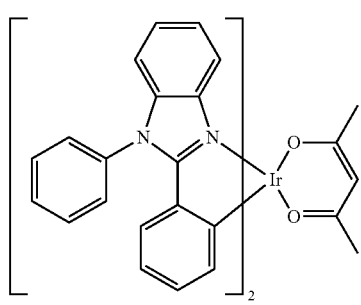
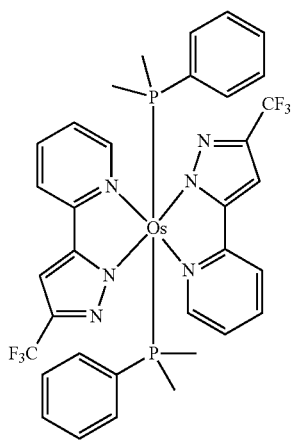
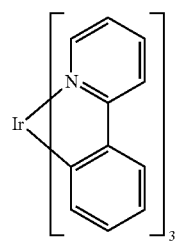
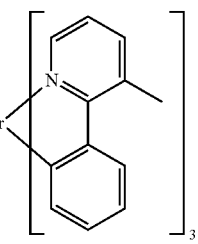
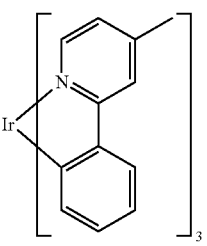
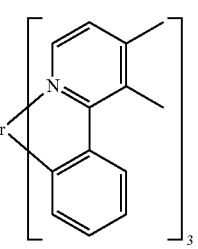

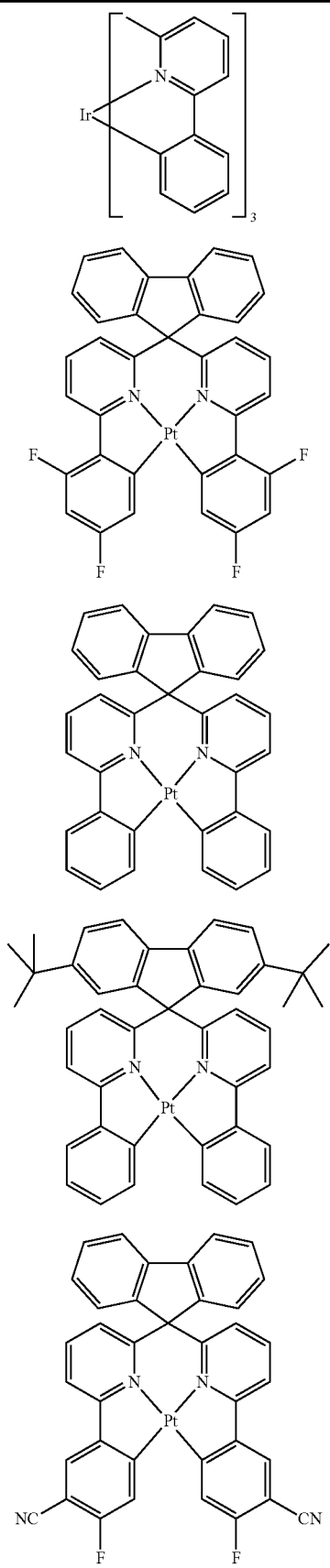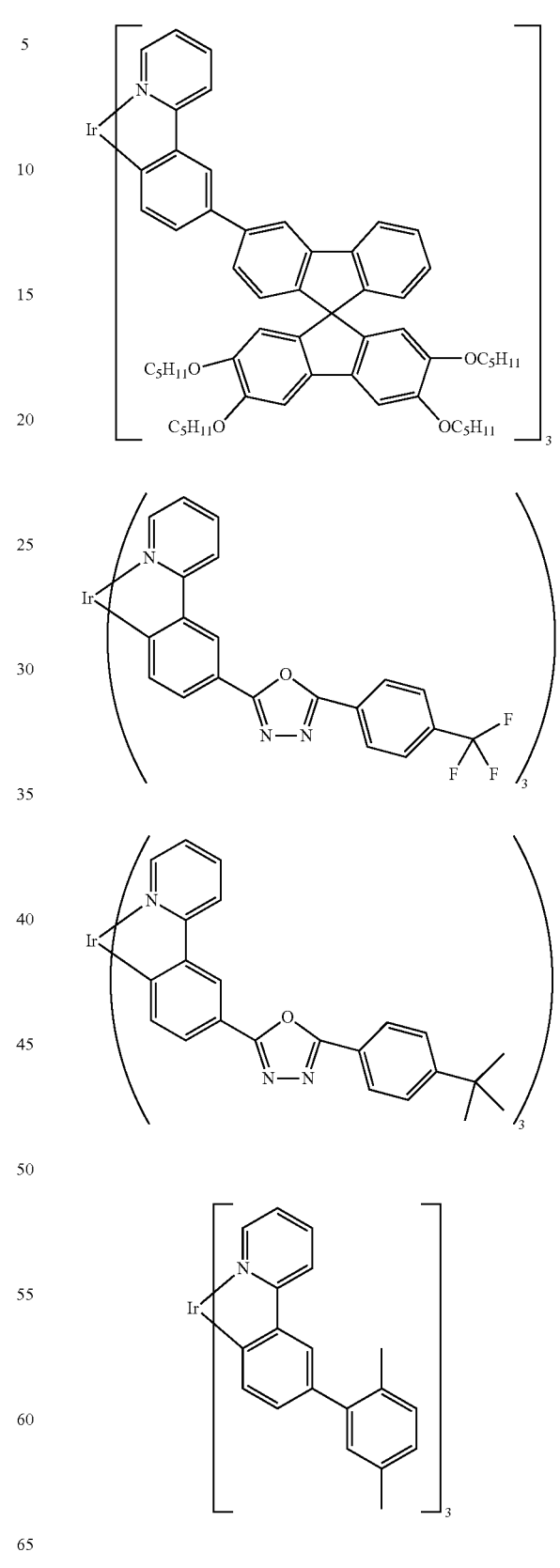

-continued
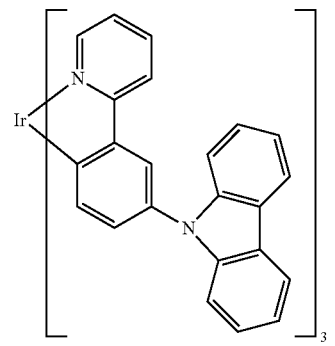
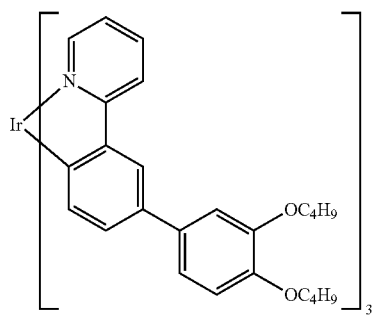
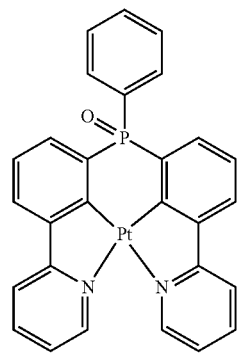
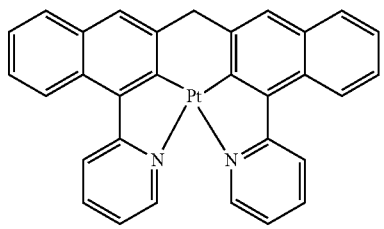
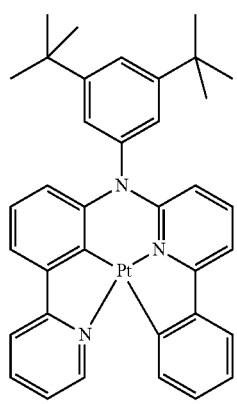
-continued
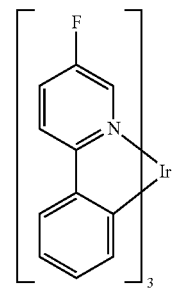
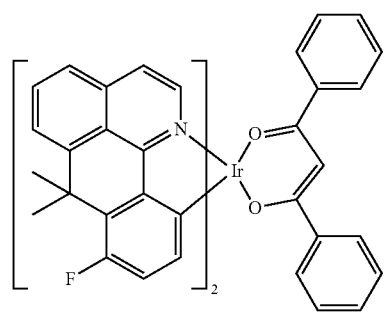
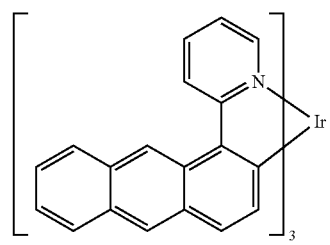
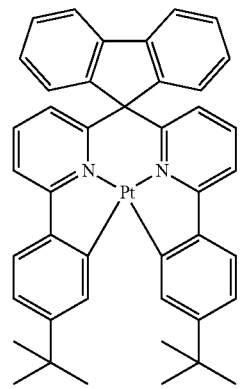
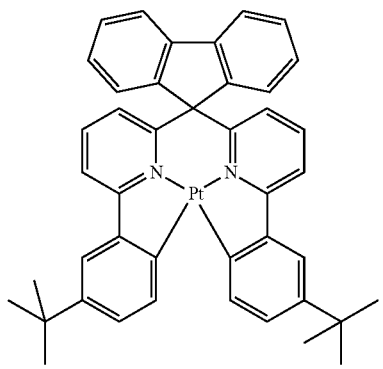

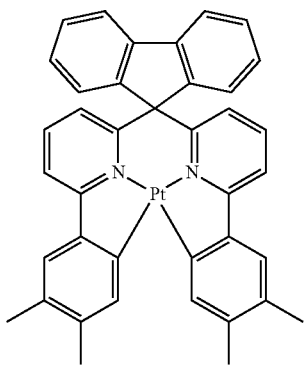
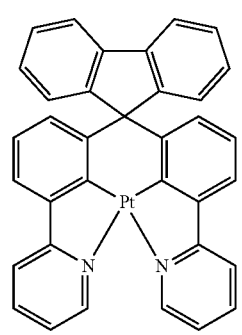
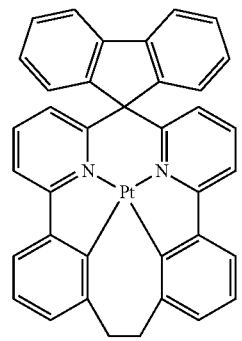
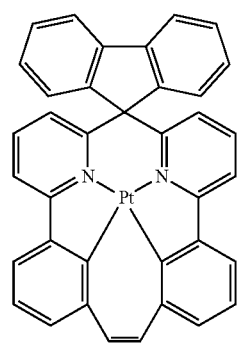
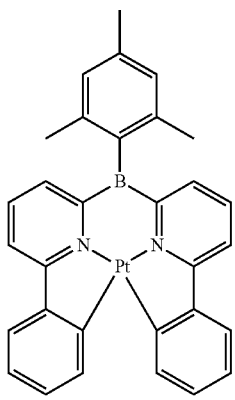
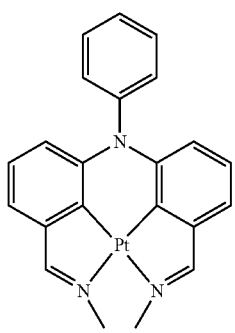
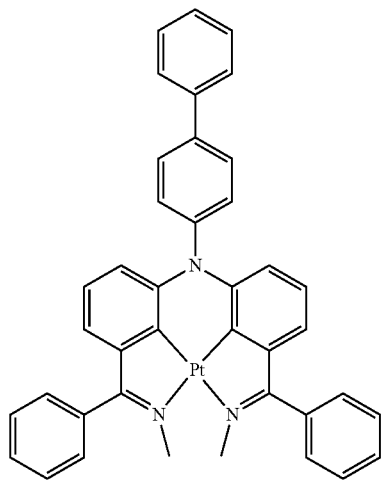
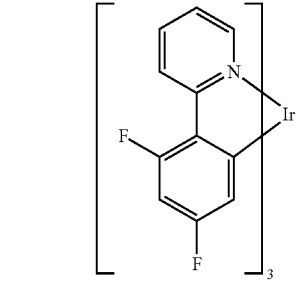

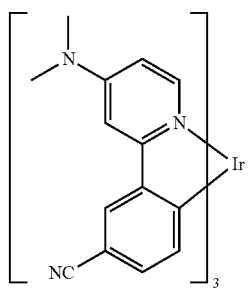
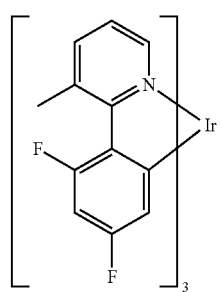
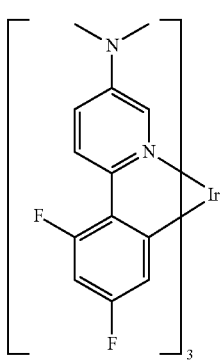
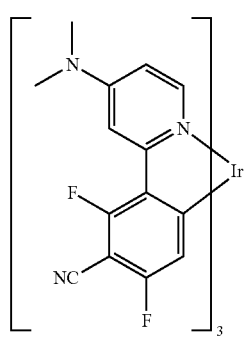
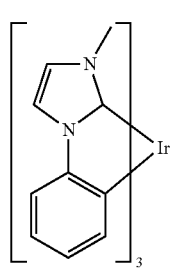
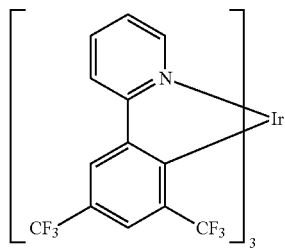
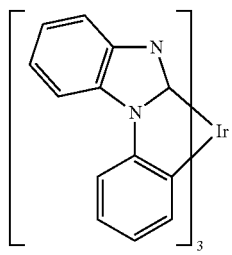
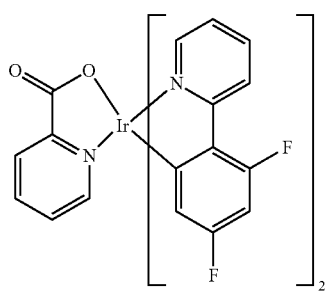
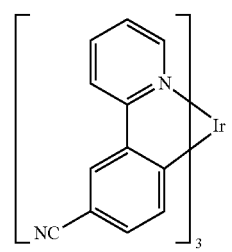
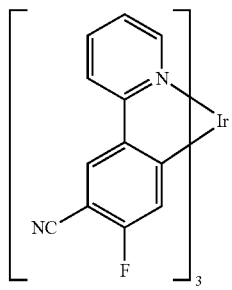
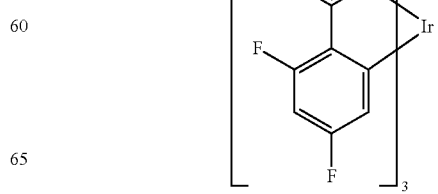

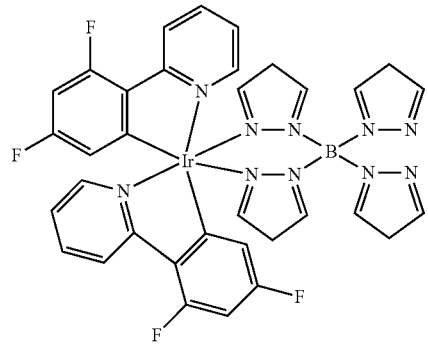
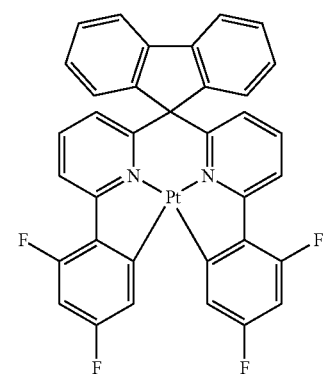
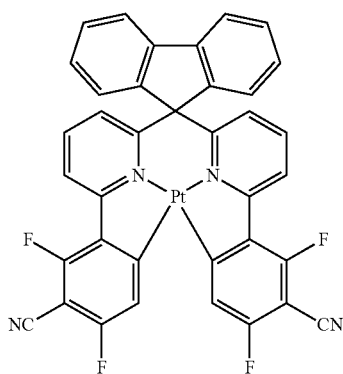
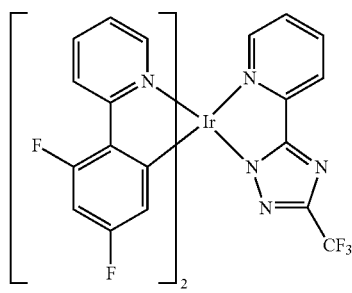
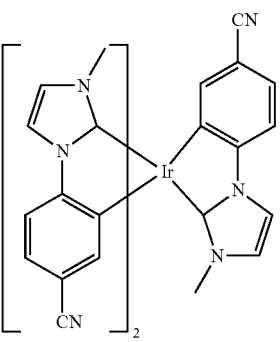
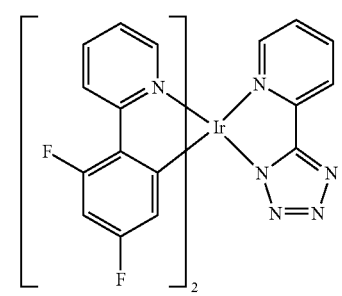
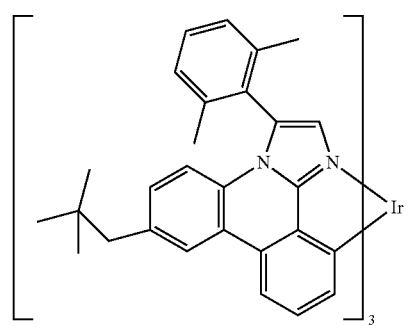
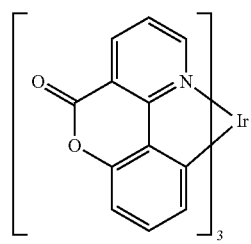
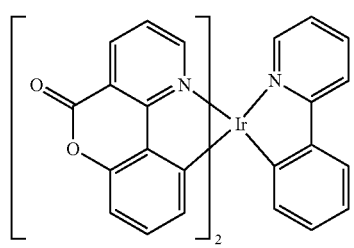

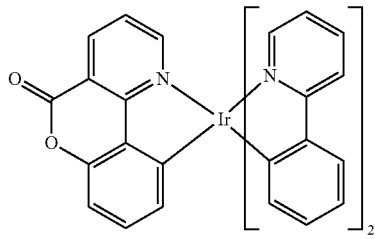

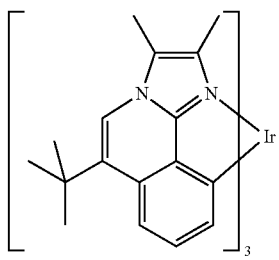

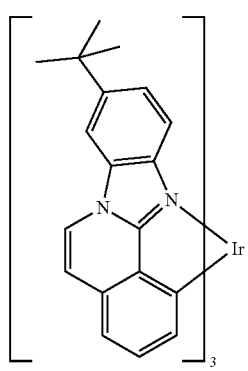

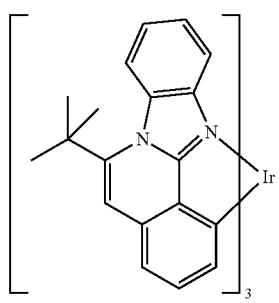

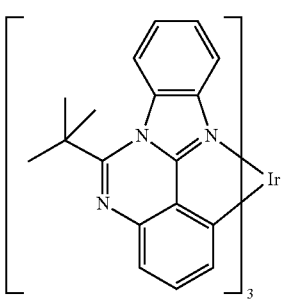

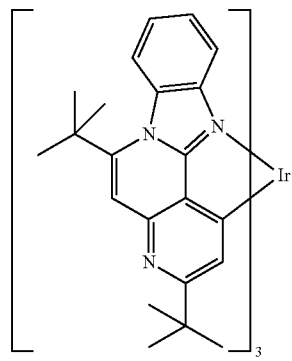

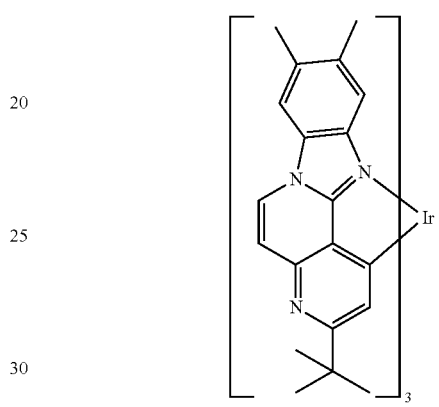

In a preferred embodiment of the invention, the compounds of the formula (I) are employed as hole-transport material. The compounds are correspondingly preferably employed in a hole-transport layer, a hole-injection layer and/or an electron-blocking layer.

A hole-injection layer in the sense of this invention is a layer which is directly adjacent to the anode. A hole-transport layer in the sense of this invention is a layer which is located between the hole-injection layer and the emission layer. The hole-transport layer may be directly adjacent to the emission layer. An electron-blocking layer in the sense of this invention is a layer which is directly adjacent to the emission layer on the anode side. In particular, an electron-blocking layer is taken to mean a layer which is directly adjacent to the emission layer on the anode side, where one or more hole-transport layers are additionally present on the anode side of the electron-blocking layer. The hole-injection layer, hole-transport layer and electron-blocking layer preferably each comprise materials having hole-transporting properties. For use in the electron-blocking layer, it is particularly preferred for the compound to have a high LUMO.

In a further embodiment of the present invention, the compounds of the formula (I) are employed as matrix material in combination with one or more fluorescent or phosphorescent dopants.

A dopant in a system comprising a matrix material and a dopant is taken to mean the component whose proportion in the mixture is the smaller. Correspondingly, a matrix material in a system comprising a matrix material and a dopant is taken to mean the component whose proportion in the mixture is the larger.

The proportion of the matrix material in the emitting layer in this case is between 50.0 and 99.9% by vol., preferably between 80.0 and 99.5% by vol. and particularly preferably between 92.0 and 99.5% by vol. for fluorescent emitting layers and between 85.0 and 97.0% by vol. for phosphorescent emitting layers.

Correspondingly, the proportion of the dopant is between 0.1 and 50.0% by vol., preferably between 0.5 and 20.0% by vol. and particularly preferably between 0.5 and 8.0% by vol. for fluorescent emitting layers and between 3.0 and 15.0% by vol. for phosphorescent emitting layers.

The materials preferably employed in the relevant functions in the devices according to the invention are described below.

Preferred fluorescent dopants are selected from the class of the arylamines. An arylamine or aromatic amine in the sense of this invention is taken to mean a compound which contains three substituted or unsubstituted aromatic or heteroaromatic ring systems bonded directly to the nitrogen. At least one of these aromatic or heteroaromatic ring systems is preferably a condensed ring system, particularly preferably having at least 14 aromatic ring atoms. Preferred examples thereof are aromatic anthracenamines, aromatic anthracenediamines, aromatic pyrenamines, aromatic pyrenediamines, aromatic chrysenamines or aromatic chrysenediamines. An aromatic anthracenamine is taken to mean a compound in which one diarylamino group is bonded directly to an anthracene group, preferably in the 9-position. An aromatic anthracenediamine is taken to mean a compound in which two diarylamino groups are bonded directly to an anthracene group, preferably in the 9,10-position. Aromatic pyrenamines, pyrenediamines, chrysenamines and chrysenediamines are defined analogously thereto, where the diarylamino groups are preferably bonded to the pyrene in the 1-position or in the 1,6-position.

Suitable matrix materials, preferably for fluorescent dopants, besides the compounds according to the invention, are materials from various classes of substance. Preferred matrix materials are selected from the classes of the oligoarylenes (for example 2,2',7,7'-tetraphenylspirobifluorene in accordance with EP 676461 or dinaphthylanthracene), in particular the oligoarylenes containing condensed aromatic groups, the oligoarylenevinylenes (for example DPVBi or spiro-DPVBi in accordance with EP 676461), the polypodal metal complexes (for example in accordance with WO 2004/081017), the hole-conducting compounds (for example in accordance with WO 2004/058911), the electron-conducting compounds, in particular ketones, phosphine oxides, sulfoxides, etc. (for example in accordance with WO 2005/084081 and WO 2005/084082), the atropisomers (for example in accordance with WO 2006/048268), the boronic acid derivatives (for example in accordance with WO 2006/117052) or the benzanthracenes (for example in accordance with WO 2008/145239). Particularly preferred matrix materials are selected from the classes of the oligoarylenes, comprising naphthalene, anthracene, benzanthracene and/or pyrene or atropisomers of these compounds, the oligoarylenevinylenes, the ketones, the phosphine oxides and the sulfoxides. Very particularly preferred matrix materials are selected from the classes of the oligoarylenes, comprising anthracene, benzanthracene, benzophenanthrene and/or pyrene or atropisomers of these compounds. An oligoarylene in the sense of this invention is intended to be taken to mean a compound in which at least three aryl or arylene groups are bonded to one another.

Preferred matrix materials for phosphorescent dopnats, besides the compounds according to the invention, are aromatic amines, in particular triarylamines, for example in accordance with US 2005/0069729, carbazole derivatives (for example CBP, N,N-biscarbazolylbiphenyl) or compounds in accordance with WO 2005/039246, US 2005/0069729, JP 2004/288381, EP 1205527 or WO 2008/086851, bridged carbazole derivatives, for example in accordance with WO 2011/088877 and WO 2011/128017, indenocarbazole derivatives, for example in accordance with WO 2010/136109 and WO 2011/000455, azacarbazole derivatives, for example in accordance with EP 1617710, EP 1617711, EP 1731584, JP 2005/347160, indolocarbazole derivatives, for example in accordance with WO 2007/063754 or WO 2008/056746, ketones, for example in accordance with WO 2004/093207 or WO 2010/006680, phosphine oxides, sulfoxides and sulfones, for example in accordance with WO 2005/003253, oligophenylenes, bipolar matrix materials, for example in accordance with WO 2007/137725, silanes, for example in accordance with WO 2005/111172, azaboroles or boronic esters, for example in accordance with WO 2006/117052, triazine derivatives, for example in accordance with WO 2010/015306, WO 2007/063754 or WO 2008/056746, zinc complexes, for example in accordance with EP 652273 or WO 2009/062578, aluminium complexes, for example BAlq, diazasilole and tetraazasilole derivatives, for example in accordance with WO 2010/054729, diazaphosphole derivatives, for example in accordance with WO 2010/054730, and aluminium complexes, for example BAIQ.

Suitable charge-transport materials, as can be used in the hole-injection or hole-transport layer or in the electron-transport layer of the organic electroluminescent device according to the invention, are, for example, the compounds disclosed in Y. Shirota et al., Chem. Rev. 2007, 107(4), 953-1010, or other materials as are employed in these layers in accordance with the prior art.

The cathode of the organic electroluminescent device preferably comprises metals having a low work function, metal alloys or multilayered structures comprising various metals, such as, for example, alkaline-earth metals, alkali metals, main-group metals or lanthanoids (for example Ca, Ba, Mg, Al, In, Mg, Yb, Sm, etc.). Also suitable are alloys comprising an alkali metal or alkaline-earth metal and silver, for example an alloy comprising magnesium and silver. In the case of multilayered structures, further metals which have a relatively high work function, such as, for example, Ag or Al, can also be used in addition to the said metals, in which case combinations of the metals, such as, for example, Ca/Ag, Mg/Ag or Ag/Ag, are generally used. It may also be preferred to introduce a thin interlayer of a material having a high dielectric constant between a metallic cathode and the organic semiconductor. Suitable for this purpose are, for example, alkali metal fluorides or alkaline-earth metal fluorides, but also the corresponding oxides or carbonates (for example LiF, $Li_2O$, $BaF_2$, MgO, NaF, CsF, $Cs_2CO_3$, etc.). Furthermore, lithium quinolinate (LiQ) can be used for this purpose. The layer thickness of this layer is preferably between 0.5 and 5 nm.

The anode preferably comprises materials having a high work function. The anode preferably has a work function of greater than 4.5 eV vs. vacuum. Suitable for this purpose are on the one hand metals having a high redox potential, such as, for example, Ag, Pt or Au. On the other hand, metal/metal oxide electrodes (for example $Al/Ni/NiO_x$, $Al/PtO_x$) may also be preferred. For some applications, at least one of the electrodes must be transparent or partially transparent in order to facilitate either irradiation of the organic material (organic solar cells) or the coupling-out of light (OLEDs, O-lasers). Preferred anode materials here are conductive mixed metal oxides. Particular preference is given to indium tin oxide (ITO) or indium zinc oxide (IZO). Preference is furthermore given to conductive, doped organic materials, in particular conductive, doped polymers.

The device is appropriately (depending on the application) structured, provided with contacts and finally sealed, since the lifetime of the devices according to the invention is shortened in the presence of water and/or air.

In a preferred embodiment, the organic electroluminescent device according to the invention is characterised in that one or more layers are coated by means of a sublimation process, in which the materials are applied by vapour deposition in vacuum sublimation units at an initial pressure of less than $10^{-5}$ mbar, preferably less than $10^{-6}$ mbar. However, it is also possible here for the initial pressure to be even lower, for example less than $10^{-7}$ mbar.

Preference is likewise given to an organic electroluminescent device, characterised in that one or more layers are coated by means of the OVPD (organic vapour phase deposition) process or with the aid of carrier-gas sublimation, in which the materials are applied at a pressure of between $10^{-5}$ mbar and 1 bar. A special case of this process is the OVJP (organic vapour jet printing) process, in which the materials are applied directly through a nozzle and are thus structured (for example M. S. Arnold et al., *Appl. Phys. Lett.* 2008, 92, 053301).

Preference is furthermore given to an organic electroluminescent device, characterised in that one or more layers are produced from solution, such as, for example, by spin coating, or by means of any desired printing process, such as, for example, screen printing, flexographic printing, nozzle printing or offset printing, but particularly preferably LITI (light induced thermal imaging, thermal transfer printing) or ink-jet printing. Soluble compounds of the formula (I) are necessary for this purpose. High solubility can be achieved through suitable substitution of the compounds.

For the production of an organic electroluminescent device according to the invention, it is furthermore preferred to apply one or more layers from solution and one or more layers by a sublimation process.

In accordance with the invention, the electronic devices comprising one or more compounds of the formula (I) can be employed in displays, as light sources in lighting applications and as light sources in medical and/or cosmetic applications (for example light therapy).

The invention is explained in greater detail by the following use examples, where the invention is not restricted to the scope of the examples.

WORKING EXAMPLES

A) Synthesis Examples

The following syntheses were carried out, unless indicated otherwise, under a protective-gas atmosphere in dried solvents. The starting materials can be purchased, for example, from ALDRICH or ABCR. Numbers in square brackets relate to the CAS numbers.

Example 1

Bisbiphenyl-4-ylbiphenyl-2-ylamine

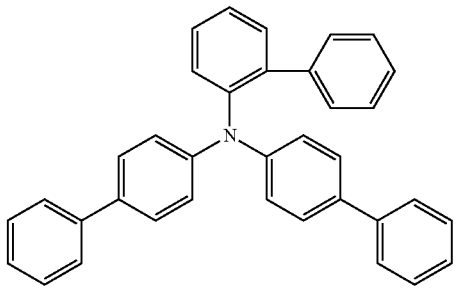 [SMILES: c1ccc(-c2ccc(N(c3ccc(-c4ccccc4)cc3)c3ccccc3-c3ccccc3)cc2)cc1]

A mixture of 94.3 g (404 mmol) of 2-bromobiphenyl [2052-07-5], 130.9 g (404 mmol) of bisbiphenyl-4-ylamine [102113-98-4], 48.1 g (500 mmol) of sodium tert-butoxide, 6.7 g (12 mmol) of DPPF, 1.8 g (8 mmol) of palladium(II) acetate and 1500 ml of mesitylene is heated under reflux for 55 h. After cooling, 1000 ml of water are added, the mixture is stirred for 30 min., the aqueous phase is separated off, the org. phase is washed three times with 500 ml of water each time and then evaporated in vacuo. The grey solid obtained in this way is subjected to hot extraction over aluminium oxide, basic, activity grade 1, subsequently recrystallised five times from DMF (about 2 ml/g) and then subjected to fractional sublimation twice (p about $10^{-5}$ mbar, T about 260-270° C.). Yield: 53.5 g (113 mmol), 28%; purity>99.9% according to HPLC.

The following compounds according to the invention are prepared analogously from the corresponding sec-amines and bromides:

| Ex. | sec-Amine | Bromide | tert-Amine | Yield |
|---|---|---|---|---|
| 2 | [102113-98-4] | [3282-24-4] | | 34% |

-continued
| Ex. | sec-Amine | Bromide | tert-Amine | Yield |
|---|---|---|---|---|
| 3 | 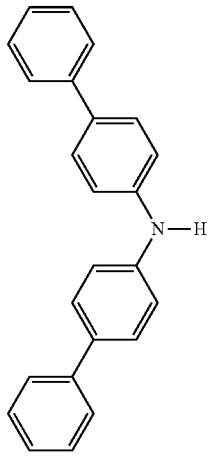<br>[102113-98-4] | 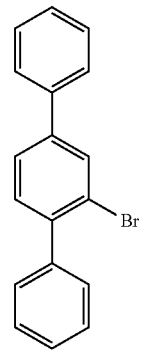<br>[3282-25-5] | 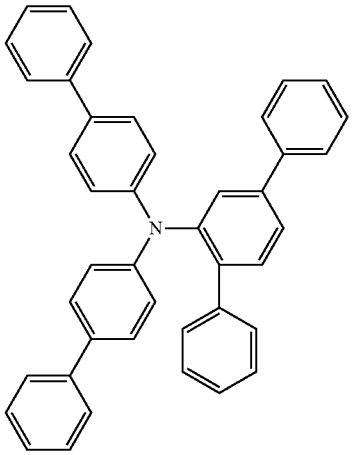 [SMILES: c1ccc(-c2ccc(N(c3ccc(-c4ccccc4)cc3)c3cc(-c4ccccc4)ccc3-c3ccccc3)cc2)cc1] | 29% |
| 4 | 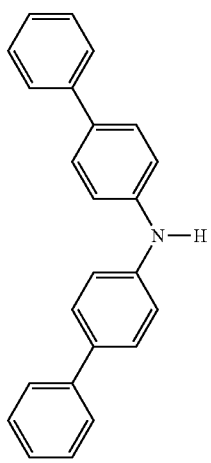<br>[102113-98-4] | 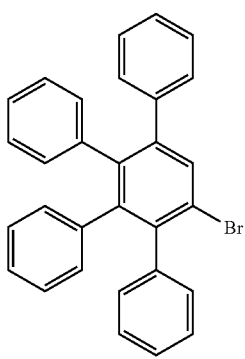<br>[879080-89-4] | 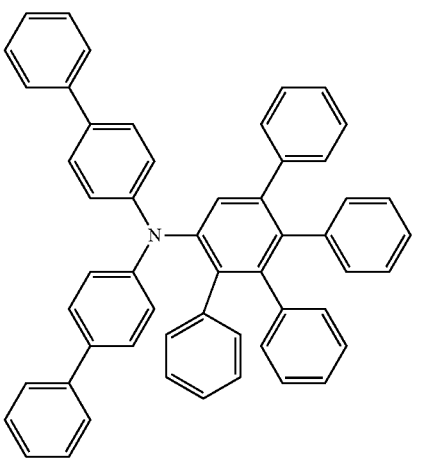 [SMILES: c1ccc(-c2ccc(N(c3ccc(-c4ccccc4)cc3)c3cc(-c4ccccc4)c(-c4ccccc4)c(-c4ccccc4)c3-c3ccccc3)cc2)cc1] | 23% |
| 5 | 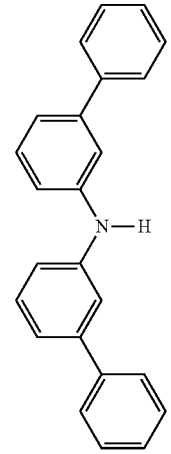<br>[169224-65-1] | 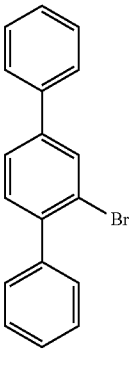<br>[3282-25-5] | 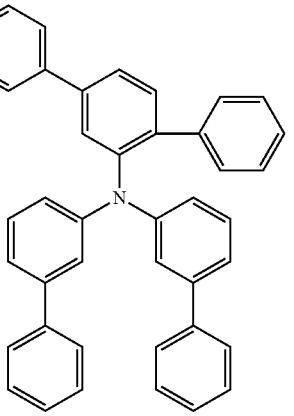 | 26% |

| Ex. | sec-Amine | Bromide | tert-Amine | Yield |
|---|---|---|---|---|
| 6 | 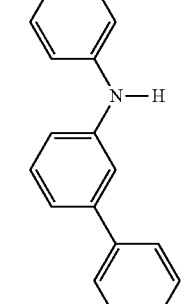 [570391-47-8] | 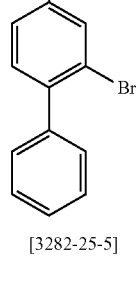 [3282-25-5] | 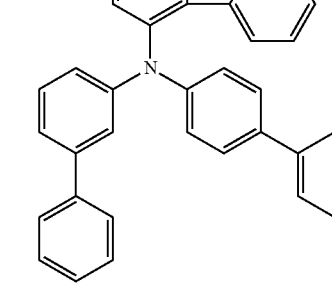 | 20% |
| 7 | 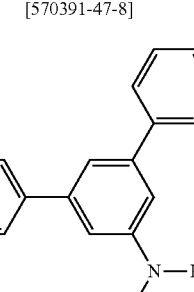 [1290039-78-9] | 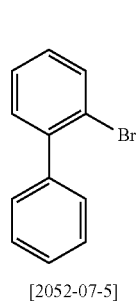 [SMILES: Brc1ccccc1-c1ccccc1] [2052-07-5] | 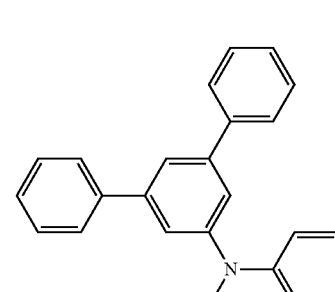 | 36% |
| 8 | 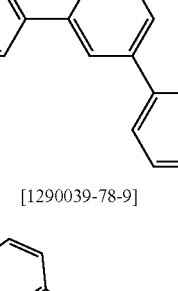 [1221237-92-8] |  [2052-07-5] | 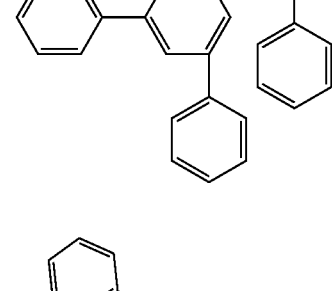 | 30% |

| Ex. | sec-Amine | Bromide | tert-Amine | Yield |
|---|---|---|---|---|
| 9 | [1258515-01-3] | [3282-25-5] | | 27% |

Example 10

Biphenyl-2-ylbis[1,1'3,3']terphenyl-4-ylamine

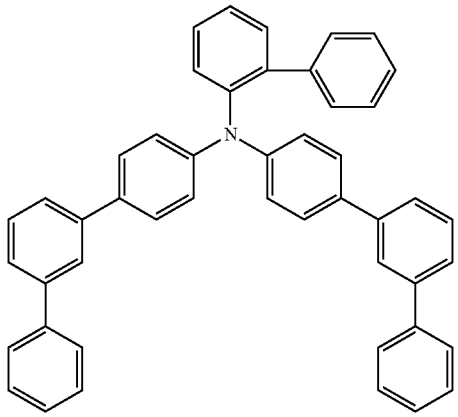 [SMILES: c1ccc(-c2cccc(-c3ccc(N(c4ccc(-c5cccc(-c6ccccc6)c5)cc4)c4ccccc4-c4ccccc4)cc3)c2)cc1]

A mixture of 33.8 g (200 mmol) of 2-aminobiphenyl [2052-07-5], 129.9 g (420 mmol) of 4-bromo[1,1'3,3']terphenyl[54590-37-3], 48.1 g (500 mmol) of sodium tert-butoxide, 6.7 g (12 mmol) of DPPF, 1.8 g (8 mmol) of palladium(II) acetate and 1500 ml of mesitylene is heated under reflux for 48 h. After cooling, 1000 ml of water are added, the mixture is stirred for 30 min., the aqueous phase is separated off, the org. phase is washed three times with 500 ml of water each time and then evaporated in vacuo. The grey solid obtained in this way is subjected to hot extraction over aluminium oxide, basic, activity grade 1, subsequently recrystallised five times from DMF (about 2 ml/g) and then subjected to fractional sublimation twice (p about $10^{-5}$ mbar, T about 300-310° C.). Yield: 48.0 g (77 mmol), 38.3%; purity >99.9% according to HPLC.

B) Device Examples

OLEDs according to the invention and OLEDs in accordance with the prior art are produced by a general process in accordance with WO 04/058911, which is adapted to the circumstances described here (layer-thickness variation, materials).

The data for various OLEDs are presented in Examples V1 to V6 and E1 to E12 below (see Tables 1 to 4) (V: examples in accordance with the prior art; E: examples according to the invention).

Glass plates coated with structured ITO (indium tin oxide) in a thickness of 150 nm are coated with 20 nm of PEDOT (poly(3,4-ethylenedioxy-2,5-thiophene), applied by spin coating from water; purchased from H. C. Starck, Goslar, Germany) for improved processing. These coated glass plates form the substrates to which the OLEDs are applied. The OLEDs basically have the following layer structure: substrate/hole-injection layer (HIL)/hole-transport layers (HTL)/interlayer (IL)/optional hole-transport layer (HTL2), electron-blocking layer (EBL)/emission layer (EML)/electron-transport layer (ETL) and finally a cathode. The cathode is formed by an aluminium layer with a thickness of 100 nm. The precise structure of the OLEDs is shown in Table 1 and 2. The materials required for the production of the OLEDs are shown in Table 5.

All materials are applied by thermal vapour deposition in a vacuum chamber. The emission layer here always consists of at least one matrix material (host material) and an emitting dopant (emitter), to which the matrix material or matrix materials is admixed in a certain proportion by volume by coevaporation. An expression such as H1:SEB1 (95%:5%) here means that material H1 is present in the layer in a proportion by volume of 95% and SEB1 is present in the layer in a proportion of 5%. Analogously, the electron-transport layer may also consist of a mixture of two materials.

The OLEDs are characterised by standard methods. For this purpose, the electroluminescence spectra, the current efficiency (measured in cd/A), the power efficiency (measured in lm/W) and the external quantum efficiency (EQE, measured in percent) as a function of the luminous density, calculated from current/voltage/luminous density characteristic lines (IUL characteristic lines) assuming Lambert emission characteristics, and the lifetime are determined. The electroluminescence spectra are determined at a luminous density of 1000 cd/m$^2$, and the CIE 1931 x and y colour coordinates are calculated therefrom. The expression U @ 1000 cd/m$^2$ in Table 2 and 4 denotes the voltage required for a luminous density of 1000 cd/m$^2$. Finally, EQE @ 1000 cd/m$^2$ denotes the external quantum efficiency at an operating luminous density of 1000 cd/m$^2$. LT80 @ 6000 cd/m2 is the lifetime by which the OLED at a luminance of 6000 cd/m$^2$ has dropped to 80% of the initial intensity, i.e. to 4800 cd/m$^2$. The data obtained for the various OLEDs are indicated in summary in Tables 2 and 4.

In particular, the compounds according to the invention are suitable as hole-transport material, for example in a hole-transport layer or in an electron-blocking layer, in OLEDs. They are suitable as a single layer, but also as mixed component as HTM, EBM (electron-blocking material) or within the emitting layer.

Compared with devices comprising NPB (V1 and V4), all samples comprising the compounds according to the invention exhibit higher efficiencies combined with the same or improved lifetimes.

Compared with reference material HTMV1 (V2 and V5), the compounds according to the invention have similar efficiencies and significantly better lifetimes in the blue-emitting and better lifetimes in green-emitting devices.

Compared with reference material HTMV2 (V3 and V6), the compounds according to the invention have similar efficiencies and significantly better lifetimes in green-emitting devices and better lifetimes in blue-emitting devices.

TABLE 1

Structure of the OLEDs

| Ex. | IL Thickness/ nm | HTL Thickness/ nm | IL Thickness/ nm | HTL2 Thickness/ nm | EBL Thickness/ nm | EML Thickness/ nm | ETL Thickness/ nm |
|---|---|---|---|---|---|---|---|
| V1 | HIL1 5 nm | HIL2 140 nm | HIL1 5 nm |  | NPB 20 nm | H1(95%): SEB1(5%) 20 nm | ETM1(50%): LiQ(50%) 30 nm |
| V2 | HIL1 5 nm | HIL2 130 nm | HIL1 5 nm | NPB 10 nm | HTMV1 20 nm | H1(95%): SEB1(5%) 20 nm | ETM1(50%): LiQ(50%) 30 nm |
| V3 | HIL1 5 nm | HIL2 130 nm | HIL1 5 nm | NPB 10 nm | HTMV2 20 nm | H1(95%): SEB1(5%) 20 nm | ETM1(50%): LiQ(50%) 30 nm |
| E1 | HIL1 5 nm | HIL2 130 nm | HIL1 5 nm | NPB 10 nm | HTM1 20 nm | H1(95%): SEB1(5%) 20 nm | ETM1(50%): LiQ(50%) 30 nm |
| E2 | HIL1 5 nm | HIL2 130 nm | HIL1 5 nm | NPB 10 nm | HTM2 20 nm | H1(95%): SEB1(5%) 20 nm | ETM1(50%): LiQ(50%) 30 nm |
| E3 | HIL1 5 nm | HIL2 130 nm | HIL1 5 nm | NPB 10 nm | HTM3 20 nm | H1(95%): SEB1(5%) 20 nm | ETM1(50%): LiQ(50%) 30 nm |
| E4 | HIL1 5 nm | HIL2 130 nm | HIL1 5 nm | NPB 10 nm | HTM4 20 nm | H1(95%): SEB1(5%) 20 nm | ETM1(50%): LiQ(50%) 30 nm |
| E5 | HIL1 5 nm | HIL2 130 nm | HIL1 5 nm | NPB 10 nm | HTM5 20 nm | H1(95%): SEB1(5%) 20 nm | ETM1(50%): LiQ(50%) 30 nm |
| E6 | HIL1 5 nm | HIL2 130 nm | HIL1 5 nm | NPB 10 nm | HTM6 20 nm | H1(95%): SEB1(5%) 20 nm | ETM1(50%): LiQ(50%) 30 nm |

TABLE 2

Data of the OLEDs

| Ex. | U @ 1000 cd/m2 V | EQE @ 1000 cd/m2 % | LT80 @ 6000 cd/m² [h] | CIE x | CIE y |
|---|---|---|---|---|---|
| V1 | 4.7 | 4.8 | 70 | 0.14 | 0.17 |
| V2 | 4.2 | 7.7 | 100 | 0.14 | 0.16 |
| V3 | 4.6 | 7.6 | 115 | 0.14 | 0.16 |
| E1 | 4.5 | 7.5 | 120 | 0.14 | 0.15 |
| E2 | 4.6 | 7.6 | 125 | 0.14 | 0.16 |
| E3 | 4.5 | 7.5 | 120 | 0.14 | 0.16 |
| E4 | 4.6 | 7.6 | 130 | 0.14 | 0.15 |
| E5 | 4.5 | 7.5 | 120 | 0.14 | 0.16 |
| E6 | 4.4 | 7.4 | 120 | 0.14 | 0.16 |

TABLE 3

Structure of the OLEDs

| Ex. | HTL Thickness/ nm | IL Thickness/ nm | HTL2 Thickness/ nm | EBL Thickness/ nm | EML Thickness/ nm | ETL Thickness/ nm |
|---|---|---|---|---|---|---|
| V4 | HIL2 70 nm | HIL1 5 nm |  | NPB 90 nm | H2(88%): Irpy(12%) 30 nm | ETM1(50%): LiQ(50%) 40 nm |
| V5 | HIL2 70 nm | HIL1 5 nm | NPB 10 nm | HTMV1 80 nm | H2(88%): Irpy(12%) 30 nm | ETM1(50%): LiQ(50%) 40 nm |
| V6 | HIL2 70 nm | HIL1 5 nm | NPB 10 nm | HTMV2 80 nm | H2(88%): Irpy(12%) 30 nm | ETM1(50%): LiQ(50%) 40 nm |
| E7 | HIL2 70 nm | HIL1 5 nm | NPB 10 nm | HTM1 80 nm | H2(88%): Irpy(12%) 30 nm | ETM1(50%): LiQ(50%) 40 nm |
| E8 | HIL2 70 nm | HIL1 5 nm | NPB 10 nm | HTM2 80 nm | H2(88%): Irpy(12%) 30 nm | ETM1(50%): LiQ(50%) 40 nm |
| E9 | HIL2 70 nm | HIL1 5 nm | NPB 10 nm | HTM3 80 nm | H2(88%): Irpy(12%) 30 nm | ETM1(50%): LiQ(50%) 40 nm |
| E10 | HIL2 70 nm | HIL1 5 nm | NPB 10 nm | HTM2 80 nm | H2(88%): Irpy(12%) 30 nm | ETM1(50%): LiQ(50%) 40 nm |

TABLE 3-continued

Structure of the OLEDs

| Ex. | HTL Thickness/ nm | IL Thickness/ nm | HTL2 Thickness/ nm | EBL Thickness/ nm | EML Thickness/ nm | ETL Thickness/ nm |
|---|---|---|---|---|---|---|
| E11 | HIL2 70 nm | HIL1 5 nm | NPB 10 nm | HTM3 80 nm | H2(88%): Irpy(12%) 30 nm | ETM1(50%): LiQ(50%) 40 nm |
| E12 | HIL2 70 nm | HIL1 5 nm | NPB 10 nm | HTM2 80 nm | H2(88%): Irpy(12%) 30 nm | ETM1(50%): LiQ(50%) 40 nm |

TABLE 4

Data of the OLEDs

| Ex. | U @ 1000 cd/m2 V | EQE @ 1000 cd/m2 % | LT80 @ 8000 cd/m$^2$ [h] | CIE x | CIE y |
|---|---|---|---|---|---|
| V4 | 3.6 | 14.4 | 85 | 0.32 | 0.63 |
| V5 | 3.6 | 17.8 | 120 | 0.35 | 0.62 |
| V6 | 3.6 | 17.8 | 115 | 0.34 | 0.62 |
| E7 | 3.5 | 17.7 | 145 | 0.34 | 0.63 |
| E8 | 3.5 | 17.3 | 150 | 0.36 | 0.62 |
| E9 | 3.6 | 17.5 | 140 | 0.35 | 0.62 |
| E10 | 3.6 | 17.8 | 125 | 0.34 | 0.63 |
| E11 | 3.6 | 17.7 | 145 | 0.35 | 0.63 |
| E12 | 3.5 | 17.3 | 145 | 0.35 | 0.62 |

TABLE 5

Structures of the materials used

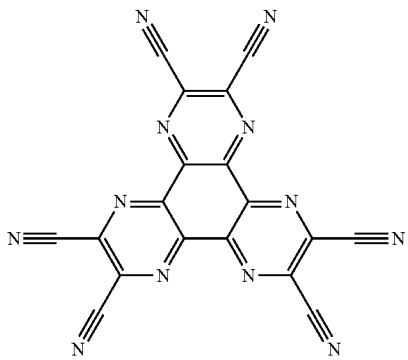 [SMILES: N#Cc1nc2c3nc(C#N)c(C#N)nc3c3nc(C#N)c(C#N)nc3c2nc1C#N]

HIL1

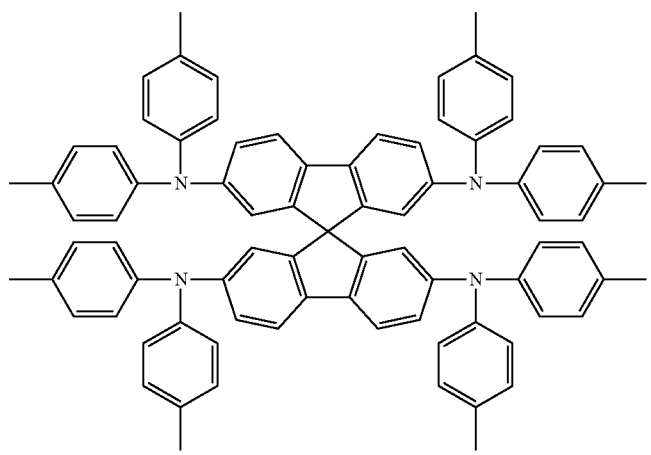

HIL2

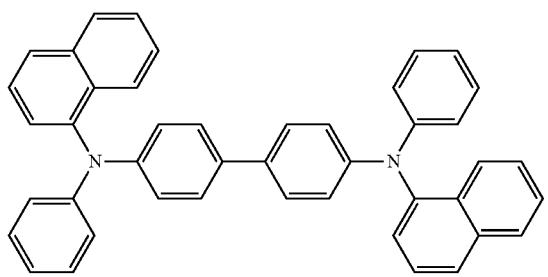 [SMILES: c1ccc(N(c2ccc(-c3ccc(N(c4ccccc4)c4cccc5ccccc45)cc3)cc2)c2cccc3ccccc23)cc1]

NPB

TABLE 5-continued
Structures of the materials used
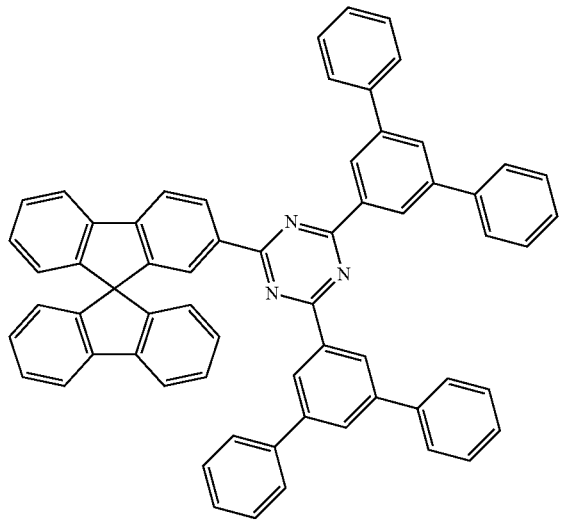 [SMILES: c1ccc(-c2cc(-c3ccccc3)cc(-c3nc(-c4cc(-c5ccccc5)cc(-c5ccccc5)c4)nc(-c4ccc5c(c4)C4(c6ccccc6-c6ccccc64)c4ccccc4-5)n3)c2)cc1]
ETM1
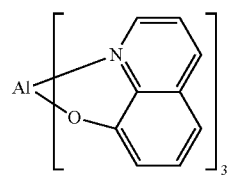
AlQ3
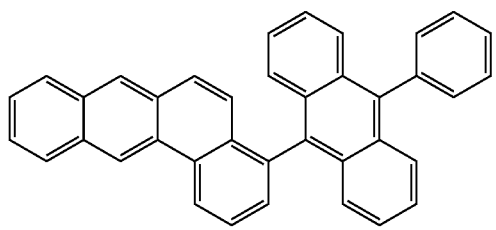 [SMILES: c1ccc(-c2c3ccccc3c(-c3cccc4c3ccc3cc5ccccc5cc34)c3ccccc23)cc1]
H1
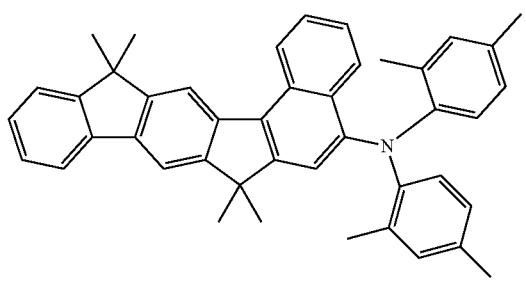 [SMILES: Cc1ccc(N(c2ccc(C)cc2C)c2cc3c(c4ccccc24)-c2cc4c(cc2C3(C)C)-c2ccccc2C4(C)C)c(C)c1]
SEB1
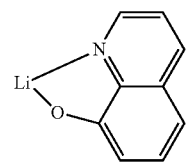
LiQ TABLE 5-continued
Structures of the materials used
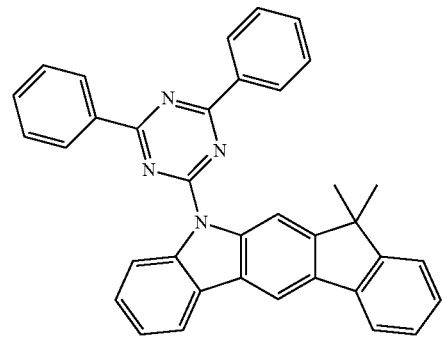 [SMILES: CC1(C)c2ccccc2-c2cc3c4ccccc4n(-c4nc(-c5ccccc5)nc(-c5ccccc5)n4)c3cc21]
H2
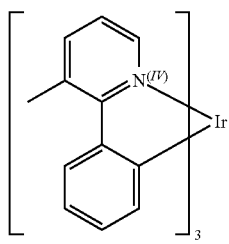
Irpy
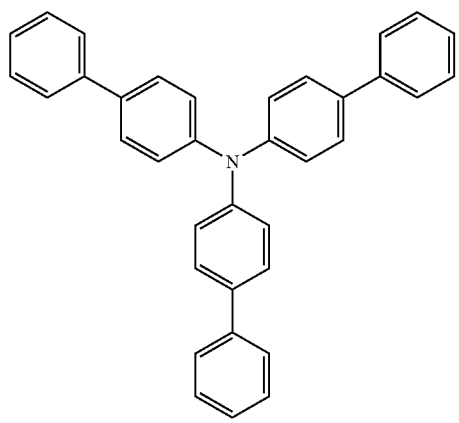 [SMILES: c1ccc(-c2ccc(N(c3ccc(-c4ccccc4)cc3)c3ccc(-c4ccccc4)cc3)cc2)cc1]
HTMV1
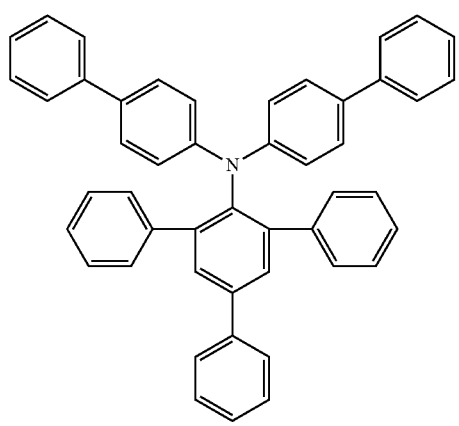 [SMILES: c1ccc(-c2ccc(N(c3ccc(-c4ccccc4)cc3)c3c(-c4ccccc4)cc(-c4ccccc4)cc3-c3ccccc3)cc2)cc1]
HTMV2

TABLE 5-continued
Structures of the materials used
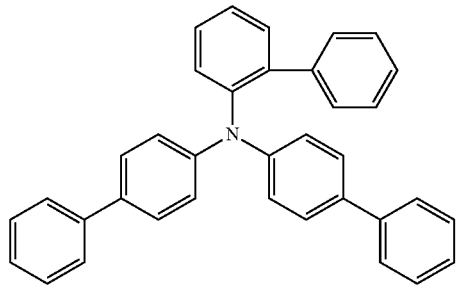 [SMILES: c1ccc(-c2ccc(N(c3ccc(-c4ccccc4)cc3)c3ccccc3-c3ccccc3)cc2)cc1]
HTM1
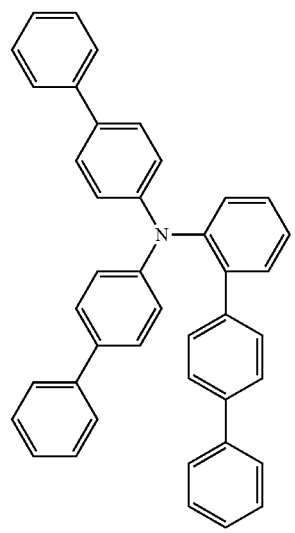 [SMILES: c1ccc(-c2ccc(-c3ccccc3N(c3ccc(-c4ccccc4)cc3)c3ccc(-c4ccccc4)cc3)cc2)cc1]
HTM2
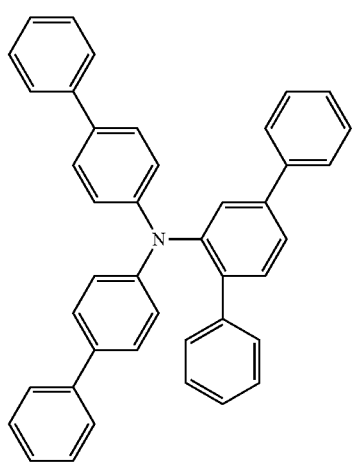 [SMILES: c1ccc(-c2ccc(N(c3ccc(-c4ccccc4)cc3)c3cc(-c4ccccc4)ccc3-c3ccccc3)cc2)cc1]
HTM3

TABLE 5-continued
Structures of the materials used
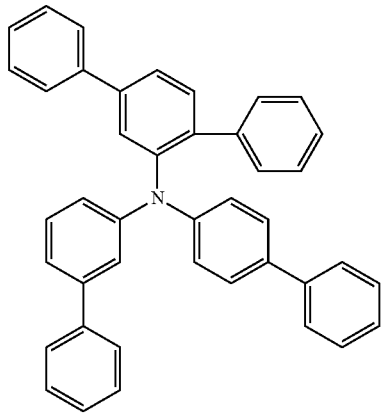 [SMILES: c1ccc(-c2ccc(N(c3cccc(-c4ccccc4)c3)c3cc(-c4ccccc4)ccc3-c3ccccc3)cc2)cc1]
HTM4
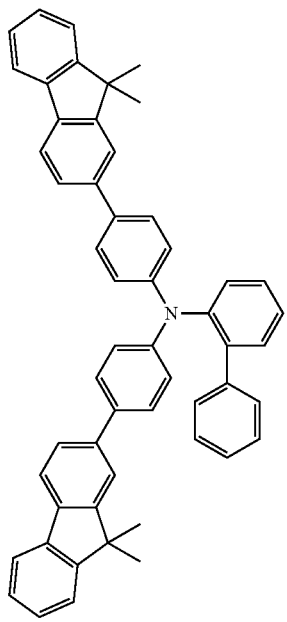 [SMILES: CC1(C)c2ccccc2-c2ccc(-c3ccc(N(c4ccc(-c5ccc6c(c5)C(C)(C)c5ccccc5-6)cc4)c4ccccc4-c4ccccc4)cc3)cc21]
HTM5
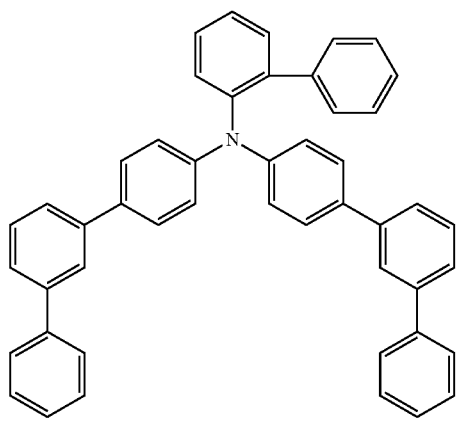 [SMILES: c1ccc(-c2cccc(-c3ccc(N(c4ccc(-c5cccc(-c6ccccc6)c5)cc4)c4ccccc4-c4ccccc4)cc3)c2)cc1]
HTM6

The invention claimed is:
1. A compound of formulae (I-2) or (I-6):

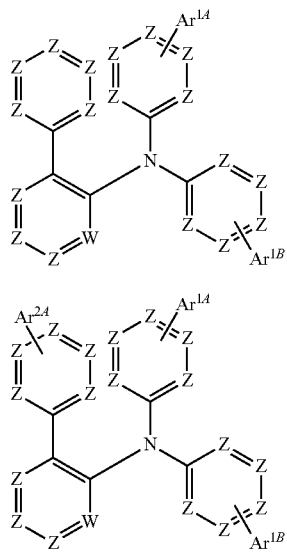

(I-2)

(I-6)

wherein
Z is on each occurrence CH, wherein Z is C if a group $Ar^{1A}$, $Ar^{1B}$, or $Ar^{2A}$ is bonded thereto;
W is CH;
$Ar^{1A}$ and $Ar^{1B}$
are on each occurrence, identically or differently, an aromatic ring system having 6 to 30 aromatic ring atoms optionally substituted by one or more radicals $R^1$;
$Ar^{2A}$
is on each occurrence, identically or differently, an aromatic ring system having 6 to 24 aromatic ring atoms optionally substituted by one or more radicals $R^1$;
$R^1$ is on each occurrence, identically or differently, H, D, F, C(=O)$R^2$, CN, Si($R^2$)$_3$, NO$_2$, P(=O)($R^2$)$_2$, S(=O)$R^2$, S(=O)$_2R^2$, a straight-chain alkyl, alkoxy, or thioalkyl group having 1 to 20 C atoms or a branched or cyclic alkyl, alkoxy, or thioalkyl group having 3 to 20 C atoms or an alkenyl or alkynyl group having 2 to 20 C atoms, wherein said groups are optionally substituted by one or more radicals $R^2$, wherein one or more CH$_2$ groups of said groups are optionally replaced by —$R^2$C=C$R^2$—, —C≡C—, Si($R^2$)$_2$, C=O, C=S, C=N$R^2$, —C(=O)O—, —C(=O)N$R^2$—, N$R^2$, P(=O)($R^2$), —O—, —S—, SO, or SO$_2$, and wherein one or more H atoms in said groups are optionally replaced by D, F, Cl, Br, I, CN, or NO$_2$, or an aromatic ring system having 5 to 30 aromatic ring atoms, which in each case is optionally substituted by one or more radicals $R^2$, and wherein two or more radicals $R^1$ are optionally linked to one another and optionally define a ring;
$R^2$ is on each occurrence, identically or differently, H, D, F, C(=O)$R^3$, CN, Si($R^3$)$_3$, NO$_2$, P(=O)($R^3$)$_2$, S(=O)$R^3$, S(=O)$_2R^3$, a straight-chain alkyl, alkoxy, or thioalkyl group having 1 to 20 C atoms or a branched or cyclic alkyl, alkoxy, or thioalkyl group having 3 to 20 C atoms or an alkenyl or alkynyl group having 2 to 20 C atoms, wherein said groups are optionally substituted by one or more radicals $R^3$, wherein one or more CH$_2$ groups of said groups are optionally replaced by —$R^3$C=C$R^3$—, —C≡C—, Si($R^3$)$_2$, C=O, C=S, C=N$R^3$, —C(=O)O—, —C(=O)N$R^3$—, N$R^3$, P(=O)($R^3$), —O—, —S—, SO, or SO$_2$, and wherein one or more H atoms in said groups are optionally replaced by D, F, Cl, Br, I, CN, or NO$_2$, or an aromatic ring system having 5 to 30 aromatic ring atoms, which in each case is optionally substituted by one or more radicals $R^3$, and wherein two or more radicals $R^2$ are optionally linked to one another and optionally define a ring;
$R^3$ is on each occurrence, identically or differently, H, D, F, or an aliphatic or aromatic organic radical having 1 to 20 C atoms, wherein one or more H atoms in said radical is optionally replaced by D or F; and wherein two or more substituents $R^3$ are optionally linked to one another and optionally define a ring;
wherein the three groups which are bonded to the central nitrogen atom, regarded as a whole, are not all identical, and
wherein the following compounds are excluded:

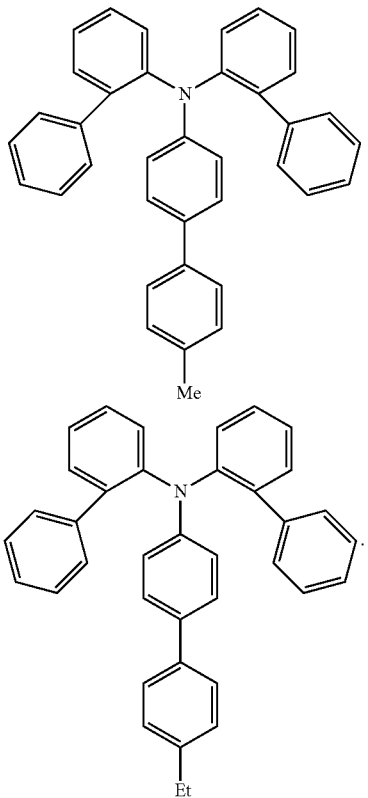

2. The compound of claim 1, wherein said compound contains no further arylamino group apart from the triarylamino group depicted in formula (I).
3. The compound of claim 1, wherein $Ar^{1A}$ and $Ar^{1B}$ are on each occurrence, identically or differently, an aromatic ring system having 6 to 18 aromatic ring atoms optionally substituted by one or more radicals $R^1$.
4. The compound of claim 1, wherein at least one of $Ar^{1A}$ and $Ar^{1B}$ is bonded its respective six-membered ring in the meta-position to the bond to the central nitrogen atom.
5. The compound of claim 1, wherein $Ar^{2A}$ is on each occurrence, identically or differently, an aromatic ring system having 6 to 12 aromatic ring atoms optionally substituted by one or more radicals $R^1$.
6. The compound of claim 1, wherein neither $Ar^{1A}$ nor $Ar^{1B}$ is bonded to its respective six-membered ring in the ortho-position to the bond to the central nitrogen atom.

7. A process for preparing the compound of claim 1, comprising linking an aryl compound containing an amino group and an aryl compound containing a leaving group to one another via a transition-metal-catalysed coupling reaction.

8. A formulation comprising at least one compound of claim 1 and at least one solvent.

9. An electronic device selected from the group consisting of organic integrated circuits, organic field-effect transistors, organic thin-film transistors, organic light-emitting transistors, organic solar cells, organic optical detectors, organic photoreceptors, organic field-quench devices, light-emitting electrochemical cells, organic laser diodes and organic electroluminescent devices, wherein said electronic device comprises at least one compound of claim 1.

10. The electronic device of claim 9, wherein said electronic device is an organic electroluminescent device and wherein said compound is employed in one or more of the following layers:
- in a hole-transport layer, a hole-injection layer or an electron-blocking layer as hole-transport material,
- in an emitting layer as matrix material in combination with one or more fluorescent or phosphorescent dopants.

* * * * *